(12) United States Patent
Peterman et al.

(10) Patent No.: US 8,158,088 B2
(45) Date of Patent: Apr. 17, 2012

(54) EXTRACTANT COMPOSITIONS FOR CO-EXTRACTING CESIUM AND STRONTIUM, A METHOD OF SEPARATING CESIUM AND STRONTIUM FROM AN AQUEOUS FEED, AND CALIXARENE COMPOUNDS

(75) Inventors: Dean R. Peterman, Idaho Falls, ID (US); David H. Meikrantz, Idaho Falls, ID (US); Jack D. Law, Pocatello, ID (US); Catherine L. Riddle, Idaho Falls, ID (US); Terry A. Todd, Firth, ID (US); Mitchell R. Greenhalgh, Iona, ID (US); Richard D. Tillotson, Moore, ID (US); Richard A. Bartsch, Lubbock, TX (US); Bruce A. Moyer, Oak Ridge, TN (US); Laetitia H. Delmau, Oak Ridge, TN (US); Peter V. Bonnesen, Knoxville, TN (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 555 days.

(21) Appl. No.: 12/268,189

(22) Filed: Nov. 10, 2008

(65) Prior Publication Data
US 2010/0116749 A1 May 13, 2010

(51) Int. Cl.
*B01D 11/00* (2006.01)
(52) U.S. Cl. ............... 423/8; 252/184; 252/364; 423/2; 423/181; 210/634; 588/20
(58) Field of Classification Search ................ 423/1, 2, 423/8, 181; 252/364, 184; 588/20; 210/634
See application file for complete search history.

(56) References Cited

U.S. PATENT DOCUMENTS

| | | | |
|---|---|---|---|
| 4,749,518 | A | 6/1988 | Davis, Jr. et al. |
| 5,100,585 | A | 3/1992 | Horwitz et al. |
| 5,344,623 | A | 9/1994 | Horwitz et al. |
| 5,346,618 | A | 9/1994 | Horwitz et al. |
| 5,393,892 | A | 2/1995 | Krakowiak et al. |

(Continued)

FOREIGN PATENT DOCUMENTS

SU 1706661 A1 9/1991
(Continued)

OTHER PUBLICATIONS

Development of Process Chemistry for the Removal of Cesium from Acidic Nuclear Waste by Cali[4]arene-crown-6 Ethers, Bonnesen et al., American Chemical Society, 2000, pp. 26-44.*

(Continued)

*Primary Examiner* — Mark Kopec
*Assistant Examiner* — Haidung Nguyen
(74) *Attorney, Agent, or Firm* — Traskbritt

(57) ABSTRACT

A mixed extractant solvent that includes at least one dialkyloxycalix[4]arenebenzocrown-6 compound, 4',4',(5')-di-(t-butyldicyclohexano)-18-crown-6, at least one modifier, and, optionally, a diluent. The dialkyloxycalix[4]arenebenzocrown-6 compound is 1,3-alternate-25,27-di(octyloxy)calix[4]arenebenzocrown-6, 1,3-alternate-25,27-di(decyloxy)calix[4]arenebenzocrown-6, 1,3-alternate-25,27-di(dodecyloxy)calix[4]arenebenzocrown-6, 1,3-alternate-25,27-di(2-ethylhexyl-1-oxy)calix[4]arenebenzocrown-6, 1,3-alternate-25,27-di(3,7-dimethyloctyl-1-oxy)calix[4]arenebenzocrown-6, 1,3-alternate-25,27-di(4-butyloctyl-1-oxy)calix[4]arenebenzocrown-6, or combinations thereof. The modifier is a primary alcohol. A method of separating cesium and strontium from an aqueous feed is also disclosed, as are dialkyloxycalix[4]arenebenzocrown-6 compounds and an alcohol modifier.

22 Claims, 26 Drawing Sheets

U.S. PATENT DOCUMENTS

| | | | |
|---|---|---|---|
| 5,443,731 | A | 8/1995 | Moyer et al. |
| 5,478,953 | A | 12/1995 | Gula et al. |
| 5,607,591 | A | 3/1997 | Dozol et al. |
| 5,666,641 | A | 9/1997 | Abney et al. |
| 5,666,642 | A | 9/1997 | Hawthorne et al. |
| 5,698,169 | A | 12/1997 | Hawthorne et al. |
| 5,866,087 | A | 2/1999 | Dozol et al. |
| 5,888,398 | A | 3/1999 | Dietz et al. |
| 5,926,687 | A | 7/1999 | Dozol et al. |
| 6,040,462 | A | 3/2000 | Oh et al. |
| 6,066,302 | A | 5/2000 | Bray |
| 6,156,282 | A | 12/2000 | Dozol et al. |
| 6,174,503 | B1 | 1/2001 | Moyer et al. |
| 6,214,234 | B1 | 4/2001 | Harjula et al. |
| 6,258,333 | B1 | 7/2001 | Romanovskiy et al. |
| 6,270,737 | B1 | 8/2001 | Zaitsev et al. |
| 6,306,355 | B1 | 10/2001 | Delmau et al. |
| 6,312,653 | B1 | 11/2001 | Delmau et al. |
| 6,456,680 | B1 | 9/2002 | Abalin et al. |
| 6,468,445 | B2 | 10/2002 | Romanovskiy et al. |
| 6,511,603 | B1 | 1/2003 | Dietz et al. |
| 6,566,561 | B1 | 5/2003 | Bonnesen et al. |
| 6,630,114 | B1 | 10/2003 | Dozol et al. |
| 6,696,589 | B2 * | 2/2004 | Ho .............................. 558/216 |
| 6,709,642 | B1 | 3/2004 | Dozol et al. |
| 7,200,198 | B2 | 4/2007 | Wieland et al. |
| 7,291,316 | B2 | 11/2007 | Meikrantz et al. |
| 7,479,261 | B2 | 1/2009 | Bray et al. |
| 7,524,469 | B2 | 4/2009 | Meikrantz et al. |
| 2001/0033814 | A1 | 10/2001 | Romanovskiy et al. |
| 2002/0094056 | A1 | 7/2002 | Satz et al. |
| 2005/0211955 | A1 * | 9/2005 | Meikrantz et al. ............ 252/364 |
| 2007/0212285 | A1 | 9/2007 | Egorov et al. |

FOREIGN PATENT DOCUMENTS

| | | |
|---|---|---|
| WO | 2006012153 | 2/2006 |
| WO | 2006038958 | 4/2006 |
| WO | 2007100799 | 9/2007 |

OTHER PUBLICATIONS

Bazelaire et al., "pH-Switchable Cesium Nitrate Extraction with Calix[4]arene Mono and bis(Benzo-crown-6) Ethers Bearing Amino Functionalities," Solvent Extr. Ion Exch. 22:637-661 (2004).

Bonnesen et al., "Alkaline-Side Extraction of Cesium from Savannah River Tank Waste Using a Calixarene-Crown Ether Extractant," ORNL/TM-13704, Oak Ridge National Laboratory: Oak ridge, TN, pp. ii-102 (Dec. 1998).

Bonnesen et al., "Development of Process Chemistry for the Removal of Cesium from Acidic Nuclear Waste by Calix[4]arene-crown-6 Ethers," ACS Sym. Ser. 757 (Calixarenes for Separations), Am. Chem. Soc., pp. 26-44 (2000).

Bonnesen et al., "A robust alkaline-side CSEX solvent suitable for removing cesium from Savannah River high level waste," Solvent Extr. Ion Exch. 2000, 18(6) 1079-1107.

Bonnesen et al., "Development of effective solvent modifiers for the solvent extraction of cesium from alkaline high-level tank waste," Solvent Extr. Ion Exch. 2003, 21(2) 141-170.

Casnati, et al., "Synthesis, Complexation, and Membrane Transport Studies of 1,3-Alternate Calix[4]arene-crown-6 Conformers: A New Class of Cesium Selective Ionophores," J. Am. Chem. Soc. 117:2767-2777 (1995).

Chiarizia et al., "Composition of the Organic Phase Species in the Synergistic Extraction of Sr2+ by Mixtures of Di(2-Ethylhexyl) Alkylenediphosphonic Acids and Dicydohexano-18-crown-6," Solvent Extr. and Ion Exch., 21(2):171-197 (2003).

Delmau et al., "Combined Extraction of Cesium and Strontium from Alkaline Nitrate Solutions," Solvent Extr. Ion Exch. 24:197-217 (2006).

Dietz et al., "Extraction of Strontium from Acidic Nitrate Media Using a Modified PUREX Solvent," Solvent Extr. and Ion Exch., 13(1), 1-17 (1995).

Dietz et al., "Substituent Effects in the Extraction of Cesium from Acidic Nitrate Media With Macrocyclic Polyethers," Solvent Extr. and Ion Exch., 14(3), 357-384 (1996).

Dozol et al., "A Solution for Cesium Removal from High-Salinity Acidic or Alkaline Liquid Waste: The Crown Calix[4] Arenes," Sep. Sci. and Technol., 34(6&7):877-909 (1999).

Dozol et al., "Extraction of rubidium and caesium from strongly alkaline media," Radiochim. Acta 92:175-182 (2004).

Duchemin et al., "Solvatochromic Solvent Polarity Measurements of Alcohol Solvent Modifiers and Correlation with Cesium Extraction Strength," Solvent Extr. and Ion Exch., 19(6):1037-1058 (2001).

Gupta, et al., "Effect of Diluents on the Extraction of Sr2+ from HNO3 Solutions with Dicyclohexano-18-crown-6," Solvent Extr. and Ion Exch., 21(1), 53-71 (2003).

Herbst et al., "Development and Testing of a Cobalt Dicarbollide Based Solvent Extraction Process for the Separation of Cesium and Strontium from Acidic Tank Waste," Sep. Sci. and Technol., 37(8), 1807-1831 (2002).

Horwitz et al., "A Combined Cesium-Strontium Extraction/Recovery Process," International Solvent Extraction Committee '96, pp. 1285-1290 (1996).

Horwitz et al., "SREX: A New Process for the Extraction and Recovery of Strontium From Acidic Nuclear Waste Streams," Solvent Extr. and Ion Exch., 9(1):1-25 (1991).

Kyba et al., "Host-Guest Complexation. 1. Concept and Illustration," J. Am. Chem. Soc. 99:8:2564-2571 (1977).

Lamb et al., "Novel Solvent System for Metal Ion Separation: Improved Solvent Extraction of Strontium(II) and Lead (II) as Dicyclohexano-18-crown-6 Complexes," Sep. Sci. and Technol., 34(13) :2583-2599 (1999).

Leonard et al., "Development of a Solvent Extraction Process for Cesium Removal From SRS Tank Waste," Sep. Sci. and Technol., 36(5-6):743-766 (2001).

Leonard et al., "Experimental Verification of Caustic-Side Solvent Extraction for Removal of Cesium from Tank Waste," Solvent Extr. and Ion Exch. 21(4) :505-526 (2003).

Moyer et al., "Complexation of Strontium in the Synergistic Extraction System Dicyclohexano-18-Crown-6, Versatic Acid, Carbon Tetrachloride," Solvent Ext. and Ion Exch., 4(1), 83-93 (1986).

Moyer et al., "Caustic-side solvent extraction chemical and physical properties: Progress in FY 2000 and FY 2001," Report ORNL/TM-2001/285, Oak Ridge National Laboratory: Oak Ridge, TN, Feb. 2002.

Norato et al., "Demonstration of the Caustic-Side Solvent Extraction Process for the Removal of 137 Cs from Savannah River Site High Level Waste," Sep. Sci. and Technol., 38(12-13):2647-2666 (2003).

Ouchi et al., "Convenient and Efficient Tosylation of Oligoethylene Glycols and the Related Alcohols in Tetrahydrofuran-Water in the Presence of Sodium Hydroxide," Bull. Chem. Soc. Jpn., 63(4), 1260-1262 (1990).

Sachleben et al., "Surveying the Extraction of Cesium Nitrate by 1,3-Alternate Calix[4]Arene Crown-6 Ethers in 1,2-Dichloroethane," Solvent Ext. and Ion Exch., 17(6), 1445-1459 (1999).

Sachleben et al., "Rational Design of Cesium-Selective Ionophores: Dihydrocalix[4]arene Crown-6 Ethers," Eur. J. Org. Chem. 4862-4869 (2003).

Shehata, F.A., "Extraction of Strontium from Nitric Acid Solutions by Selected Crown Ethers," J. of Radioanalytical and Nuclear Chem., Articles, 185(2) 411-417 (1994).

Tanigawa et al., "Solvent Extraction of Alkali Metals by Crown Ethers," Chem. Eng. J, 39:157-168 (1988).

White et al., "Stability Study of Cs Extraction Solvent," Sep. Sci. and Technol., 38(12-13):2667-2683 (2003).

Wood et al., "Effect of the Interference of Alkali and Alkaline Earth Metal Ions on the Extraction of 90SR From Acidic Nuclear Waste Solutions by 18-crown-6 Derivatives," Solvent Ext. and Ion Exch., 13(5), 829-844 (1995).

Wood et al., "Extraction of Lead and Strontium from Hazardous Waste Streams by Solvent Extraction with 4',4',(5')-DI-(T-Butyldicyclohexo)-18-crown-6," Solvent Ext. and Ion Exch., 15(1), 65-78 (1997).

Zirnhelt et al., "Strontium Extraction with a Polymer-Bound 18-Crown-6 Polyether," Sep. Sci. and Technol., 28 (15&16):2419-2429 (1993).

Bazelaire et al., pH-Switchable Cesium Nitrate Extraction with Calix[4]arene Mono and bis(Benzo-crown-6) Ethers Bearing Amino Functionalities, Solvent Extraction and Ion Exchange, vol. 22, No. 4, pp. 637-661, 2004.

Coppinger et al., Advantages of Palmolive Alternate, Programming Operation Hanford Laboratories Operation, Hanford Atomic Products Operation, Richland, Washington.

Tranter et al., An Inorganic Microsphere Composite for the Selective Removal of Cesium from Acidic Nuclear Waste Solutions. 2: Bengh-Scale Column Experiments modeling, and Preliminary Process Design, Solvent Extraction and Ion Exchange, vol. 27, pp. 219-243, 2009.

Dietz et al., Separation and Preconcentration of Cesium from acidic Media by Extraction Chromatography, Separation Science and Technology, vol. 41, pp. 2183-2204, 2006.

Meikrantz et al., Methods of Producing Cesium-131, U.S. Appl. No. 12/468,679, filed May 19, 2009.

International Search Report for PCT/US2005/03534, dated Jun. 28, 2006.

Written Opinion for PCT/US2005/03534, dated Jun. 28, 2006.

International Preliminary Report on Patentability for PCT/US2005/03534, dated Sep. 26, 2006.

Malinin et al., "Production of Cs-131 Without a Carrier and Estimation of the Cross Section of the Cs-131 (n, gamma) Cs-132 on Thermal Neutrons," Radiokihimiya, vol. 14, No. 6, pp. 866-869, Nov.-Dec. 1972.

* cited by examiner

EXTRACTANT COMPOSITIONS FOR CO-EXTRACTING CESIUM AND STRONTIUM, A METHOD OF SEPARATING CESIUM AND STRONTIUM FROM AN AQUEOUS FEED, AND CALIXARENE COMPOUNDS

STATEMENT REGARDING FEDERALLY SPONSORED RESEARCH OR DEVELOPMENT

This invention was made with government support under Contract No. DE-AC07-99ID13727 and Contract No. DE-AC07-05-ID14517 awarded by the United States Department of Energy The government has certain rights in the invention.

CROSS-REFERENCE TO RELATED APPLICATIONS

The subject matter of this application is related to U.S. application Ser. No. 12/468,679, filed May 19, 2009, and U.S. application Ser. No. 11/859,453, filed Sep. 21, 2007, now U.S. Pat. No. 7,524,469, issued Apr. 28, 2009, which is a divisional of U.S. application Ser. No. 10/808,039, filed Mar. 23, 2004, now U.S. Pat. No. 7,291,316, issued Nov. 6, 2007.

TECHNICAL FIELD

The present invention relates to separating cesium and strontium from an aqueous feed. More specifically, embodiments of the present invention relate to simultaneously separating cesium and strontium from the aqueous feed using a mixed extractant solvent.

BACKGROUND

Cesium-137, strontium-90, and actinides account for a significant amount of the radioactivity of liquid wastes, such as high level liquid wastes from nuclear fuel reprocessing. Cesium-137 and strontium-90 account for over 99.9% of the relative toxicity of the liquid waste once the actinides have been removed. Cesium-137 has a half-life ("$t_{1/2}$") of 30 years and strontium-90 has a $t_{1/2}$ of 29 years. This liquid waste is extremely hazardous and its disposal is expensive. To increase safe handling of the majority of the liquid waste and to significantly reduce its storage and disposal cost, the liquid waste is separated into two portions: one containing the majority of the radioactive components and one containing the bulk of the non-radioactive components. Removing the radioactive components allows the liquid waste to be decategorized and disposed of in geological formations after vitrification. Currently, separate technologies are used to remove the actinides and fission products from the liquid waste and, oftentimes, separate processes are used to remove specific radionuclides, such as cesium and strontium.

The ability to remove and recover cesium and strontium from spent nuclear fuel waste represents a significant issue regarding short-term heat loading in a geological repository. Cesium and strontium are major heat generators in the liquid waste and produce gamma and beta radiation. Removing the cesium-137 and strontium-90 would enable these radionuclides to be stored in a short-term waste facility, enabling long-term storage facilities to store waste closer together by eliminating some of the heat load.

Liquid extraction, sorption, and coprecipitation methods have been used to remove cesium or strontium from nuclear acidic waste solutions or related alkaline wastes. Numerous extractants have been identified that extract cesium or strontium from alkaline solutions or acidic solutions. The extractants are typically used in separate solvents that are designed to remove one of these radionuclides. For instance, crown ether compounds or calixarene crown ether compounds have been used to extract cesium. U.S. Pat. No. 6,174,503 to Moyer et al., U.S. Pat. No. 6,566,561 to Bonnesen et al., Duchemin et al., *Solv. Extr. Ion Exch.*, 19(6):1037-1058 (2001), Leonard et al., *Solv. Extr. Ion Exch.*, 21(4):505-526 (2003), Leonard et al., *Sep. Sci. Technol.*, 36(5-6):743-766 (2001), White et al., *Sep. Sci. Technol.*, 38(12-13):2667-2683 (2003), and Norato et al., *Sep. Sci. Technol.*, 38(12-13):2647-2666 (2003) disclose extracting cesium from alkaline solutions using calix[4]arene-crown ether compounds. The calix[4]arene-crown ether compounds and modifiers are dissolved in a diluent. The calixarene is calix[4]arene-bis(tert-octylbenzo)-crown-6 ("BOBCalixC6"). Strontium is removed from the alkaline solutions in a separate process using monosodium titanate. One specific extractant includes 0.007 M BOBCalixC6, 0.750 M 1-(2,2,3,3-tetrafluoropropoxy)-3-(4-sec-butylphenoxy)-2-propanol ("Cs-7SB"), 0.003 M tri-n-octylamine ("TOA"), and ISOPAR® L and is referred to herein as the caustic-side solvent extraction ("CSSX") solvent. The CSSX solvent provides a forward distribution ratio or coefficient for cesium ("$D_{Cs}$") of 8.0 from a 1 M nitric acid ("$HNO_3$") solution. Another specific extractant includes 0.01 M BOBCalixC6, 0.5 M Cs-7SB, 0.001 M TOA, and ISOPAR® L.

U.S. Pat. No. 5,926,687 to Dozol et al., and Bonnesen et al., "Development of Process Chemistry for the Removal of Cesium from Acidic Nuclear Waste by Calix[4]arene-crown-6 Ethers," *ACS Sym. Ser.* 757 (*Calixarenes for Separations*), 26-44 (2000), disclose extracting cesium from acidic solutions using calix[4]arene-crown ether compounds. While the tested calix[4]arene-crown ether compounds have high distribution coefficients for cesium, they have low distribution coefficients for strontium. Various calix[4]arene-crown ether compounds and modifiers were tested because the stability of the calix[4]arene-crown ether compounds and modifiers differed in each of these solutions. In Dozol et al., *Sep. Sci. Technol.*, 34(6&7):877-909 (1999), mono-crown or bis-crown calix[4]arenes in a 1,3 alternate conformation are disclosed to remove cesium from acidic or alkaline solutions.

Derivatives of mono-crown calixarenes have also been used to remove cesium. In Bazelaire et al., "pH-Switchable Cesium Nitrate Extraction with Calix[4]arene Mono and bis (Benzo-crown-6) Ethers Bearing Amino Functionalities," *Solvent Extr. Ion Exch.*, 22(4):637-661 (2004), the cesium extraction strength of mono- and bis-crown calixarenes functionalized with amine groups was evaluated. The cesium extraction strength of the amine-functionalized mono- and bis-crown calixarenes was compared to that of non-functionalized mono- and bis-crown calixarenes. The amine-functionalized mono- and bis-crown calixarenes had improved cesium stripping compared to the nonfunctionalized mono- and bis-crown calixarenes.

In Dozol et al., "Extraction of Rubidium and Caesium from Strongly Alkaline Media," *Radiochim. Acta* 92:175-182 (2004), the ability of calix[4]arene-crown-6 compounds to selectively extract cesium over rubidium was evaluated. Dioctyloxy-calix[4]arenebenzocrown-6 was found to be an effective extractant for cesium over rubidium. In Sachleben et al., "Rational Design of Cesium-Selective Ionophores: Dihydroxycalix[4]arene Crown-6 Ethers," *Eur. J. Org. Chem.* 4862-4869 (2003), the effect of substituent size on cation binding by 1,3-alternate-calix[4]arene-monocrown-6 ether compounds was determined. In addition to incorporating substituents into the crown-6 ether, phenyl groups of the calix[4]

arene of the 1,3-alternate-calix[4] arene-monocrown-6 ether compounds were substituted with hydrogen, octyloxy, or propenoxy groups.

U.S. Pat. No. 5,888,398 to Dietz et al. discloses using an 18-crown-6-ether to extract cesium from acidic solutions. The 18-crown-6-ether selectively extracts cesium over other ions, such as hydrogen, aluminum, calcium, boron, and strontium.

U.S. Pat. Nos. 5,344,623 and 5,346,618 to Horwitz et al., U.S. Pat. No. 6,511,603 to Dietz et al., Lamb et al., "Novel Solvent System for Metal Ion Separation: Improved Solvent Extraction of Strontium(II) and Lead(II) as Dicyclohexano-18-crown-6 Complexes," Sep. Sci. Technol., 34(13):2583-2599 (1999), Chiarizia et al., "Composition of the Organic Phase Species in the Synergistic Extraction of $Sr^{2+}$ by Mixtures of Di(2-Ethylhexyl)-Alkylenediphosphonic Acids and Dicyclohexano-18-crown-6," Solv. Extr. and Ion Exch., 21(2):171-197 (2003), and Tanigawa et al., Chem. Eng. J. 39(3):157-168 (1988) disclose extracting strontium from an acidic solution using crown ethers. One specific extractant includes a mixture of 0.15 M 4',4',(5')-di-(t-butyldicyclohexano)-18-crown-6 ("DtBuCH18C6") and 1.2 M tri-n-butyl phosphate ("TBP") in ISOPAR® L and is referred to herein as the strontium extraction ("SREX") solvent, as described in Horwitz et al., Solv. Extr. Ion Exch., 9(1):1-25 (1991). The SREX solvent provides a distribution ratio or coefficient for strontium ("$D_{Sr}$") of 0.7 from a 1 M nitric acid solution.

However, using separate extractants to remove the cesium and strontium is disadvantageous in regard to environmental concerns, safety, simplicity and effectiveness of processing, and undesirable generation of secondary waste.

Methods of extracting both cesium and strontium have also been disclosed. In U.S. Pat. No. 4,749,518 to Davis, Jr., et al., cesium is extracted from acidified nuclear waste with bis 4,4'(5) [1-hydroxy-2-ethylhexyl]benzo-18-crown-6 and a cation exchanger. The strontium is then extracted using bis 4,4'(5')[1-hydroxyheptyl]cyclohexano-18-crown-6 and a cation exchanger. In U.S. Pat. No. 5,393,892 to Krakowiak et al., a method of removing alkali metal and alkaline earth metals is disclosed. A solid inorganic support having a ligand covalently bonded thereto is contacted with a solution including the alkali metal and alkaline earth metals. The ligand is an oxygen donor macrocyclic polyether cryptand that selectively removes the alkali metal and alkaline earth metals. In U.S. Pat. No. 5,666,641 to Abney et al., a polymeric material including a polymer and a plasticizer is used to extract cesium and strontium. In U.S. Pat. No. 5,666,642 to Hawthorne et al., metal dicarbollide ion complexes are used to remove cesium and strontium from an aqueous fission product waste solution. The metal dicarbollide ion complexes are used to sequentially remove the cesium and then the strontium. In Horwitz et al., Proceedings of the International Solvent Extraction Conference '96, "A Combined Cesium-Strontium Extraction/Recovery Process," p. 1285-1290 (1996), an extraction process using di-t-butylcyclohexano-18-crown-6 and a macrocyclic polyether are disclosed to simultaneously extract cesium and strontium.

In addition, a large-scale demonstration of concurrent cesium and strontium partitioning from defense-related nuclear waste was performed in Russia using a cobalt dicarbollide extraction process. In U.S. Pat. No. 6,270,737 to Zaitsev et al., a composition of a complex organoboron compound and polyethylene glycol in an organofluorine diluent is used to extract cesium and strontium. The complex organoboron compound is a halogenated cobalt dicarbollide. In U.S. Pat. No. 6,258,333 to Romanovskiy et al., a composition of a complex organoboron compound, polyethylene glycol, and a neutral organophosphorus compound in a diluent is used to simultaneously extract cesium and strontium. The complex organoboron compound is a halogenated cobalt dicarbollide. However, this extraction process uses multiple chemicals and, therefore, adds significant volume to the waste volume produced by the extraction process.

U.S. Pat. No. 7,291,316 to Meikrantz et al., which is assigned to the Assignee of the present application and the disclosure of which is incorporated by reference herein in its entirety, discloses a method of removing cesium and strontium from an acidic nitrate solution. The method utilizes an extractant solvent including BOBCalixC6, DtBuCH18C6, Cs-7SB, and ISOPAR® L to remove the cesium and strontium. The extractant solvent optionally includes TOA. One embodiment of this extractant solvent includes 0.007 M BOBCalixC6, 0.075 M DtBuCH18C6, 0.75 M Cs-7SB modifier, and 0.003 M TOA in ISOPAR® L and is referred to herein as the "FPEX I process solvent." While this extractant solvent effectively separates cesium and strontium from acidic solutions having large quantities of actinides and lanthanides, the BOBCalixC6 has limited solubility in ISOPAR® L and the FPEX I process solvent is not stable in highly acidic solutions. Furthermore, the maximum concentration of BOBCalixC6 is solubility limited to approximately 0.007 M in an extractant solvent including 0.075 M DtBuCH18C6, 0.75 M Cs-7SB, and ISOPAR® L. In addition, the extractant solvent forms a third phase when exposed to a nitric acid concentration above 2.0 M. As a result, loading of the BOBCalixC6 with cesium during multistage extraction reduces distribution ratios for the cesium and inhibits total mass transfer.

It is desirable to develop a mixed extractant solvent that simultaneously separates cesium and strontium from the aqueous feed, increases the quantity of cesium that may be removed from the aqueous feed, and is more stable at a wider range of nitric acid concentrations, such as up to a nitric acid concentration of 5 M. It would also be desirable to develop a calixarene crown ether compound having a higher solubility in an isoparaffinic solvent than BOBCalixC6 and increased resistance to acidic degradation processes. In addition, it would be desirable to develop a modifier having high resistance to hydrolytic degradation for use in the mixed extractant solvent.

BRIEF SUMMARY

A mixed extractant solvent that includes at least one dialkyloxycalix[4]arenebenzocrown-6 compound, DtBuCH18C6, at least one modifier, and a diluent is disclosed.

A method of separating cesium and strontium from an aqueous feed is also disclosed. The method includes contacting an aqueous feed comprising cesium and strontium with a mixed extractant solvent and removing the cesium and strontium from the aqueous feed. The mixed extractant solvent includes at least one dialkyloxycalix[4]arenebenzocrown-6 compound, DtBuCH18C6, and at least one primary alcohol modifier dissolved in a diluent.

A calixarene compound having one of the following chemical structures:

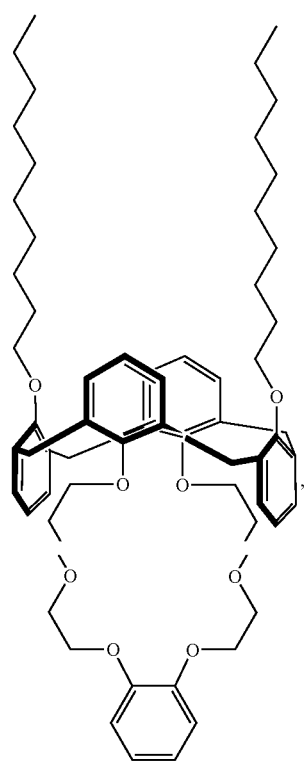
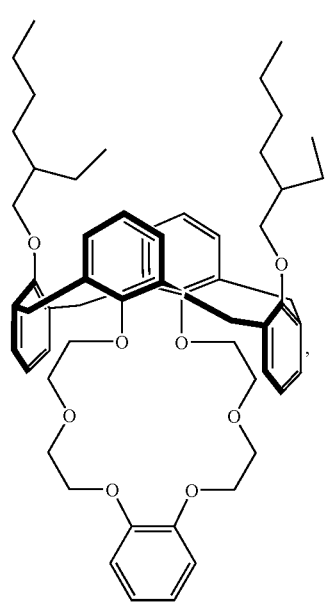
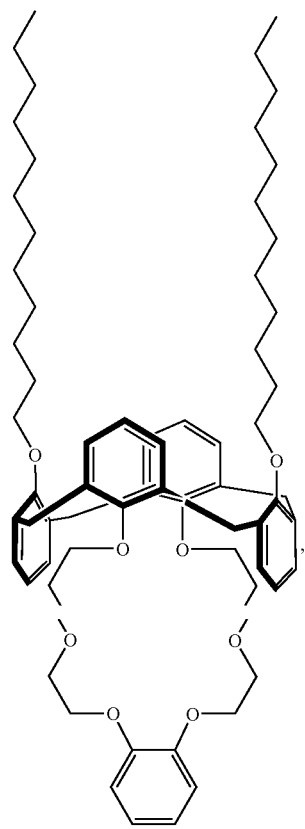
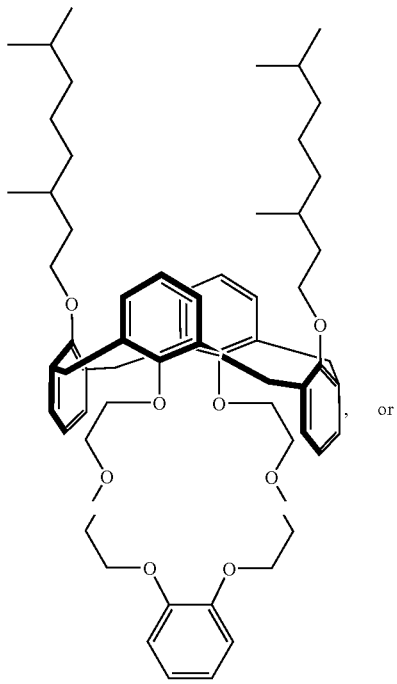

-continued

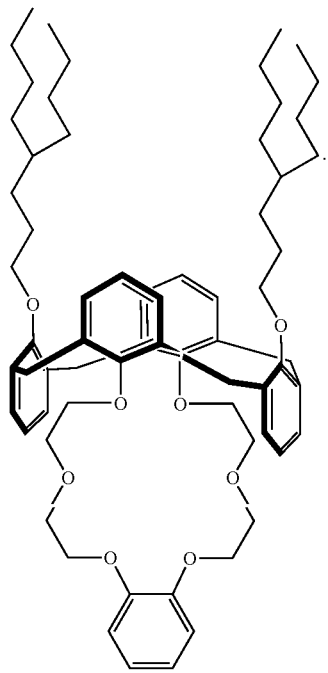

3-[4-(sec-butyl)phenoxy]-2-methyl-1-propanol and a mixed extractant solvent that includes BOBCalixC6, DtBuCH18C6, 3-[4-(sec-butyl)phenoxy]-2-methyl-1-propanol, and a diluent are also disclosed.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION

Figure 1:
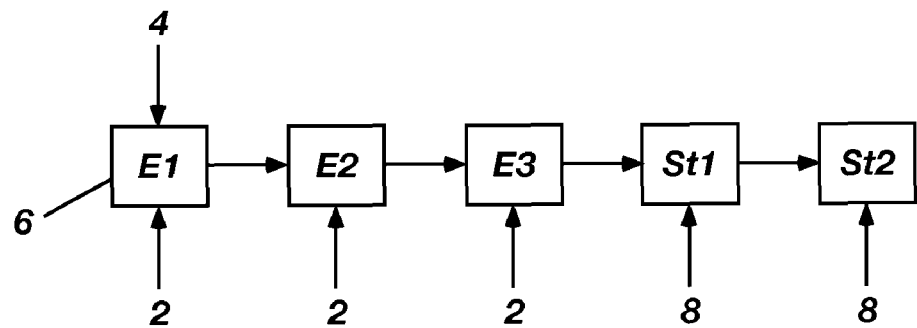
FIG. 1 is a flowsheet schematically illustrating cesium and strontium extraction from an aqueous feed.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the invention and such term is used in preference to the more restrictive term "is" so as to avoid any implication that other, compatible materials, structures, features and methods usable in combination therewith should or must be, excluded.

A mixed extractant solvent for extracting cesium and strontium from an aqueous feed is disclosed. The aqueous feed may have a nitric acid concentration of up to approximately 5 M. The mixed extractant solvent simultaneously or concurrently extracts cesium and strontium from the aqueous feed. The cesium and strontium are collectively referred to herein as "radionuclides." The mixed extractant solvent may include at least one crown ether compound, at least one dialkyloxycalix[4]arenebenzocrown-6 compound, and at least one modifier dissolved in a diluent. However, the modifier may be used neat, in which case the mixed extractant solvent may lack the diluent. The mixed extractant solvent may also include at least one crown ether compound, BOBCalixC6, and 4-(sec-butyl)phenoxy-2-methyl-1-propanol dissolved in a diluent. The mixed extractant solvent may, optionally, include an amine. The crown ether compound and the dialkyloxycalix[4]arenebenzocrown-6 compound or the crown ether compound and BOBCalixC6 are collectively referred to herein as "extractants." After contact with the aqueous feed, the mixed extractant solvent may form a first organic phase of a first extraction system that also includes a first aqueous phase. The extractants may be sufficiently soluble in the first organic phase so that a high concentration of the extractants is achieved. The extractants may also be relatively insoluble in the first aqueous phase. The concentration of the extractants in the first organic phase may be sufficiently high to effectively remove the radionuclides from the aqueous feed.

The crown ether used in the mixed extractant solvent may be 4',4',(5')-di-(t-butyldicyclohexano)-18-crown-6 ("DtBuCH18C6"). DtBuCH18C6 is available from Eichrom Industries, Inc. (Darien, Ill.), and has a molecular weight of 484.72 g/mol. The crown ether may be present in the mixed extractant solvent at from approximately 10 mM to approximately 500 mM, such as at from approximately 75 mM to approximately 150 mM. In one embodiment, the crown ether is present at from approximately 86 mM to approximately 108 mM. DtBuCH18C6 has the following structure:

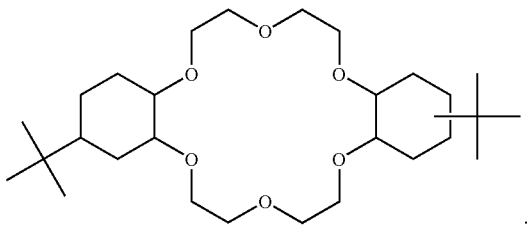

The DtBuCH18C6 used in the mixed extractant solvent may be a mixture of structural isomers or constitutional isomers having the above structure.

The dialkyloxycalix[4]arenebenzocrown-6 compound may have a general chemical structure as shown below:

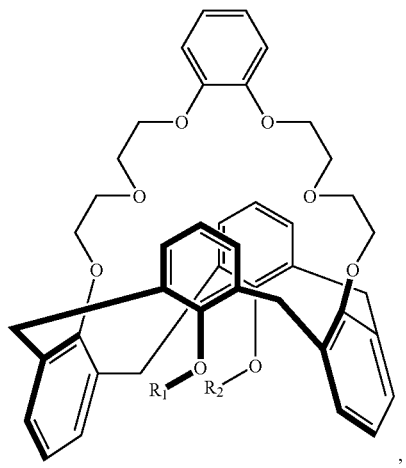

where each of $R_1$ and $R_2$ is an alkyl group and $R_1$ and $R_2$ may be the same or different. The alkyl group may be a saturated, straight, or branched hydrocarbon including from three carbon atoms to fourteen carbon atoms. Examples of the alkyl groups include, but are not limited to, propyl, methylethyl, butyl, methylpropyl, dimethylethyl, pentyl, methylbutyl, dimethylpropyl, trimethylethyl, ethylpropyl, hexyl, methylpentyl, dimethylbutyl, ethylbutyl, trimethylpropyl, heptyl, methylhexyl, dimethylpentyl, ethylpentyl, propylbutyl, trimethylbutyl, octyl, methylheptyl, dimethylhexyl, ethylhexyl, propylpentyl, trimethylpentyl, nonyl, methyloctyl, dimethylheptyl, ethylheptyl, propylhexyl, trimethylhexyl, decyl, methylnonyl, dimethyloctyl, ethyloctyl, propylheptyl, trimethylheptyl, butylhexyl, tetramethylhexyl, undecyl, methyldecyl, dimethylnonyl, ethylnonyl, propyloctyl, trimethyloctyl, butylheptyl, tetramethylheptyl, pentylhexyl, dodecyl, methylundecyl, dimethyldecyl, ethyldecyl, propylnonyl, trimethylnonyl, butyloctyl, tetramethyloctyl, pentylheptyl, tridecyl, methyldodecyl, dimethyl undecyl, ethylundecyl, propyldecyl, trimethyldecyl, butylnonyl, tetramethylnonyl, pentyloctyl, hexylheptyl, tetradecyl, methyltridecyl, dimethyldodecyl, ethyldodecyl, propylundecyl, trimethylundecyl, butyldecyl, pentylnonyl, or hexyloctyl.

The dialkyloxycalix[4]arenebenzocrown-6 compound may differ from BOBCalixC6 in that the octyl groups on the benzo ring of the bis-crown ether portion of BOBCalixC6 may be removed, and the bis-crown ether portion of BOBCalixC6 may be replaced by a mono-crown ether. Without being bound by any particular theory, it is believed that the octyl groups on the benzo ring of the bis-crown ether portion of BOBCalixC6 activate the benzyl ring toward nitration. Since the dialkyloxycalix[4]arenebenzocrown-6 compound does not include the octyl groups, the dialkyloxycalix[4]arenebenzocrown-6 compound may be less susceptible toward nitration than BOBCalixC6. It is also believed that replacing the bis-crown ether portion of BOBCalixC6 with a mono-crown ether may increase the solubility of the resulting dialkyloxycalix[4]arenebenzocrown-6 compound.

Examples of dialkyloxycalix[4]arenebenzocrown-6 compounds that may be used in the mixed extractant solvent include, but are not limited to:
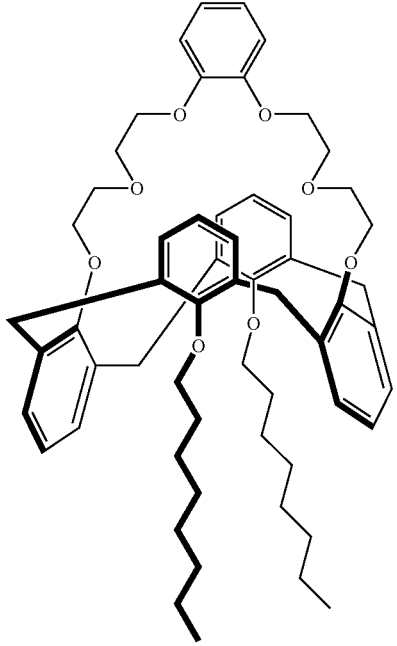
MC-8: 1,3-alternate-25,27-di(octyloxy)calix[4]arenebenzocrown-6,
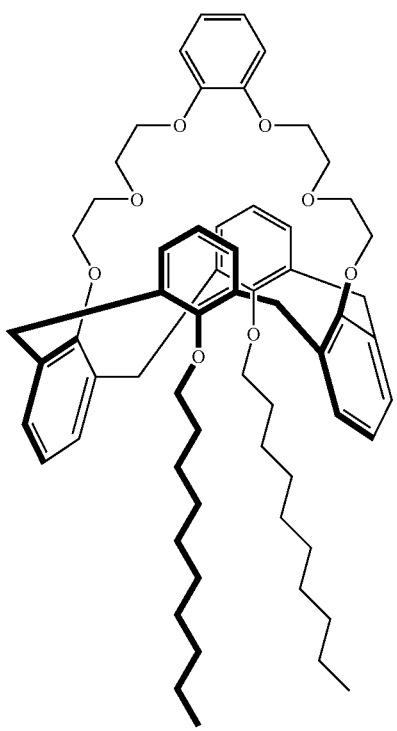
MC-10: 1,3-alternate-25,27-di(decyloxy)calix[4]arenebenzocrown-6,
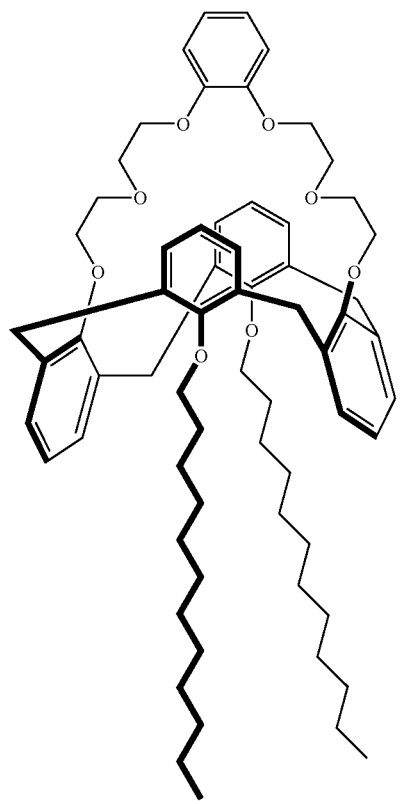
MC-12: 1,3-alternate-25,27-di(dodecyloxy)calix[4]arenebenzocrown-6,
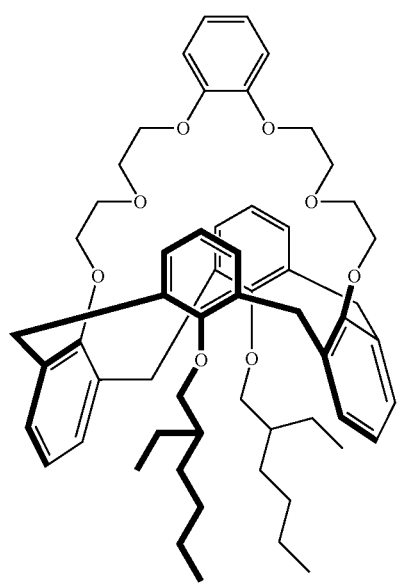
MC-8B: 1,3-alternate-25,27-di(2-ethylhexyl-1-oxy)calix[4]arenebenzocrown-6,

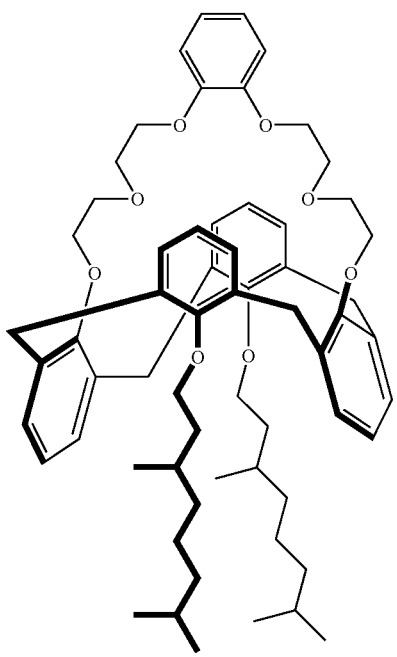

MC-10B: 1,3-alternate-25,27-di(3,7-dimethyloctyl-1-oxy)calix[4]arenebenzocrown-6,

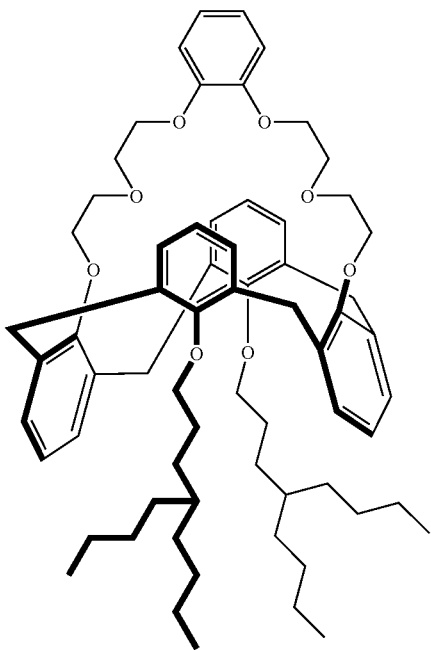

MC-12B: 1,3-alternate-25,27-di(4-butyloctyl-1-oxy)calix[4]arenebenzocrown-6, and combinations thereof. Structural isomers or constitutional isomers of MC-8B, MC-10B, and MC-12B may also be used in the mixed extractant solvent, alone or in combination with one or more of the above-mentioned structures.

In one embodiment, the dialkyloxycalix[4]arenebenzocrown-6 compound is MC-10B. As explained below, MC-10B exhibits desired characteristics (synthetic ease, extraction behavior, stability, etc.) that improve the overall performance of the FPEX I process solvent (0.007 M BOB-CalixC6, 0.075 M DtBuCH18C6, 0.75 M Cs-7SB modifier, and 0.003 M TOA in ISOPAR® L).

The dialkyloxycalix[4]arenebenzocrown-6 compounds may be synthesized by conventional techniques. By way of non-limiting example, MC-8, MC-10, MC-12, MC-8B, MC-10B, and MC-12B may be prepared by a method similar to that described in Sachleben et al., "Surveying the Extraction of Cesium Nitrate by 1,3-Alternate Calix[4]Arene Crown-6 Ethers in 1,2-Dichloroethane," *Solv. Extr. Ion Exch.,* 17(6): 1445-1459 (1999). To produce the dialkyloxycalix[4]arenebenzocrown-6 compounds, commercially available alcohols or alkyl bromides that correspond to the alkyl portion to be added to calix[4]arene may be transformed into corresponding alkyl tosylates or iodides by known methods, such as those described in Ouchi et al., "Convenient and Efficient Tosylation of Oligoethylene Glycols and the Related Alcohols in Tetrahydrofuran-Water in the Presence of Sodium Hydroxide," *Bull. Chem. Soc. Jpn.,* 63(4), 1260-1262 (1990) and Casnati et al., "Synthesis, Complexation, and Membrane Transport Studies of 1,3 Alternate Calix[4]arenecrown 6 Conformers: A New Class of Cesium Selective Ionophores," *J. Am. Chem. Soc.,* 117(10): 2767-2777 (1995), respectively. The resultant alkylating agents may be reacted with calix[4]arene and potassium carbonate in acetonitrile at reflux to provide 55%-85% yields of 25,27-di(alkyloxy)calix[4]arene compounds in the cone conformation. These diphenolic intermediates may be reacted with the ditosylate of bis-1,2[2'(2")-hydroxyethoxy)ethoxy]benzene, as described in Kyba et al., "Host-Guest Complexation. 1. Concept and Illustration," *J. Am. Chem. Soc.,* 99(8): 2564-2571 (1977), and cesium carbonate in acetonitrile at reflux to afford the 1,3-alternate-25,27-di(alkyloxy)calix[4]arenebenzocrown-6 compounds in 60%-85% yields.

The dialkyloxycalix[4]arenebenzocrown-6 compound may have increased solubility and stability in the mixed extractant solvent compared to the solubility and stability of BOBCalixC6 in the FPEX I process solvent. The increased solubility of the dialkyloxycalix[4]arenebenzocrown-6 compound may enable increased cesium loading in the mixed extractant solvent, which enables cesium and strontium to be more efficiently extracted from the aqueous feed. The solubility of the dialkyloxycalix[4]arenebenzocrown-6 compound in the mixed extractant solvent may be greater than approximately 7 mM, such as from greater than approximately 7 mM to approximately 50 mM. As such, the dialkyloxycalix[4]arenebenzocrown-6 compound may be present in the mixed extractant solvent at from approximately 7 mM to approximately 50 mM, such as from approximately 15 mM to approximately 45 mM. The dialkyloxycalix[4]arenebenzo-crown-6 compound may also have hydrolytic stability in the mixed extractant solvent.

The modifier may be at least one of an alcohol modifier and TBP. The modifier may be present in the mixed extractant solvent at from approximately 100 mM to approximately 3.0 M. Since the mixed extractant solvent includes two extractants and the modifier is selected to promote extraction of both the cesium and strontium, selection of the modifier to be utilized in the mixed extractant solvent may be complex. The modifier may increase the extractants' ability to extract the radionuclides and may enable a lower concentration of the extractants to be used in the mixed extractant solvent. Since many crown ether and dialkyloxycalix[4]arenebenzocrown-6 compounds have limited solubility in diluents, the modifier may also increase the extractants' solubility in the diluent. The modifier may also prevent the formation of a third phase between the mixed extractant solvent and the aqueous feed even when the aqueous feed has a high nitric acid concentration, such as a nitric acid concentration of up to approximately 5 M. In addition, the modifier may provide improved stripping efficiency of the radionuclides, enabling the cesium and strontium to be effectively removed or stripped from the first organic phase after the extraction. By way of non-limiting example, the modifier may provide effective stripping of the radionuclides from the first organic phase using a stripping solution having a nitric acid concentration of less than approximately 0.05 M.

The alcohol modifier may be a primary alcohol, such as at least one primary alkylphenoxy alcohol, at least one straight chain primary alcohol, at least one branched chain primary alcohol, or combinations thereof. If the alcohol modifier is a primary alkylphenoxy alcohol, the primary alkylphenoxy alcohol may lack fluorine substituents, such as an alkylphenoxy ethyl alcohol lacking fluorine substituents or an alkylphenoxy propyl alcohol lacking fluorine substituents. By way of non-limiting example, the primary alkylphenoxy alcohol may have the following chemical structure:

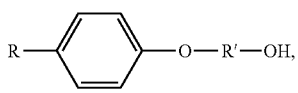

where R is a linear or branched alkyl chain having between 3 carbon atoms and 8 carbon atoms, and R' is a linear or branched carbon chain having between 2 carbon atoms and 4 carbon atoms, such that the total number of carbon atoms in the primary alkylphenoxy alcohol is between 11 carbon atoms and 18 carbon atoms. The R group may include, but is not limited to, propyl, methylethyl, butyl, methylpropyl, dimethylethyl, pentyl, methylbutyl, dimethylpropyl, trimethylethyl, ethylpropyl, hexyl, methylpentyl, dimethylbutyl, ethylbutyl, trimethylpropyl, heptyl, methylhexyl, dimethylpentyl, ethylpentyl, propylbutyl, trimethylbutyl, octyl, methylheptyl, dimethylhexyl, ethylhexyl, propylpentyl, or trimethylpentyl. The primary alkylphenoxy alcohol may also include compounds in which the R group is meta to the oxygen atom attached to the aromatic group. The R or alkyl group of the primary alkylphenoxy alcohol may include, but is not limited to, iso-butyl, sec-butyl, tert-butyl, tert-amyl, or tert-octyl. The primary alkylphenoxy alcohol may include alkyl branching on the ethyl or propyl groups. By way of non-limiting example, the alcohol modifier may be one of the following compounds:

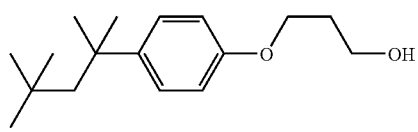

Cs-4: 3-[4-(tert-octyl)phenoxy]-1-propanol,

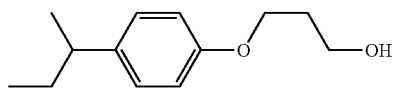

Cs-4SB: 3-[4-(sec-butyl)phenoxy]-1-propanol,

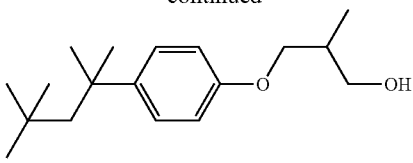

Cs-5: 3-[4-(tert-octyl)phenoxy]-2-methyl-1-propanol,

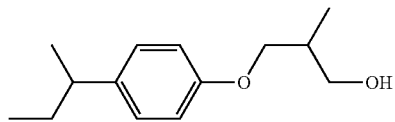

Cs-5SB: 3-[4-(sec-butyl)phenoxy]-2-methyl-1-propanol, or combinations thereof.

Cs-4, Cs-4SB, and Cs-5 illustrated above may be synthesized by conventional techniques, which are not described in detail herein. Cs-5SB may be synthesized as described below. In one embodiment, the alcohol modifier is Cs-4SB. In another embodiment, the alcohol modifier is Cs-5SB. If the primary alkylphenoxy alcohol is used as the modifier, the primary alkylphenoxy alcohol may be present in the mixed extractant solvent at from approximately 0.5 M to approximately 3.0 M, such as from approximately 1.0 M to approximately 1.5 M.

Alternatively, the alcohol modifier may be a cyclohexyloxy analog of one of the alkylphenoxy alcohols. By way of non-limiting example, the cyclohexyloxy analog may have the following chemical structure:

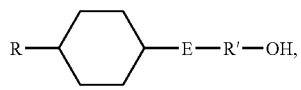

where R is a linear or branched alkyl chain having between 2 carbon atoms and 8 carbon atoms, E is an oxygen atom or methylene (—$CH_2$—) group, and R' is a linear or branched carbon chain having between 2 carbon atoms and 4 carbon atoms, such that the total number of carbon atoms in the cyclohexyloxy analog is between 12 carbon atoms and 18 carbon atoms. The R group may include, but is not limited to, propyl, methylethyl, butyl, methylpropyl, dimethylethyl, pentyl, methylbutyl, dimethylpropyl, trimethylethyl, ethylpropyl, hexyl, methylpentyl, dimethylbutyl, ethylbutyl, trimethylpropyl, heptyl, methylhexyl, dimethylpentyl, ethylpentyl, propylbutyl, trimethylbutyl, octyl, methylheptyl, dimethylhexyl, ethylhexyl, propylpentyl, trimethylpentyl. The cyclohexyloxy analog may also include compounds in which the R group is meta to the E group.

Alternatively, the alcohol modifier may be a straight chain primary alcohol or a branched chain primary alcohol. The straight chain primary alcohol may include from 6 carbons to 12 carbons. The straight chain primary alcohol may be an isomer of hexanol, heptanol, octanol, nonanol, decanol, undecanol, dodecanol, or combinations thereof, such as 1-hexanol, 1-heptanol, 1-octanol, 1-nonanol, 1-decanol, 1-undecanol, 1-dodecanol, or combinations thereof. Such primary alcohols are sold under the NEODOL® tradename and are commercially available from Shell Chemicals LP (Houston, Tex.), or may be synthesized by conventional techniques, which are not described in detail herein. In one embodiment, the alcohol modifier is 1-octanol. In another embodiment, the alcohol modifier is 1-decanol. In another embodiment, the alcohol modifier is 1-dodecanol. In another embodiment, the straight chain primary alcohol is NEODOL® 91, which includes a combination of from 75% by weight to 85% by weight of $C_9$, $C_{10}$, and $C_{11}$ high linearity, primary alcohols.

The branched chain primary alcohol may include from 6 carbons to 13 carbons. By way of non-limiting example, the branched chain primary alcohol may be a branched isomer of hexanol, heptanol, octanol, nonanol, decanol, undecanol, dodecanol, tridecanol, or combinations thereof. The branched chain primary alcohol may have a hydroxyl radical bound to a primary carbon atom and at least one alkyl group, such as a methyl, ethyl, or propyl group, bound to another carbon atom of the branched chain primary alcohol. The branched chain primary alcohol may include, but is not limited to, methylpentanol, ethylbutanol, methylhexanol, ethylpentanol, methylheptanol, ethylhexanol, methyloctanol, ethylheptanol, methylnonanol, ethyloctanol, methyldecanol, ethylnonanol, methylundecanol, ethyldecanol, methyldodecanol, ethylundecanol, or combinations thereof. Suitable primary alcohols are sold under the EXXAL® tradename and are commercially available from Exxon Mobil Chemical Company (Houston, Tex.), or may be synthesized by conventional techniques, which are not described in detail herein. The EXXAL® alcohols are distilled, high-purity, clear liquids that include primary aliphatic alcohols produced from selected olefins. The EXXAL® alcohols are mixtures of isomers of different branched structures, primarily methyl branching, with both odd- and even-numbered carbon chains ranging from $C_7$ to $C_{13}$. In one embodiment, the alcohol modifier is EXXAL® 8 isooctyl alcohol. In another embodiment, the alcohol modifier is EXXAL® 10 isodecyl alcohol. In another embodiment, the alcohol modifier is EXXAL® 12 dodecyl alcohol. The EXXAL® alcohol may provide increased stability and solubility of the dialkyloxycalix[4]arenebenzocrown-6 compound in the mixed extraction solvent.

In addition, combinations of primary alcohols may be used, such as combinations of straight chain primary alcohols, combinations of branched chain primary alcohols, or combinations of straight chain primary alcohols and branched chain primary alcohols. If the straight chain or branched chain primary alcohol is used as the modifier, the straight chain or branched chain primary alcohol may be present in the mixed extractant solvent at from approximately 0.5 M to approximately 3.0 M, such as from approximately 1.0 M to approximately 1.5 M. The straight chain or branched chain primary alcohol may be used in the mixed extractant solvent when the aqueous feed from which the radionuclides are to be removed has a nitric acid concentration above approximately 0.5 M, such as from approximately 1.5 M to approximately 5 M.

The efficacy of the alcohol modifiers described above to improve the extraction performance of the mixed extractant solvent is unexpected because alcohol modifiers utilized to extract cesium from alkaline solutions were previously thought to require fluorine groups. It was believed that alcohol modifiers lacking fluorine groups would not have sufficient strength to extract the cesium. For instance, when EXXAL® 12 dodecyl alcohol was previously investigated for extracting cesium from alkaline solutions, as described in U.S. Pat. No. 6,174,503, the EXXAL® 12 dodecyl alcohol lacked sufficient strength to effectively extract the cesium. Utilizing alcohol modifiers that lack fluorine groups is advantageous because, if present, the fluorine groups may be released during chemical or radiolytic degradation of the alcohol modifier. In addition, alcohol modifiers that lack fluorine groups are typically cheaper than those having fluorine groups.

The alcohol modifier may also be a secondary alcohol or a tertiary alcohol, such as at least one secondary alkylphenoxy alcohol, at least one straight chain or branched chain secondary alcohol, at least one tertiary alkylphenoxy alcohol, at least one branched chain tertiary alcohol, or combinations thereof. By way of non-limiting example, the secondary alkylphenoxy alcohol may have a general structure of

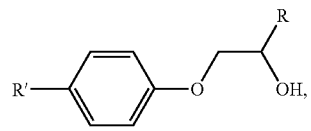

where R and R' are as described in Leonard et al., *Sep. Sci. Technol.*, 36(5-6):743-766 (2001), Leonard et al., *Solv. Extr. Ion Exch.*, 21(4):505-526 (2003), and Duchemin et al., *Solvent Extr. Ion Exch.*, 19(6):1037-1058 (2001). In one embodiment, the alcohol modifier is 1-(2,2,3,3-tetrafluoropropoxy)-3-(4-sec-butylphenoxy)-2-propanol ("Cs-7SB"), which has the following structure:

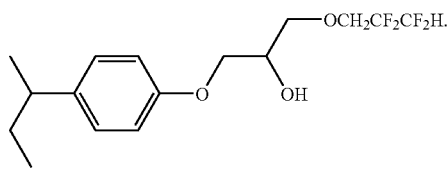

If Cs-7SB is used as the alcohol modifier, Cs-7SB may be present in the mixed extractant solvent at from approximately 200 mM to approximately 1.5 M. Cs-7SB may be used in the mixed extractant solvent when the aqueous feed has a nitric acid concentration of up to approximately 1.5 M. However, at nitric acid concentrations above approximately 1.5 M, formation of a third phase occurs when the mixed extractant solvent is added to the aqueous feed. Cs-7SB may also be used in the mixed extractant solvent in combination with another alcohol modifier, such as a primary alcohol modifier.

The straight chain secondary alcohol may include from 6 carbons to 12 carbons. The straight chain secondary alcohol may be an isomer of hexanol, heptanol, octanol, nonanol, decanol, undecanol, dodecanol, or combinations thereof, such as 2-hexanol, 2-heptanol, 2-octanol, 2-nonanol, 2-decanol, 2-undecanol, 2-dodecanol, or combinations thereof. The branched chain secondary alcohol may include from 6 carbons to 13 carbons. By way of non-limiting example, the branched chain secondary alcohol may be a branched isomer of hexanol, heptanol, octanol, nonanol, decanol, undecanol, dodecanol, or tridecanol having a hydroxyl radical bound to a secondary carbon atom and at least one alkyl group, such as a methyl, ethyl, or propyl group, bound to another carbon atom of the branched chain secondary alcohol. The branched chain secondary alcohol may include, but is not limited to, methylpentan-2-ol, ethylbutan-2-ol, methylhexan-2-ol, ethylpentan-2-ol, methylheptan-2-ol, ethylhexan-2-ol, methyloctan-2-ol, ethylheptan-2-ol, methylnonan-2-ol, ethyloctan-2-ol, methyldecan-2-ol, ethylnonan-2-ol, methylundecan-2-ol, ethyldecan-2-ol, methyldodecan-2-ol, ethylundecan-2-ol, or combinations thereof.

The branched chain tertiary alcohol may include from 6 carbons to 13 carbons. By way of non-limiting example, the branched chain tertiary alcohol may be a branched isomer of hexanol, heptanol, octanol, nonanol, decanol, undecanol, dodecanol, or tridecanol having a hydroxyl radical bound to a tertiary carbon atom and at least one alkyl group, such as a methyl, ethyl, or propyl group, bound to another carbon atom of the branched chain tertiary alcohol.

In addition, a combination of any of the above-mentioned alcohol modifiers may be used. By way of non-limiting example, combinations of primary alcohols and secondary alcohols, primary alcohols and tertiary alcohols, secondary alcohols and tertiary alcohols, or primary alcohols, secondary alcohols, and tertiary alcohols may be used. By way of non-limiting example, the alcohol modifier may include a combination of Cs-7SB and EXXAL® 12.

The diluent may be an inert diluent, such as a straight chain hydrocarbon diluent. For instance, the diluent may be an isoparaffinic hydrocarbon diluent, such as ISOPAR® L or ISOPAR® M. ISOPAR® L includes a mixture of $C_{10}$-$C_{12}$, isoparaffinic hydrocarbons and is available from Exxon Chemical Co. (Houston, Tex.). ISOPAR® M includes a mixture of $C_{12}$-$C_{15}$ isoparaffinic hydrocarbons and is available from Exxon Mobil Chemical Co. (Houston, Tex.). However, other isoparaffinic hydrocarbons may be used as the diluent.

The amine, if present, may be a lipophilic amine, such as primary, secondary, tertiary, or quaternary amine including, but not limited to, TOA, ALAMINE® 336 (a tertiary amine containing 8-10 carbon aliphatic chains (tricaprylyl amine)), ALIQUAT® 336, tri-n-decylamine, tri-n-dodecylamine, tri-isooctylamine, triisodecylamine, triisotridecylamine, a tetraheptylammonium salt, PRIMINE® JMT (a tertiary alkyl primary amine), didecylamine, didodecylamine, tri-2-ethylhexylamine, a tetraalkylphosphonium salt, a tetraalkylammonium salt, a long-chain N-alkylpyridinium salt, and combinations thereof. The amine, if present, may improve the ability to remove or recover the radionuclides from the first organic phase of the first extraction system. However, the presence of the amine in the mixed extractant solvent may have minimal effect on extracting the radionuclides from the aqueous feed and into the first organic phase of the first extraction system.

In one embodiment, the mixed extractant solvent includes 0.02 M MC-10B, 0.09 M DtBuCH18C6, and 1.5 M of the alcohol modifier, such as 1.5 M of Cs-4SB, Cs-5SB, 1-octanol, 1-decanol, 1-dodecanol, EXXAL® 8 isooctyl alcohol, EXXAL® 10 decyl alcohol, or EXXAL® 12 dodecyl alcohol. In another embodiment, the mixed extractant solvent includes 0.02 M MC-10B, 0.09 M DtBuCH18C6, and 0.75 M of Cs-5SB.

The mixed extractant solvent may include cesium extractants and strontium extractants in addition to the dialkyloxycalix[4]arenebenzocrown-6 compound and DtBuCH18C6. For instance, combinations of other crown ethers and calixarenes that are capable of extracting cesium and strontium may be used in combination with the dialkyloxycalix[4]arenebenzocrown-6 compound and DtBuCH18C6. In general, crown ethers having a dicyclohexano structure may provide selectivity for strontium and those having a dibenzo structure may provide selectivity for cesium. Additional crown ethers are known in the art and include, but are not limited to, cis-dicyclohexano-18-crown-6 ("DCH18C6"), dimethyl derivatives thereof, and di-t-butyl derivatives thereof. Additional calixarenes are known in the art and may be used in the mixed extractant solvent, such as other derivatives of calix[4]arene-crown-6 ether including, but not limited to, mono- and bis-crown-6-derivatives of 1,3-calix[4]arenes. These calixarenes may be in cone, partial cone, 1,2 alternate, or 1,3 alternate conformations.

The mixed extractant solvent may be prepared by combining the crown ether, the dialkyloxycalix[4]arenebenzocrown-6 compound or the BOBCalixC6, the modifier, and the amine (if present) with the diluent to form a mixture. Initially, a portion of a final volume of the diluent may be added to the extractants, the modifier, and the amine (if present) to lower the viscosity of the mixture. The mixture may be stirred overnight and the remainder of the diluent may then be added.

The increased solubility of the dialkyloxycalix[4]arenebenzocrown-6 compound in the mixed extractant solvent may enable the mixed extractant solvent to achieve single stage forward extraction distribution ratios for cesium as high as approximately 75 at 0.05 M of dialkyloxycalix[4]arenebenzocrown-6 compound. By way of non-limiting example, successive or multistage forward extraction distribution ratios for cesium of 17, 15, and 10 may be achieved at 0.025 M dialkyloxycalix[4]arenebenzocrown-6 compound. These forward extraction cesium distribution ratios are between approximately 3 times and approximately 4 times higher than those of BOBCalixC6 at its maximum solubility concentration of 0.007 M in the FPEX I process solvent. However, maximizing the forward extraction distribution ratios for cesium and strontium is not the only consideration because high forward extraction distribution ratios may adversely affect the ability to strip the radionuclides from the mixed extractant solvent. The increased solubility of the dialkyloxycalix[4]arenebenzocrown-6 compound in the mixed extractant solvent may provide increased cesium loading per extraction contact. The increased solubility of the dialkyloxycalix[4]arenebenzocrown-6 compounds may also enable use of weaker modifiers in the mixed extractant solvent or use of lower modifier concentrations in the mixed extractant solvent. Backward extraction (stripping of the cesium into dilute acid solution) has been found to be efficient at 0.025 M dialkyloxycalix[4]arenebenzocrown-6 compound, which is between approximately 3 times and approximately 4 times higher than that of BOBCalixC6 in the FPEX I process solvent.

The increased chemical stability of the dialkyloxycalix[4]arenebenzocrown-6 compound and the alcohol modifier over a wide range of nitric acid concentrations may enable the mixed extractant solvent to be used to remove cesium and strontium from feedstocks or aqueous feeds having a nitric acid concentration of up to approximately 5 M, such as from approximately 0.001 M to approximately 5 M. Since dissolved spent nuclear fuel typically includes a nitric acid concentration within this range, the mixed extractant solvent may be used to effectively remove cesium and strontium from dissolved spent nuclear fuel solutions. For instance, the mixed extractant solvent may be used to remove cesium and strontium from an aqueous feed having from approximately 2 M to approximately 5 M nitric acid. By removing the radionuclides, the mixed extractant solvent may be used to lower the radioactive waste volume and heat load of the aqueous feed. In addition, the radionuclides and the mixed extractant solvent may be recovered and the mixed extractant solvent may be recycled. The extraction method of the present invention may also produce less secondary waste than in conventional techniques. Furthermore, since the cesium and strontium are removed simultaneously, the extraction system of the present invention may be advantageous over conventional techniques, which require multiple, separate steps to remove the cesium and strontium.

The mixed extractant solvent may be used to selectively extract cesium and strontium over additional components in the aqueous feed. In addition to cesium and strontium, the aqueous feed may include other ions or radioactive elements. Typical components of dissolved spent nuclear fuel solutions are shown in Table 1. Simulant compositions having various combinations of the components shown in Table 1 may be prepared to test the efficacy of the mixed extractant solvent to selectively extract cesium and strontium.

TABLE 1

Typical Major Components Of Dissolved, High Burn-Up Spent Nuclear Fuel Solutions.

| Component | Amount | Component | Amount |
|---|---|---|---|
| Acid (M) | 0.8 | Pr g/l | 0.63 |
| Tc g/l | 0.41 | Nd g/l | 2.34 |
| Ba g/l | 1.59 | Zr g/l | 0.42 |
| Ce g/l | 1.37 | Sm g/l | 0.47 |
| Cs g/l | 1.43 | Np g/l | 0.43 |
| La g/l | 0.70 | Pu g/l | 4.76 |
| Pd g/l | 1.03 | Am g/l | 0.62 |
| Mo g/l | 2.09 | Sn g/l | 1.39 |
| Sr g/l | 0.44 | Rb g/l | 0.20 |

The cesium and strontium may be removed or forward extracted from the aqueous feed by combining the aqueous feed with the mixed extractant solvent. As used herein, the terms "forward extract," "forward extracted," "forward extraction," or grammatical equivalents thereof refer to removing or extracting the cesium and strontium from the first aqueous phase of the first extraction system. The first extraction system may include the aqueous feed (the first aqueous phase) and the mixed extractant solvent (the first organic phase). Before contacting the mixed extractant solvent and the aqueous feed, the aqueous feed may, optionally, be processed to remove additional ions and radioactive elements before the cesium and strontium are removed by the method of the present invention. The additional ions and radioactive elements may be removed by exposure to conventional extraction processes.

The first organic phase and the first aqueous phase may be contacted with one another and agitated to extract the cesium and strontium into the first organic phase. The distribution of the cesium and strontium between the first organic phase and the first aqueous phase may heavily favor the first organic phase. The first aqueous phase (aqueous feed) may be agitated with the first organic phase (mixed extractant solvent) for an amount of time sufficient to form complexes between the cesium and strontium and the extractants. For instance, complexes may be formed between the cesium and the dialkyloxycalix[4]arenebenzocrown-6 compound and between the strontium and the crown ether compound. The cesium and strontium may be present in the first organic phase while the first aqueous phase may be substantially depleted of cesium and strontium. The first aqueous phase may include other ions or radioactive elements that were present in the aqueous feed. The first organic phase and the first aqueous phase may then be separated by conventional techniques, such as liquid-liquid separation techniques, effectively removing the cesium and strontium from the aqueous feed.

The distribution of cesium and strontium between the first organic phase (the mixed extractant solvent including the dialkyloxycalix[4]arenebenzocrown-6 compound) and the first aqueous phase (aqueous feed) may be determined by conventional techniques. The distribution ratio for strontium ("$D_{Sr}$") may be calculated as the ratio of organic phase activity to the aqueous phase activity at equilibrium. High values for the $D_{Sr}$ indicate that the strontium is present predominantly in the organic phase while low values for the $D_{Sr}$ indicate that the strontium is present predominantly in the aqueous phase. Similarly, the distribution ratio for cesium ("$D_{Cs}$") may be calculated as the ratio of organic phase activity to the aqueous phase activity at equilibrium. High values for the $D_{Cs}$ indicate that the cesium is present predominantly in the organic phase while low values for the $D_{Cs}$ indicate that the cesium is present predominantly in the aqueous phase.

Once separated, the first organic phase and the first aqueous phase may be further processed. For instance, the first aqueous phase may be extracted multiple times with an additional volume of the mixed extractant solvent to remove substantially all of the cesium and strontium. The first aqueous phase may also be further extracted to remove the additional ions or radioactive elements that may have been present in the aqueous feed, such as by using conventional techniques. The radionuclides may be stripped or backward extracted from the first organic phase using a second aqueous phase or stripping solution to recover the cesium, strontium, and the mixed extractant solvent. As used herein, the terms "backward extract," "backward extracted," "backward extraction," or grammatical equivalents thereof refer to removing the cesium and strontium from the first organic phase. During recovery and recycling conditions, the distribution of the cesium and strontium between the first organic phase and the second aqueous phase may heavily favor the second aqueous phase. The cesium and strontium may be removed from the first organic phase by contacting and agitating the first organic phase with the second aqueous phase. The second aqueous phase and the first organic phase may form a second extraction system. The second aqueous phase may be a dilute acidic solution, such as a nitric acid solution having from approximately 0.001 M $HNO_3$ to approximately 0.5 M $HNO_3$. In one embodiment, the second aqueous phase includes 0.01 M $HNO_3$. In addition, water or other dilute mineral acids may be used as the second aqueous phase to backward extract the cesium and strontium from the first organic phase.

The first organic phase may be mixed with the second aqueous phase for an amount of time sufficient for the cesium and strontium ions to dissociate from the complexes of the cesium and strontium with the extractants. Once dissociated, the cesium and strontium may distribute into the second aqueous phase. The second aqueous phase, having substantially all of the cesium and strontium, may be separated from the first organic phase, which is substantially depleted of cesium and strontium. The radionuclides in the second aqueous phase may then be used or stored. For instance, the cesium and strontium may be solidified for storage. Alternatively, the recovered cesium and strontium may be used as gamma sources, beta sources, or heat sources. The recovered mixed extractant solvent may be reused or recycled into subsequent extractions.

To achieve optimal extraction and recovery of the radionuclides from the aqueous feed, the cesium and strontium may have relatively high distribution ratios when extracted at a $HNO_3$ concentration of from approximately 1 M $HNO_3$ to approximately 3 M $HNO_3$ and when backward extracted at a $HNO_3$ concentration of from approximately 0.01 M $HNO_3$ to approximately 0.3 M $HNO_3$.

The forward extraction and backward extraction (recovery) of the cesium and strontium may be performed at a temperature ranging from approximately 1° C. to approximately 40° C. To provide optimal extraction of the cesium and strontium, the forward extraction may be conducted at low temperatures within this range, such as at a temperature ranging from approximately 10° C. to approximately 15° C. However, the forward extraction may also be conducted at ambient temperature, such as from approximately 20° C. to approximately 25° C. The backward extraction of the cesium and strontium may be conducted at a wider range of temperatures, such as from approximately 10° C. to approximately 60° C. For instance, the backward extraction may be performed at a temperature ranging from approximately 20° C. to approximately 40° C.

The following examples serve to explain embodiments of the present invention in more detail. These examples are not to be construed as being exhaustive or exclusive as to the scope of this invention.

EXAMPLES

All solvents used in the extraction process were reagent grade and were used as received. Deionized water was used to prepare all aqueous solutions. Reagent grade nitric acid was obtained from Aldrich Chemical Co. (Milwaukee, Wis.). ISOPAR® L was obtained from Exxon Mobil Chemical Company (Houston, Tex.). $^{85}$Sr and $^{137}$Cs radiotracers used for the radiotracer studies were obtained as $^{85}$SrCl$_2$ in 1 M HCl and $^{137}$CsCl in 1 M HCl from Isotope Products (Burbank, Calif.). DtBuCH18C6 was purchased from Eichrom Industries, Inc. (Darien, Ill.). BOBCalixC6 and Cs-7SB were received from Marshallton Research Laboratories (King, N.C.).

The aqueous feed simulant composition used in this testing was based on a typical composition expected for leaching of spent light water reactor ("LWR") fuel with nitric acid. It was also assumed that a process to separate uranium from the spent LWR would precede removal of the cesium and strontium. Therefore, it was assumed that the aqueous feed simulant composition did not contain uranium. The components of the aqueous feed simulant composition are provided in Table 2.

TABLE 2

Composition Of 1 M Aqueous Feed Simulant.

| Component | Simulant (M) |
| --- | --- |
| H$^+$ | 1.0 to 2.0 |
| Sr | 2.0E−03 |
| Cs | 4.1E−03 |
| Zr | 1.1E−02 |
| Ba | 3.7E−03 |
| La | 2.2E−03 |
| Ce | 4.3E−03 |
| Nd | 7.2E−03 |
| Sm | 5.0E−03 |
| Gd | 2.6E−04 |
| Eu | 1.4E−04 |
| Y | 1.4E−03 |
| Rb | 1.0E−03 |

Distribution ratios ($D_M=[M]_{org}/[M]_{aq}$) were measured by equilibrium batch contacts between the organic and aqueous phases at an organic-to-aqueous phase ratio (O/A) of unity (O/A=1). All distribution ratio measurements were conducted in a temperature controlled water bath at 25±1° C. The aqueous phase was of the appropriate HNO$_3$ concentration, to which trace quantities (typically, less than 10$^{-7}$ M each) of the major radionuclides of interest ($^{137}$Cs, $^{85}$Sr, $^{154}$Eu, or $^{241}$Am) were added. The organic and aqueous phases were contacted by vortex mixing for 1 minute. All batch contact experiments were performed at ambient temperature (from approximately 20° C. to approximately 25° C.) unless otherwise noted. Following extraction, the samples were centrifuged for 1 minute and the organic and aqueous phases separated by pipet or centrifugation. The distribution ratios (D$_{Sr}$, or D$_{Cs}$) were calculated as the ratio of the appropriate specific activities in the organic and aqueous phases as determined by γ-ray counting (gamma spectroscopy). The counting time was selected to provide less than approximately 1% statistical uncertainty. The means of triplicate measurements had a maximum relative standard deviation of ±5%, and mass balance analyses were performed for which the acceptance criterion was 100±5%.

Comparative Example 1

Preparation Of FPEX I Process Solvent

A FPEX I process solvent including 0.007 M BOB-CalixC6, 0.075 M DtBuCH18C6, 0.75 M Cs-7SB modifier, and 0.003 M TOA in ISOPAR® L was prepared by combining the BOBCalixC6, DtBuCH18C6, Cs-7SB modifier, and TOA in the ISOPAR® L.

Example 2

Preparation Of Dialkyloxycalix[4]Arenebenzocrown-6 Compounds

MC-8, MC-10, MC-12, MC-8B, MC-10B, and MC-12-B were prepared by a method similar to that described in Sachleben et al., "Surveying the Extraction of Cesium Nitrate by 1,3-Alternate Calix[4]Arene Crown-6 Ethers in 1,2-Dichloroethane," *Solv. Extr. Ion Exch.,* 17(6): 1445-1459 (1999). All reagents were obtained from commercial suppliers. To produce the dialkyloxycalix[4]arenebenzocrown-6 compounds, commercially available alcohols or alkyl bromides corresponding to the alkyl portion to be added to calix [4]arene were transformed into corresponding alkyl tosylates or iodides by known methods, such as those described in Ouchi et al., "Convenient and Efficient Tosylation of Oligoethylene Glycols and the Related Alcohols in Tetrahydrofuran-Water in the Presence of Sodium Hydroxide," *Bull. Chem. Soc. Jpn.,* 63(4), 1260-1262 (1990) and Casnati et al., "Synthesis, Complexation, and Membrane Transport Studies of 1,3-Alternate Calix[4]arene-crown 6 Conformers: A New Class of Cesium Selective Ionophores," *J. Am. Chem. Soc.,* 117(10): 2767-2777 (1995), respectively. The resultant alkylating agents were reacted with calix[4]arene and potassium carbonate in acetonitrile at reflux to provide 55%-85% yields of 25,27-di(alkyloxy)calix[4]arene compounds in the cone conformation. These diphenolic intermediates were reacted with the ditosylate of bis-1,2[2'(2")-hydroxyethoxy)ethoxy] benzene, as described in Kyba et al., "Host-Guest Complexation. 1. Concept and Illustration," *J. Am. Chem. Soc.,* 99(8): 2564-2571 (1977), and cesium carbonate in acetonitrile at reflux to afford the 1,3 alternate-25,27-di(alkyloxy)calix[4] arenebenzocrown-6 compounds in 60%-85% yields. The structures of MC-8B, MC-10, MC-10B, MC-12, and MC-12B were verified by combustion analysis, $^1$H and $^{13}$C nuclear magnetic resonance spectroscopy, and infrared spectroscopy.

Example 3

Preparation Of Cs-5SB

Cs-5SB was prepared in two steps from 4-sec-butylphenol. First, 3-[4-(sec-butyl)phenoxy]-2-methyl-1-propene was prepared by reacting 4-sec-butylphenol with 3-chloro-2-methylpropene and two equivalents of potassium carbonate in dry acetonitrile at 75° C. The 3-[4-(sec-butyl)phenoxy]-2-methyl-1-propene was reduced to the corresponding alcohol by hydroboration. The hydroboration included overnight reaction with approximately one-third molar equivalent of $BH_3.THF$, followed by treatment with a 3 M NaOH solution and a 30% hydrogen peroxide solution, and refluxing of the mixture overnight. Upon cooling, the mixture separated into organic and aqueous layers. The organic phase was collected, and the aqueous phase saturated with potassium bicarbonate and washed with ethyl ether. The ethyl ether washings were combined with the separated organic phase, washed with saturated NaCl, and dried using anhydrous $Na_2SO_4$. The solvents were removed and the oily residue fractionally distilled under vacuum to afford Cs-5SB at a purity of greater than or equal to approximately 98% and a yield of greater than approximately 75%.

Example 4

Preparation Of Mixed Extraction Solvents Including Dialkyloxycalix[4]Arenebenzocrown-6 Compounds Or BOBCalixC6

The dialkyloxycalix[4]arenebenzocrown-6 compounds (MC-8, MC-8B, MC-10, MC-10B, MC-12, or MC-12B) described in Example 2 or BOBCalixC6 were formulated into individual mixed extractant solvents by combining the DtBuCH18C6, modifier, any optional ingredients, and the ISOPAR® L with the respective dialkyloxycalix[4]arenebenzocrown-6 compound or BOBCalixC6. To enable direct comparison of the extractant abilities of the resulting mixed extractant solvents and the FPEX I process solvent, the mixed extractant solvents included an equal amount of the dialkyloxycalix[4]arenebenzocrown-6 compound. As such, each of the mixed extraction solvents included 0.007 M of the respective dialkyloxycalix[4]arenebenzocrown-6 compound, 0.075 M DtBuCH18C6, 0.75 M Cs-7SB modifier, and 0.003 M TOA in ISOPAR® L. Each of the mixed extractant solvents was prepared by combining the respective dialkyloxycalix[4]arenebenzocrown-6 compound, the DtBuCH18C6, the modifier, and the TOA with the ISOPAR® L.

Example 5

Cesium And Strontium Extraction Performance Of The Mixed Extractant Solvents

Mixed extractant solvents including 0.007 M of the respective dialkyloxycalix[4]arenebenzocrown-6 compound (MC-8, MC-8B, MC-10, MC-10B, MC-12, or MC-12B), 0.075 M DtBuCH18C6, 0.75 M Cs-7SB modifier, and 0.003 M TOA in ISOPAR® L were evaluated for their respective abilities to simultaneously extract cesium and strontium from the aqueous feed simulant composition described in Table 2. The cesium and strontium distribution ratios of the mixed extraction solvents were compared to those of the FPEX I process solvent. The cesium extraction performance and strontium extraction performance of each of the mixed extractant solvents was determined using the batch contact flowsheet presented in FIG. 1, where "E1," "E2," and "E3" refer to three forward extraction acts: a first extraction act, a second extraction act, and a third extraction act, respectively, and "St1" and "St2" refer to two backward extraction acts: a first strip act and a second strip act, respectively. For the E1, E2, and E3 extractions, the aqueous feed 2 (1.5 M $HNO_3$) described in Table 2 was contacted and mixed with the mixed extractant solvents 4. The aqueous feed 2 and the mixed extractant solvent 4 were combined in a vessel 6 to conduct the extraction. Two phases were formed during the extraction: the first organic phase and the first aqueous phase, with the cesium and strontium substantially distributed in the first organic phase.

The cesium and strontium distribution ratios for the mixed extractant solvents 4 were calculated for the first organic phase and are reported in Tables 3 and 4, respectively, as E1, along with the cesium and strontium distribution ratios for the FPEX I process solvent. The cesium and strontium were stripped from the first (and subsequent) organic phase to recover these radionuclides. For the strips or backward extractions, the first (and subsequent) organic phase was contacted with dilute acidic solution 8, which was 0.01 M $HNO_3$. The cesium and strontium distribution ratios for the backward extractions were calculated and are reported in Tables 3 and 4 as St1, along with the cesium and strontium distribution ratios for the FPEX I process solvent. The first aqueous phase was subsequently extracted two more times (E2 and E3) with an additional volume of the mixed extractant solvent 4. Cesium and strontium distribution ratios were calculated for the subsequently formed organic phases and are reported in Tables 3 and 4 as E2 and E3, respectively. The cesium and strontium distribution ratios for the subsequent aqueous phase were calculated and are reported in Tables 3 and 4 as St2. The first, second, and third extractions were conducted at 25° C. and the first and second strips were conducted at 35° C.

TABLE 3

Cesium Forward And Backward Distribution Ratios From A 1.5 M $HNO_3$ Feed.

| Contact | MC-8 | MC-8B | MC-10 | MC-10B | MC-12 | MC-12B | FPEX I |
|---------|------|-------|-------|--------|-------|--------|--------|
| E1  | 4.2 | 1.4 | 3.7 | 3.7 | 2.9 | 2.5 | 5.6 |
| E2  | 1.9 | 1.1 | 2.0 | 1.9 | 1.7 | 1.3 | 2.6 |
| E3  | 1.5 | 1.0 | 1.6 | 1.5 | 1.3 | 1.1 | 1.8 |
| St1 | 0.6 | 0.2 | 0.5 | 0.5 | 0.4 | 0.4 | 0.8 |
| St2 | 0.2 | 0.1 | 0.2 | 0.2 | 0.2 | 0.2 | 0.4 |

TABLE 4

Strontium Forward And Backward Distribution Ratios From A 1.5 M $HNO_3$ Feed.

| Contact | MC-8 | MC-8B | MC-10 | MC-10B | MC-12 | MC-12B | FPEX I |
|---------|------|-------|-------|--------|-------|--------|--------|
| E1  | 10.5 | 8.9  | 9.5  | 9.6  | 7.7  | 7.7  | 9.8  |
| E2  | 8.6  | 8.3  | 8.4  | 8.6  | 7.5  | 6.7  | 8.9  |
| E3  | 8.5  | 8.1  | 8.3  | 8.3  | 7.0  | 6.3  | 8.3  |
| St1 | 0.06 | 0.06 | 0.06 | 0.06 | 0.04 | 0.03 | 0.06 |
| St2 | 0.01 | 0.01 | 0.01 | 0.01 | 0.01 | 0.02 | 0.01 |

The cesium distribution ratios varied slightly depending on the dialkyloxycalix[4]arenebenzocrown-6 compound (MC-8, MC-8B, MC-10, MC-10B, MC-12, or MC-12B) used in the mixed extractant solvent, with the lowest distribution ratios obtained for MC-8B. At a concentration of 0.007 M, the dialkyloxycalix[4]arenebenzocrown-6 compounds in the mixed extractant solvents had lower cesium distribution ratios than BOBCalixC6 in the FPEX I process solvent. However, since the dialkyloxycalix[4]arenebenzocrown-6 compounds were determined to be more soluble in ISOPAR® L than BOBCalixC6, the increased solubility enables higher mass levels of cesium extraction and higher forward distribution ratios than those obtainable with the FPEX I process solvent. Therefore, while the cesium distribution ratios measured for the mixed extractant solvents were lower than those for the FPEX I process solvent, the cesium distribution ratios indicated that desirable process performance is achievable by increasing the concentration of the dialkyloxycalix[4]arenebenzocrown-6 compounds in the mixed extractant solvent.

The strontium distribution ratios varied slightly depending on the dialkyloxycalix[4]arenebenzocrown-6 compound (MC-8, MC-8B, MC-10, MC-10B, MC-12, or MC-12B) used in the mixed extractant solvent, likely due to small variations in the solvent composition. In general, the strontium distribution ratios for the mixed extractant solvents were comparable to those obtained for the FPEX I process solvent.

Example 6

Cesium And Strontium Extractant Performance Of MC-8

To determine the extractant performance of MC-8 at higher concentrations and to determine the cesium distribution ratios as a function of temperature and acidity, testing with MC-8 was performed to determine if its solubility in the mixed extractant solvent was increased compared to that of BOBCalixC6 in the FPEX I process solvent. MC-8 was selected for these tests because a greater quantity of this dialkyloxycalix[4]arenebenzocrown-6 compound was synthesized and available for testing.

The concentration of MC-8 was varied from 0.01 M to 0.05 M to determine its solubility in 0.075 M DtBuCH18C6, 0.75 M Cs-7SB modifier, and 0.003 M TOA in ISOPAR® L and to determine the resulting cesium and strontium distribution ratios. MC-8 was found to be soluble at these increased concentrations, which is a significant improvement over the solubility of BOBCalixC6 in the FPEX I process solvent (0.007 M maximum concentration). The mixed extractant solvent containing 0.05 M MC-8 was monitored at room temperature for several months with no observable precipitation. Distribution ratios for cesium and strontium from 1.5 M $HNO_3$ as a function of MC-8 concentration are presented in Table 5.

TABLE 5

Cesium And Strontium Distribution Ratios At Varying MC-8 Concentrations.

| Conc. (M) | Contact | $D_{Sr}$ | $D_{Cs}$ |
|---|---|---|---|
| 0.010 | E1 | 8.9 | 7.2 |
| 0.015 | E1 | 7.2 | 13.3 |
| 0.020 | E1 | 9.4 | 21.5 |
| 0.025 | E1 | 9.1 | 29.4 |

The strontium distribution ratios remained approximately the same as those in Table 4, while the cesium distribution ratios increased from 7.2 at 0.01 M MC-8 to 29 at 0.05 M MC-8. In comparison, the cesium distribution ratio at 0.007 M MC-8 was 4.2.

Additional testing was performed with 0.025 M MC-8 in 0.075 M DtBuCH18C6, 0.75 M Cs-7SB modifier, and 0.003 M TOA in ISOPAR® L to determine the cesium and strontium extraction distribution ratios as a function of temperature. The resulting cesium and strontium extraction distribution ratios from a 1.0 M $HNO_3$ aqueous feed are presented in Table 6.

TABLE 6

Cesium And Strontium Distribution Ratios As A Function Of Temperature.

| Temp. (° C.) | Contact | $D_{Sr}$ | $D_{Cs}$ |
|---|---|---|---|
| 15 | E1 | 9.0 | 44.5 |
| 20 | E1 | 6.0 | 24.5 |
| 25 | E1 | 4.6 | 15.7 |
| 30 | E1 | 3.4 | 9.9 |
| 35 | E1 | 2.5 | 6.2 |

As shown in Table 6, the cesium and strontium distribution ratios decreased with increasing temperature.

Cesium and strontium distribution ratios were also measured for MC-8 as a function of $HNO_3$ concentration (from 1.0 M to 4.0 M) at 20° C. with 0.025 M MC-8 in 0.075 M DtBuCH18C6, 0.75 M Cs-7SB modifier, and 0.003 M TOA in ISOPAR® L. Results of these tests are presented in Table 7.

TABLE 7

Cesium And Strontium Distribution Ratios As A Function Of $HNO_3$ Concentration.

| $HNO_3$ Conc. (M) | Contact | $D_{Sr}$ | $D_{Cs}$ |
|---|---|---|---|
| 1.0 | E1 | 7.4 | 31.0 |
| 1.5 | E1 | 12.4 | 35.6 |
| 2.0 | E1 | 16.2 | 39.9 |
| 3.0 | E1 | $3^{rd}$ phase | $3^{rd}$ phase |
| 4.0 | E1 | $3^{rd}$ phase | $3^{rd}$ phase |

The cesium and strontium distribution ratios increased with increasing $HNO_3$ concentration up to 2.0 M $HNO_3$. At 3.0 M and 4.0 M $HNO_3$, third phase formation was observed, which is indicated in Table 7 by the label "$3^{rd}$ phase." These results are consistent with results (not shown) obtained with the FPEX I process solvent.

The batch contact flowsheet test shown in FIG. 1 was performed for 0.025 M MC-8 using a simulated feed with the composition listed in Table 2 and an acidity of 1.0 M $HNO_3$. Cesium and strontium distribution ratios for this test are presented in Table 8.

TABLE 8

Cesium And Strontium Forward And Backward Distribution Ratios.

| Contact | $D_{Sr}$ | $D_{Cs}$ |
|---|---|---|
| E1 | 7.1 | 34.7 |
| E2 | 6.2 | 29.0 |
| E3 | 6.2 | 21.9 |
| St1 | 0.022 | 0.63 |
| St2 | 0.006 | 0.25 |

The extraction distribution ratios for cesium are greatly increased from those obtained with the FPEX I process solvent (see Tables 3 and 4 for FPEX I process solvent distribution ratios).

Example 7

Stability Of The Mixed Extractant Solvents Prepared Using Dialkyloxycalix[4]Arenebenzocrown-6 Based Solvents The stability of the mixed extractant solvents prepared using dialkyloxycalix[4]arenebenzocrown-6 compounds (MC-8, MC-8B, MC-10, MC-10B, MC-12, or MC-12B) relative to BOBCalixC6 in the FPEX I process solvent was determined. Samples were prepared using each of the dialkyloxycalix[4]arenebenzocrown-6 compounds and contacted with 1.5 M $HNO_3$. The samples included 0.007 M of the respective dialkyloxycalix[4]arenebenzo-crown-6 compound (MC-8, MC-8B, MC-10, MC-10B, MC-12, or MC-12B), 0.075 M DtBuCH18C6, 0.75 M Cs-7SB modifier, and 0.003 M TOA in ISOPAR® L. The stability of the dialkyloxycalix[4]arenebenzocrown-6 based solvents was evaluated by measuring the cesium and strontium distribution ratios as a function of contact time. These cesium and strontium distribution ratios for the mixed extractant solvents are presented in Table 9 and Table 10, respectively, along with the cesium and strontium distribution ratios for the FPEX I process solvent. The symbol "-" is used in Tables 9 and 10 to indicate no data was collected.

TABLE 9

Cesium Distribution Ratios As A Function Of Contact Time.

| Contact time, days | MC-8 | MC-8B | MC-10 | MC-10B | MC-12 | MC-12B | FPEX I |
|---|---|---|---|---|---|---|---|
| 0 | 4.2 | 1.36 | 3.7 | 3.7 | 3.0 | 3.3 | 5.9 |
| 34 | 3.2 | 0.8 | 3.0 | 3.0 | — | — | — |
| 36 | — | — | — | — | 2.5 | 2.1 | 5.8 |
| 70 | 3.6 | 1.5 | 3.5 | 3.4 | — | — | 4.7 |
| 244 | — | — | — | — | 2.2 | 1.8 | — |
| 278 | 2.8 | 2.8 | 1.1 | 2.8 | 2.8 | — | 3.6 |

TABLE 10

Strontium Distribution Ratios As A Function Of Contact Time.

| Contact time, days | MC-8 | MC-8B | MC-10 | MC-10B | MC-12 | MC-12B | FPEX I |
|---|---|---|---|---|---|---|---|
| 0 | 10.5 | 8.9 | 9.5 | 9.6 | 7.5 | 6.3 | 10.2 |
| 34 | 7.7 | 7.2 | 7.7 | 8.5 | — | — | 10.0 |
| 36 | — | — | — | — | 7.1 | 6.9 | — |
| 70 | 9.3 | 9.3 | 9.0 | 9.5 | — | — | 8.9 |
| 244 | — | — | — | — | 6.1 | 5.7 | — |
| 278 | 8.0 | 7.6 | 7.7 | 8.0 | — | — | 7.8 |

The FPEX I process solvent showed a decrease in cesium and strontium distribution ratios following prolonged contact with 1.5 M $HNO_3$. The long-term decrease in the cesium and strontium distribution ratios using the FPEX I process solvent after 278 days contact with $HNO_3$ indicates that the FPEX I process solvent is degraded to some extent. This degradation is likely due to chemical attack or nitration of the BOBCalixC6 in the FPEX I process solvent. The data presented in Tables 9 and 10 for the mixed extractant solvents including the dialkyloxycalix[4]arenebenzocrown-6 compounds also showed hydrolytic degradation or nitration. However, it is difficult to compare the relative extents of degradation. In order to compare the different extractants, the distribution ratio data presented in Tables 9 and 10 were normalized to the values obtained at t=0 days contact. The normalized cesium and strontium distribution ratios for the FPEX I process solvent and the mixed extractant solvents as a function of contact time are presented in FIGS. 2 and 3, respectively.

Figure 2:
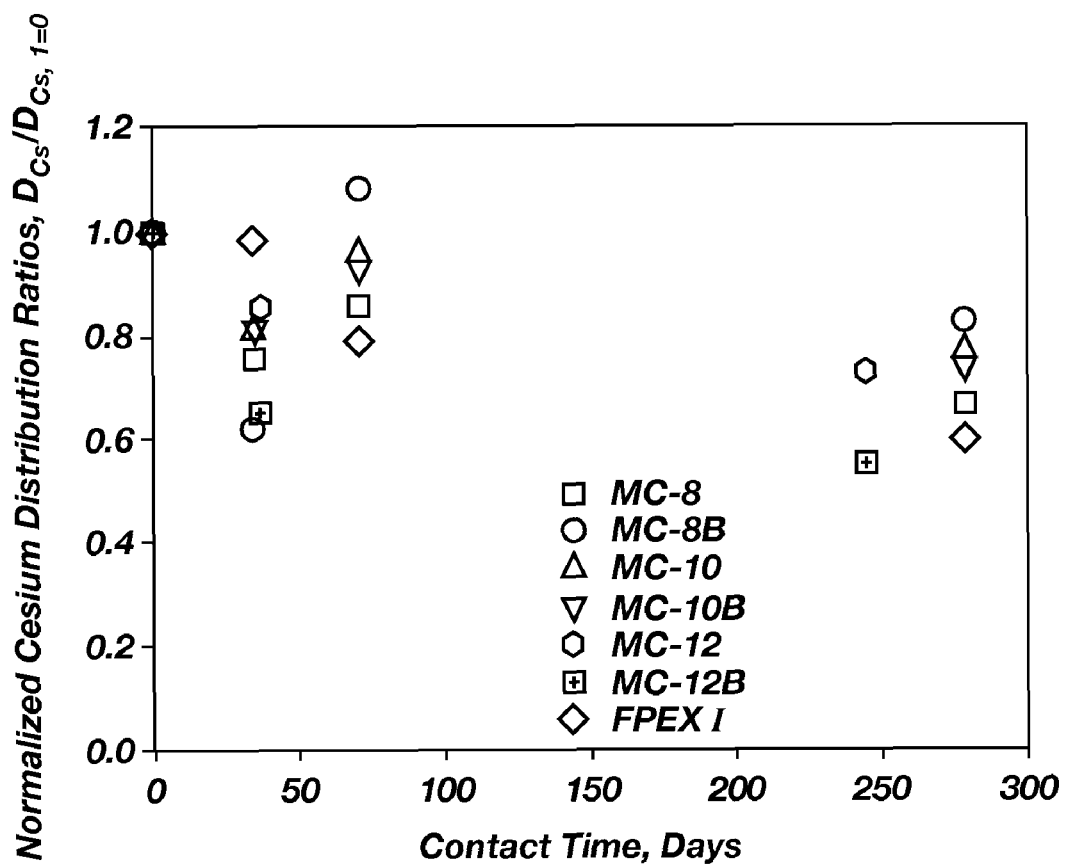
FIG. 2 shows normalized cesium distribution ratios as a function of contact time with 1.5 M $HNO_3$ for mixed extractant solvents according to an embodiment of the present invention.

The data presented in FIG. 2 shows that, with the exception of MC-12B, the amount of decrease in the normalized cesium distribution ratios for each of the mixed extractant solvents is less than that observed for the FPEX I process solvent. Assuming that the observed decreases in the distribution ratios are indicative of extractant degradation, the dialkyloxycalix[4]arenebenzocrown-6 compounds appear to be more stable towards hydrolytic attack than BOBCalixC6. Therefore, the mixed extractant solvents prepared with the dialkyloxycalix[4]arenebenzocrown-6 compounds are more stable than the FPEX I process solvent to contact with acidic conditions for longer periods of time. MC-8B appears to be the most resistant toward hydrolytic degradation. The MC-10 and MC-10B exhibit similar stabilities.

Figure 3:
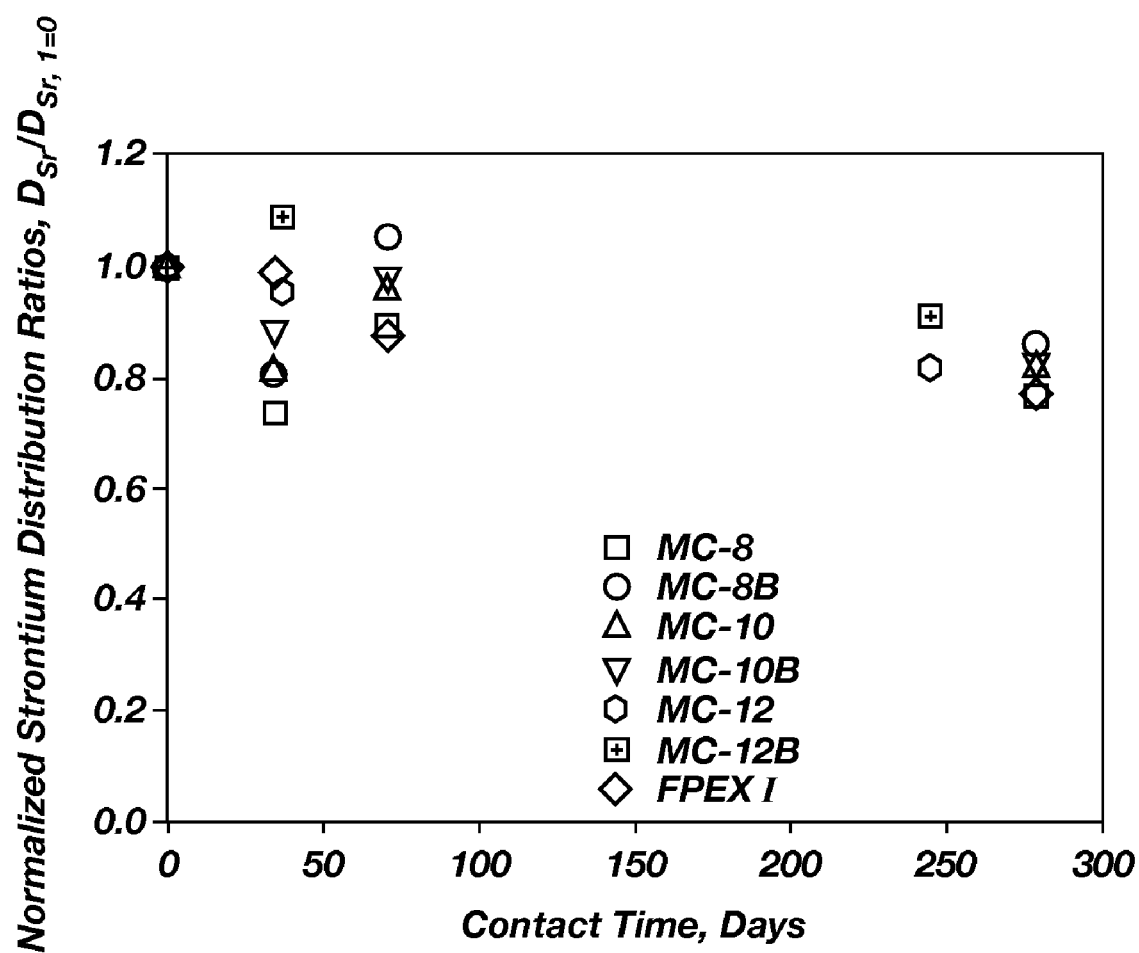
FIG. 3 shows normalized strontium distribution ratios as a function of contact time with 1.5 M $HNO_3$ for mixed extractant solvents according to an embodiment of the present invention.

The data presented in FIG. 3 shows the normalized distribution ratios for the extraction of strontium by DtBuCH18C6 as a function of contact time. As shown in FIG. 3, the DtBuCH18C6 appears to be subject to degradation following prolonged contact with $HNO_3$. However, since the DtBuCH18C6 concentration used in the mixed extractant solvents is not solubility controlled, losses due to extractant degradation are easily overcome by increasing the initial DtBuCH18C6 concentration.

Example 8

Cesium And Strontium Extractant Performance Of MC-10B

To select a dialkyloxycalix[4]arenebenzocrown-6 compound as a replacement for BOBCalixC6, multiple factors, such as the data presented in Examples 5-7 and the synthetic challenges presented by each dialkyloxycalix[4]arenebenzocrown-6 compound (availability of precursor materials, overall yield, ease of scale-up, etc.), were evaluated. MC-10B was determined to exhibit the best combination of favorable characteristics (synthetic, extraction behavior, stability) to improve the overall performance of the FPEX I solvent extraction process and, therefore, was chosen for further testing and development. MC-8 and MC-10 were also determined to exhibit favorable characteristics and may be viable alternatives to MC-10B.

Figure 4:
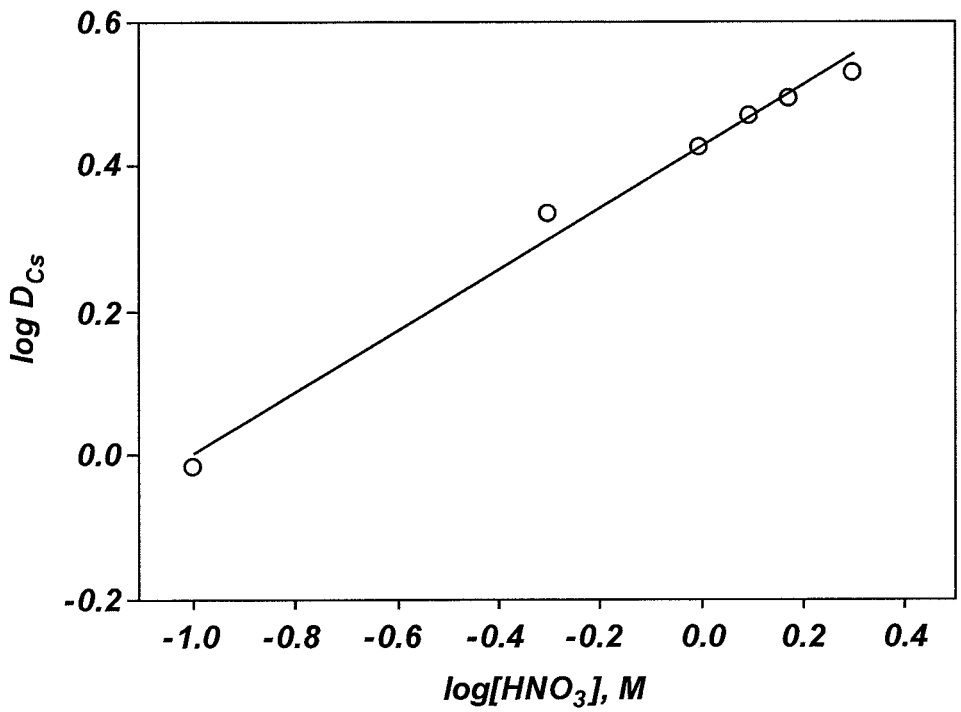
FIG. 4 shows cesium distribution ratios as a function of $HNO_3$ concentration for a mixed extractant solvent including MC-10B.

The extraction performance and third phase formation behavior of MC-10B was evaluated by measuring cesium and strontium distribution ratios as a function of $HNO_3$ concentration using a mixed extractant solvent of 0.007 M MC-10B, 0.075 M DtBuCH18C6, and 0.75 M Cs-7SB modifier dissolved in ISOPAR® L. TOA was not utilized in this mixed extractant solvent because preliminary data indicate that TOA is not necessary for efficient stripping of cesium from the loaded mixed extractant solvent. The $HNO_3$ dependency for $D_{Cs}$ (strontium distribution data is removed for clarity) using MC-10B is presented in FIG. 4. These experiments were performed using an aqueous phase containing carrier quantities of cesium nitrate (0.004 M) and strontium nitrate (0.002 M) and 1.0 M $HNO_3$. The data is not corrected for activity effects. The cesium distribution ratios exhibited the expected linear dependence on $HNO_3$ concentration and no formation of third phases was detected up to 2 M $HNO_3$.

Figure 5:
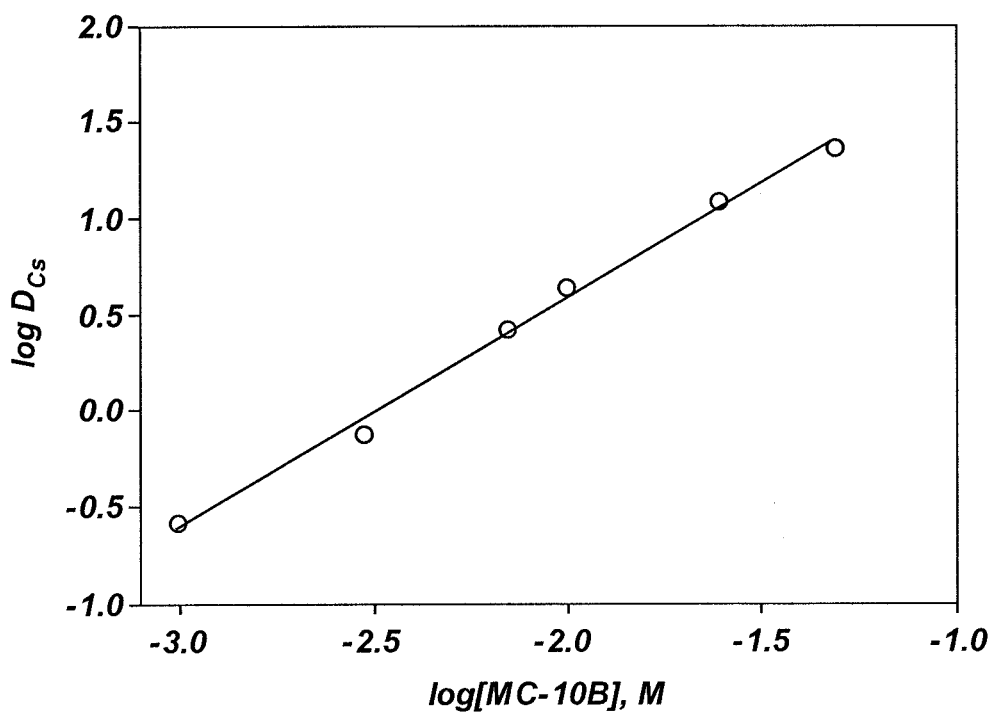
FIG. 5 shows cesium distribution ratios as a function of MC-10B concentration for a mixed extractant solvent including MC-10B.

The dependence of measured cesium distribution ratios on the concentration of MC-10B was also evaluated, as shown in FIG. 5. The mixed extractant solvents included a concentration of MC-10B ranging from 0.001 M to 0.050 M, 0.075 M DtBuCH18C6, and 0.75 M Cs-7SB modifier dissolved in ISOPAR® L. The upper concentration was set at 0.050 M MC-10B since $D_{Cs}$ values obtained at this concentration were significantly higher than required for the extraction process. The experiments were conducted using an aqueous feed containing carrier quantities of cesium nitrate (0.004 M) and strontium nitrate (0.002 M) and 1.0 M $HNO_3$. The MC-10B dependency for $D_{Cs}$ (strontium distribution data is removed for clarity) is presented in FIG. 5. The data is not corrected for activity effects. The measured $D_{Cs}$ values exhibited the expected linear dependence on the concentration of MC-10B.

Example 9

Cesium And Strontium Extractant Performance Of MC-10B And Cs-5,1-Octanol, Or EXXAL® 12

Figure 6:
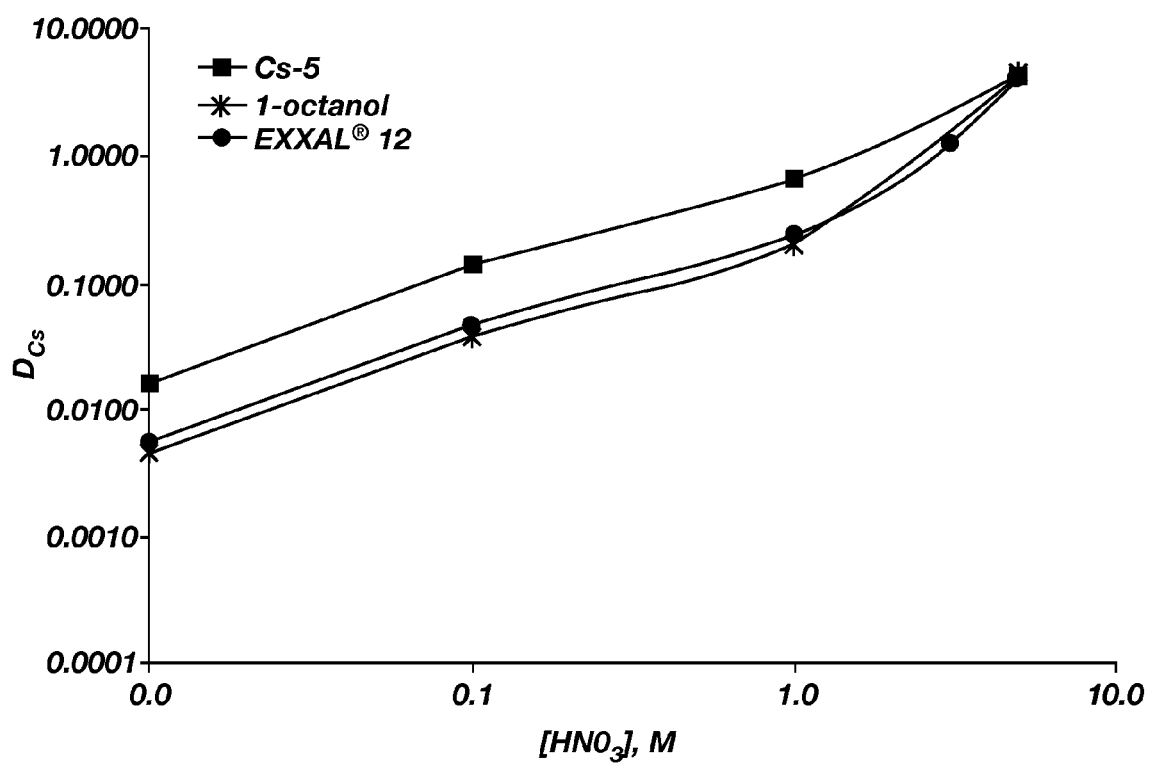
FIG. 6 shows cesium distribution ratios as a function of $HNO_3$ concentration for mixed extractant solvents including MC-10B or BOBCalixC6 as the extractant and Cs-5,1-octanol, or EXXAL® 12 as the modifier.

The extraction performance of MC-10B was evaluated by measuring cesium distribution ratios as a function of $HNO_3$ concentration using mixed extractant solvents of 0.007 M MC-10B, 0.075 M DtBuCH18C6, 0.003 M TOA, and 0.75 M alcohol modifier dissolved in ISOPAR® L. The alcohol modifier included Cs-5,1-octanol, or EXXAL® 12. The mixed extractant solvent including EXXAL® 12 utilized 0.007 M BOBCalixC6 instead of MC-10B. The aqueous feed included 0.0004 M cesium nitrate, 0.0004 M strontium nitrate, and varying concentrations of $HNO_3$ (0 M, 0.1 M, 1 M, or 5 M). The cesium distribution ratios are shown in FIG. 6.

Example 10

Cesium And Strontium Extractant Performance Of MC-10B And EXXAL® 12

Figure 7:
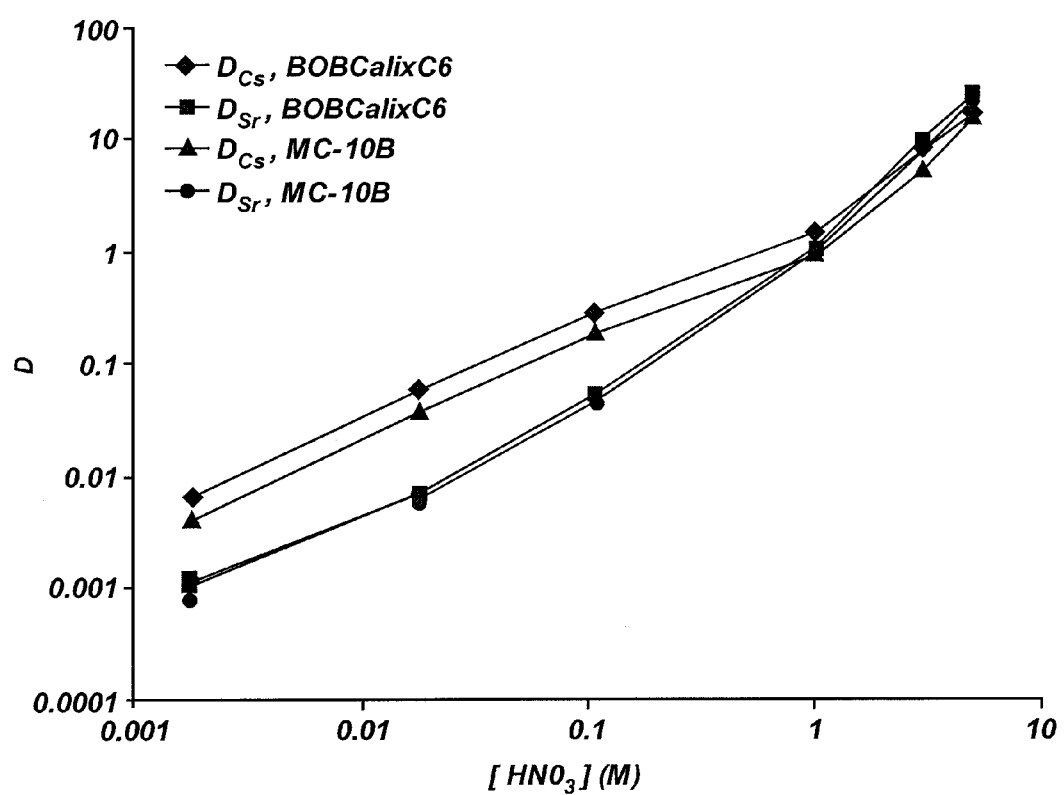
FIG. 7 shows cesium and strontium distribution ratios as a function of $HNO_3$ concentration for mixed extractant solvents including MC-10B or BOBCalixC6 as the extractant and EXXAL® 12 as the modifier.

The extraction performance of MC-10B was evaluated by measuring cesium and strontium distribution ratios as a function of $HNO_3$ concentration using a mixed extractant solvent of 0.025 M MC-10B, 0.150 M DtBuCH18C6, 0.003 M TOA, and 1.25 M EXXAL® 12 dissolved in ISOPAR® L. For comparison, cesium and strontium distribution ratios for an extractant solvent including 0.025 M BOBCalixC6, 0.150 M DtBuCH18C6, 0.003 M TOA, and 1.25 M EXXAL® 12 dissolved in ISOPAR® L were also measured. The aqueous feed included 0.004 M cesium nitrate, 0.002 M strontium nitrate, and varying concentrations of $HNO_3$ (0.003 M, 0.03 M, 0.1 M, 1 M, 5 M, or 8 M). As shown in FIG. 7, the cesium and strontium distribution ratios for the mixed extractant solvent including MC-10B and the solvent including BOB-CalixC6 were similar.

Figure 8:
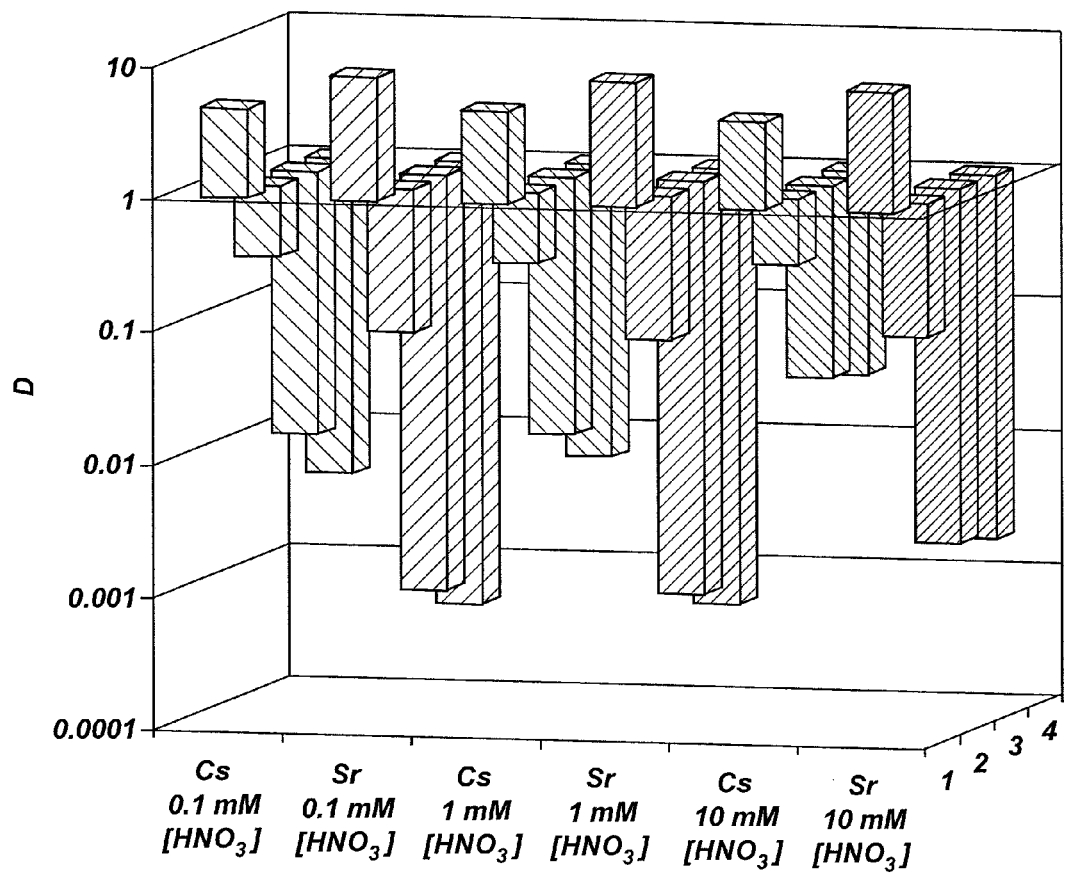
FIG. 8 shows cesium and strontium distribution ratios for the extraction and backward extraction using a mixed extractant solvent including MC-10B and EXXAL® 12.

The extraction and backward extraction performance of the above-mentioned mixed extractant solvent was evaluated to determine the effect of $HNO_3$ concentration on removing the radionuclides from the organic phase obtained from the forward extraction. The forward extraction was conducted using the mixed extractant solvent including 0.025 M MC-10B, 0.150 M DtBuCH18C6, 0.003 M TOA, and 1.25 M EXXAL® 12 dissolved in ISOPAR® L. The aqueous feed included 0.004 M cesium nitrate, 0.002 M strontium nitrate, and 3 M $HNO_3$. Stripping solutions used for the backward extraction were 0.1 mM $HNO_3$, 1 mM $HNO_3$, or 10 mM $HNO_3$. After the forward extraction, three consecutive backward extractions were conducted on the organic phase having the radionuclides using fresh volumes of the stripping solutions. The cesium and strontium distribution ratios for the forward and backward extractions are shown in FIG. 8. The cesium and strontium distribution ratios for the forward extraction are indicated by 1, while the cesium and strontium distribution ratios for the backward extractions are indicated by 2, 3, and 4. The cesium and strontium distribution ratios for the backward extractions indicate that the stripping solutions provided effective recovery of the radionuclides.

Example 11

Cesium And Strontium Extractant Performance Of MC-10B And 1-Decanol Or EXXAL® 10

Figure 9:
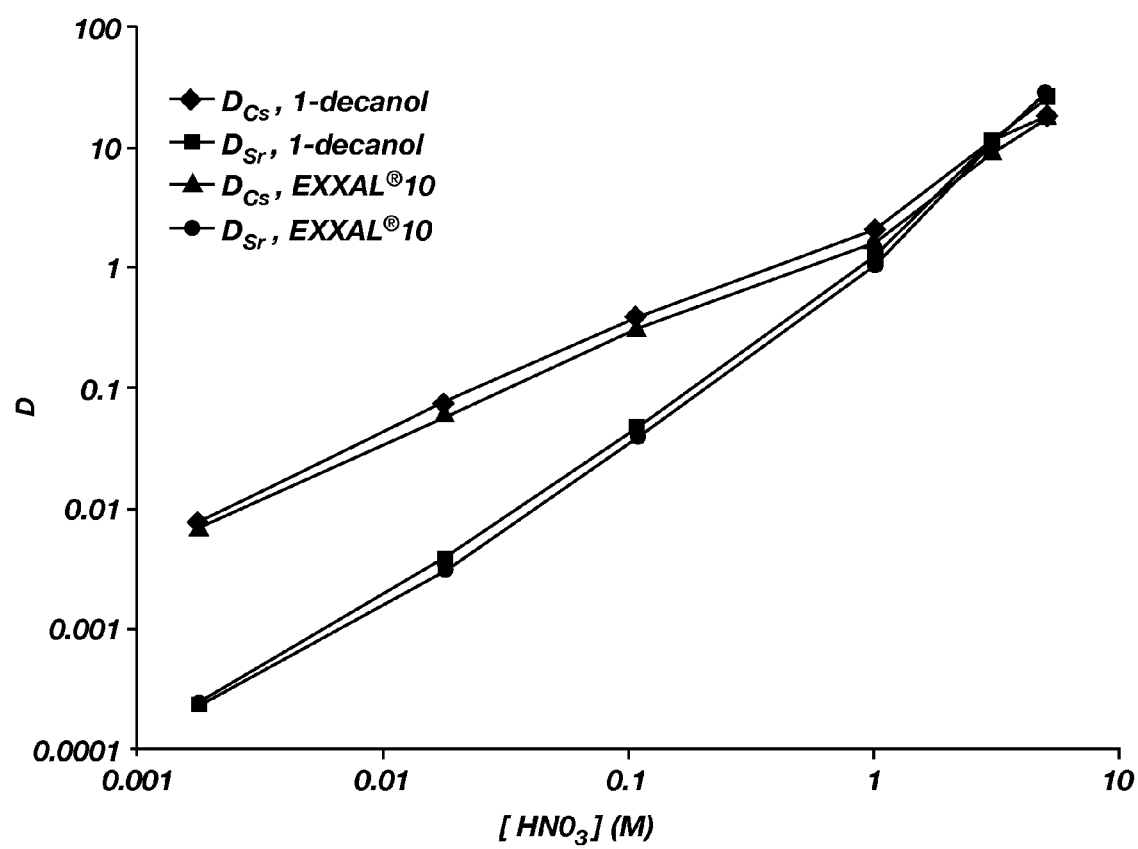
FIG. 9 shows cesium and strontium distribution ratios as a function of $HNO_3$ concentration for mixed extractant solvents including MC-10B and 1-decanol or EXXAL® 10 as the modifier.

The effect of straight chain versus branched chain primary alcohols on the extraction performance of MC-10B was evaluated by measuring cesium and strontium distribution ratios as a function of $HNO_3$ concentration. The mixed extractant solvent included 0.025 M MC-10B, 0.150 M DtBuCH18C6, 0.003 M TOA, and 1.25 M EXXAL® 10 (branched chain decanol) dissolved in ISOPAR® L or 0.025 M MC-10B, 0.150 M DtBuCH18C6, 0.003 M TOA, and 1-decanol (straight chain decanol) dissolved in ISOPAR® L. The aqueous feed included 0.004 M cesium nitrate, 0.002 M strontium nitrate, and varying concentrations of $HNO_3$ (0.003 M, 0.03 M, 0.1 M, 1 M, 5 M, or 7 M). As shown in FIG. 9, the cesium and strontium distribution ratios for both the straight chain and the branched chain decanols were similar.

Example 12

Cesium And Strontium Extractant Performance Of MC-10B And 1-Octanol

Figure 10:
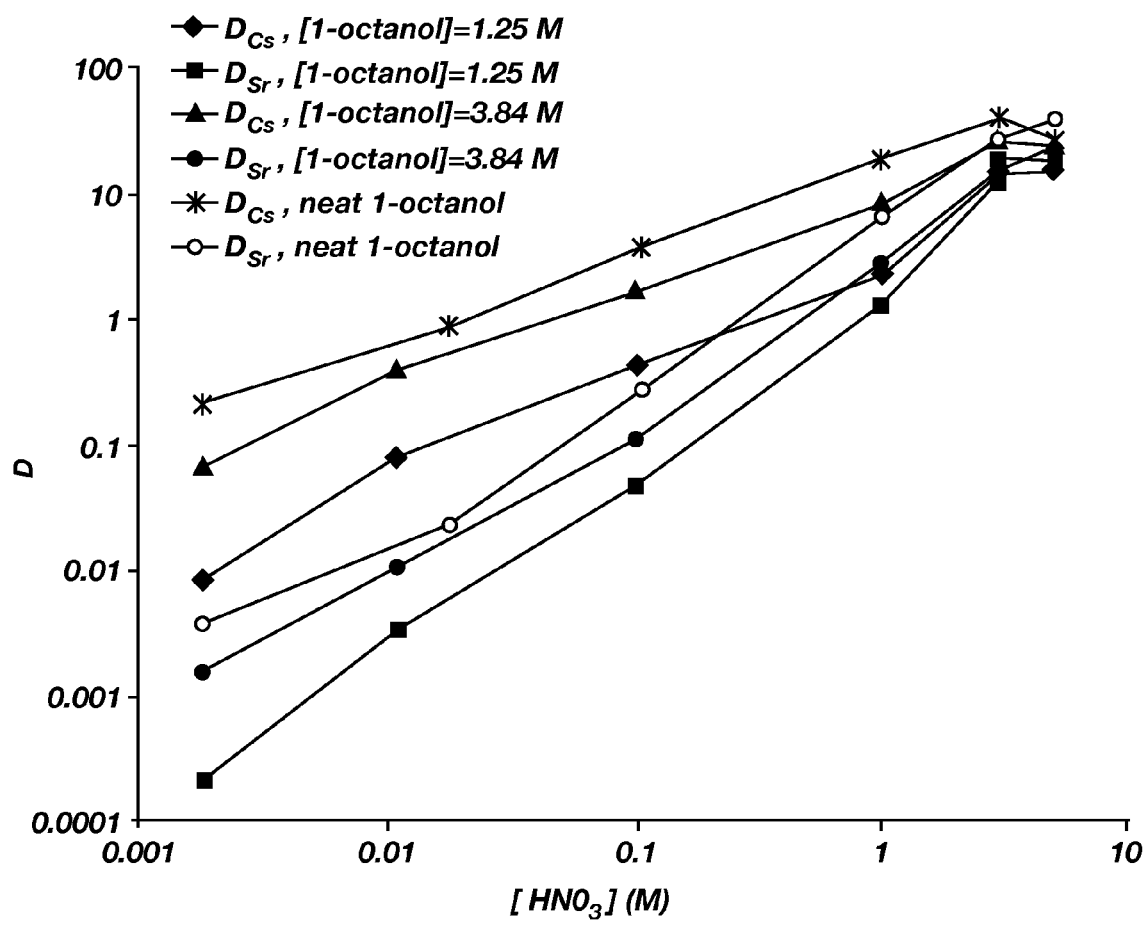
FIG. 10 shows cesium and strontium distribution ratios as a function of $HNO_3$ concentration for mixed extractant solvents including MC-10B and 1-octanol.

The extraction performance of MC-10B was evaluated by measuring cesium and strontium distribution ratios as a function of 1-octanol concentration. The mixed extractant solvents included 0.025 M MC-10B, 0.150 M DtBuCH18C6, and varying concentrations of 1-octanol (1.25 M, 3.84 M, or neat 1-octanol). The mixed extractant solvents including 1.25 M or 3.84 M 1-octanol were dissolved in ISOPAR® L, while the mixed extractant solvents including neat 1-octanol were not dissolved in ISOPAR® L. The mixed extractant solvent including 1.25 M 1-octanol also included 0.003 M TOA. The aqueous feed included 0.004 M cesium nitrate, 0.002 M strontium nitrate, and varying concentrations of $HNO_3$ (0.003 M, 0.01 M, 0.1 M, 1 M, 5 M, or 8 M). As shown in FIG. 10, the cesium and strontium distribution ratios increased as the concentration of 1-octanol increased.

Figure 11:
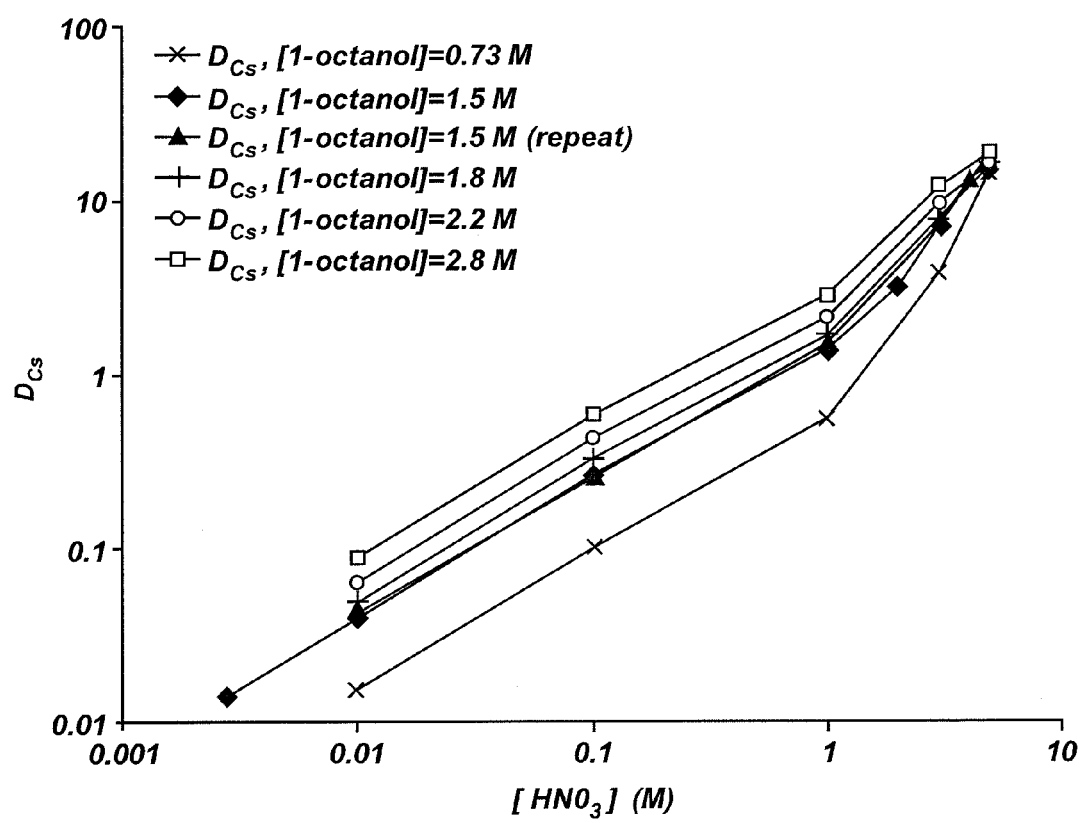
FIGS. 11 and 12 show cesium and strontium distribution ratios, respectively, as a function of $HNO_3$ concentration for mixed extractant solvents including MC-10B and 1-octanol.
Figure 12:
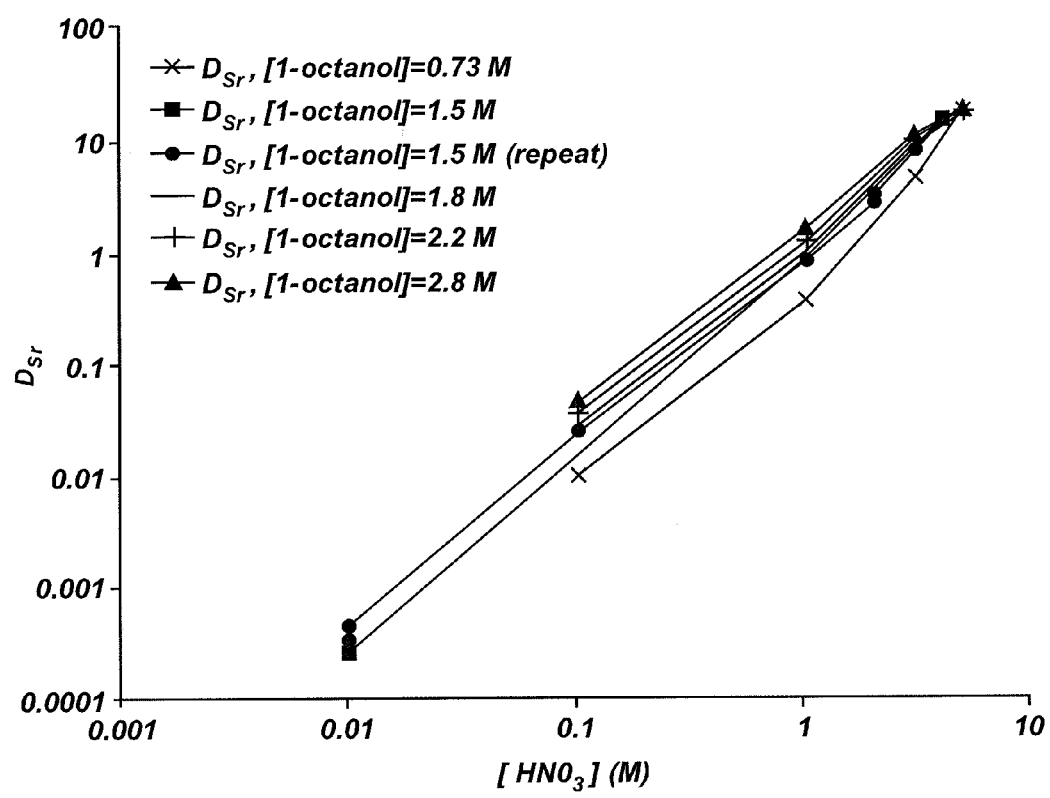

The extraction performance of MC-10B was evaluated by measuring cesium and strontium distribution ratios as a function of $HNO_3$ concentration using mixed extractant solvents of 0.020 M MC-10B, 0.090 M DtBuCH18C6, and varying concentrations of 1-octanol (0.73 M, 1.5 M, 1.8 M, 2.2 M, or 2.8 M) dissolved in ISOPAR® L. The aqueous feed included 0.004 M cesium nitrate, 0.002 M strontium nitrate, and varying concentrations of $HNO_3$ (0.005 M, 0.01 M, 0.1 M, 1 M, 3 M, 5 M, or 8 M). As shown in FIG. 11, the cesium distribution ratios increased as the 1-octanol concentration increased. As shown in FIG. 12, the strontium distribution ratios increased as the 1-octanol concentration increased.

Figure 13:
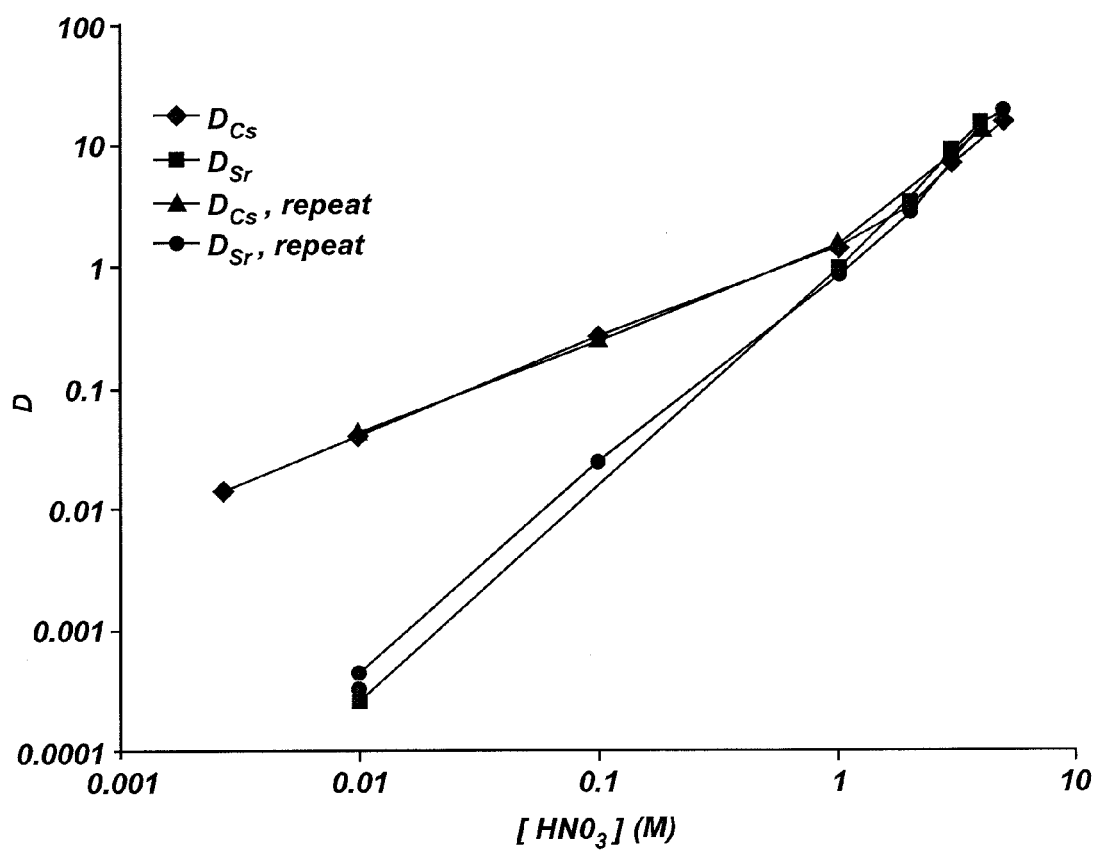
FIG. 13 shows cesium and strontium distribution ratios, respectively, as a function of $HNO_3$ concentration for mixed extractant solvents including MC-10B and 1-octanol.

The extraction performance of MC-10B was evaluated by measuring cesium and strontium distribution ratios as a function of $HNO_3$ concentration using a mixed extractant solvent of 0.02 M MC-10B, 0.09 M DtBuCH18C6, and 1.5 M 1-octanol dissolved in ISOPAR® L. The aqueous feed included 0.004 M cesium nitrate, 0.002 M strontium nitrate, and varying concentrations of $HNO_3$ (0.005 M, 0.01 M, 0.1 M, 1 M, 3 M, 5 M, or 8 M). The cesium and strontium distribution ratios are shown in FIG. 13.

Example 13

Cesium And Strontium Extractant Performance Of MC-10B And EXXAL® 8

Figure 14:
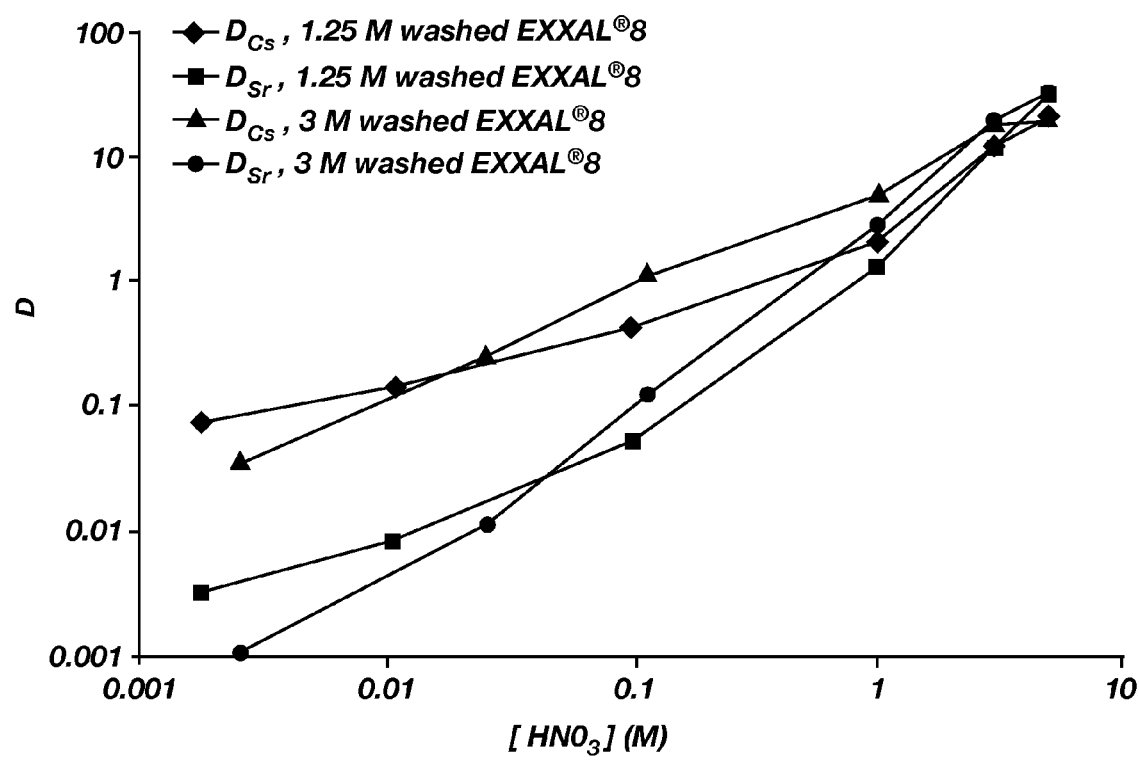
FIGS. 14 and 15 show cesium and strontium distribution ratios as a function of $HNO_3$ concentration for mixed extractant solvents including MC-10B and EXXAL® 8.

The extraction performance of MC-10B was evaluated by measuring cesium and strontium distribution ratios as a function of $HNO_3$ concentration using mixed extractant solvents of 0.025 M MC-10B, 0.150 M DtBuCH18C6, 0.003 M TOA, and varying concentrations of EXXAL® 8 (1.25 M or 3 M) dissolved in ISOPAR® L. The aqueous feed included 0.004 M cesium nitrate, 0.002 M strontium nitrate, and varying concentrations of $HNO_3$ (0.003 M, 0.004 M, 0.01 M, 0.03 M, 0.1 M, 1 M, 5 M, or 8 M). As shown in FIG. 14, at $HNO_3$ concentrations above 0.1 M, the cesium and strontium distribution ratios increased for increased EXXAL® 8 concentrations.

Figure 15:
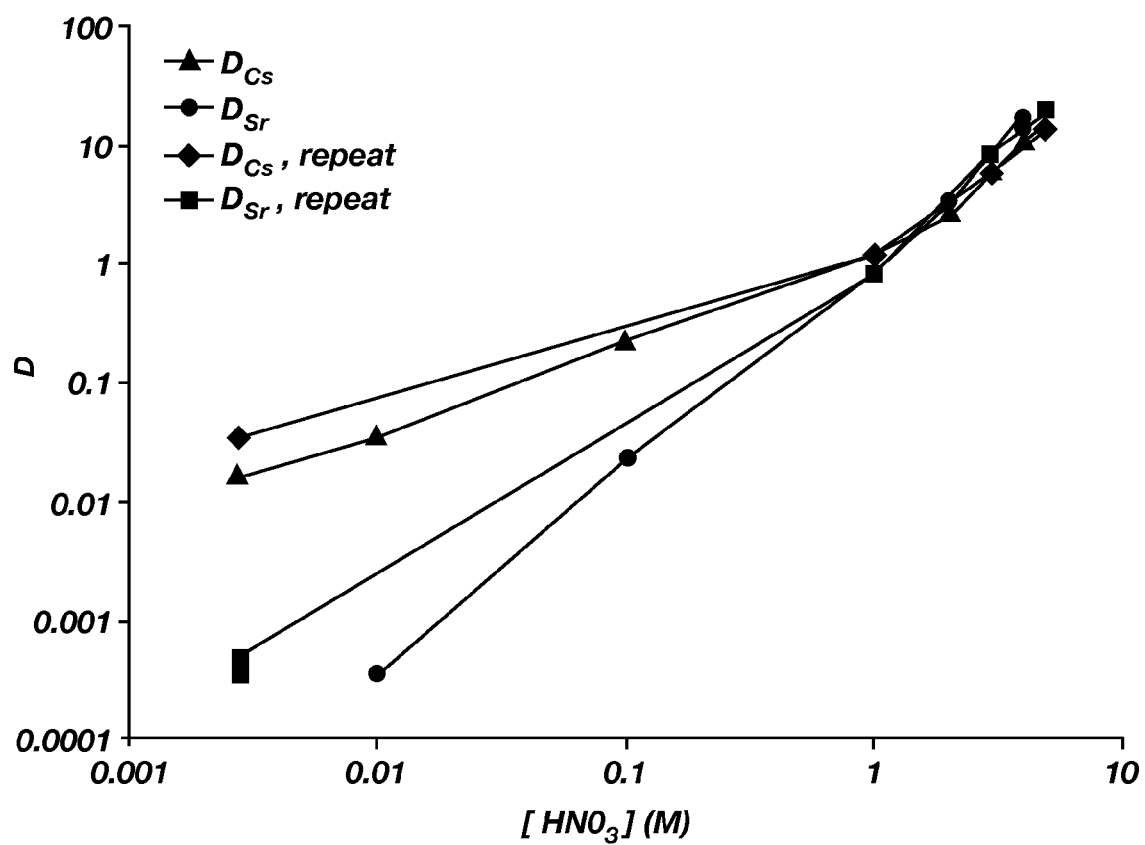

The extraction performance of MC-10B was evaluated by measuring cesium and strontium distribution ratios as a function of $HNO_3$ concentration using a mixed extractant solvent of 0.020 M MC-10B, 0.090 M DtBuCH18C6, and 1.523 M EXXAL® 8 dissolved in ISOPAR® L. The aqueous feed included 0.004 M cesium nitrate, 0.002 M strontium nitrate, and varying concentrations of $HNO_3$ (0.003 M, 0.01 M, 0.1 M, 1 M, 3 M, 5 M, 7 M, or 8 M). The cesium and strontium distribution ratios are shown in FIG. 15.

Example 14

Cesium And Strontium Extractant Performance Of MC-10B And EXXAL® 8, EXXAL® 10, Or EXXAL® 12

Figure 16:
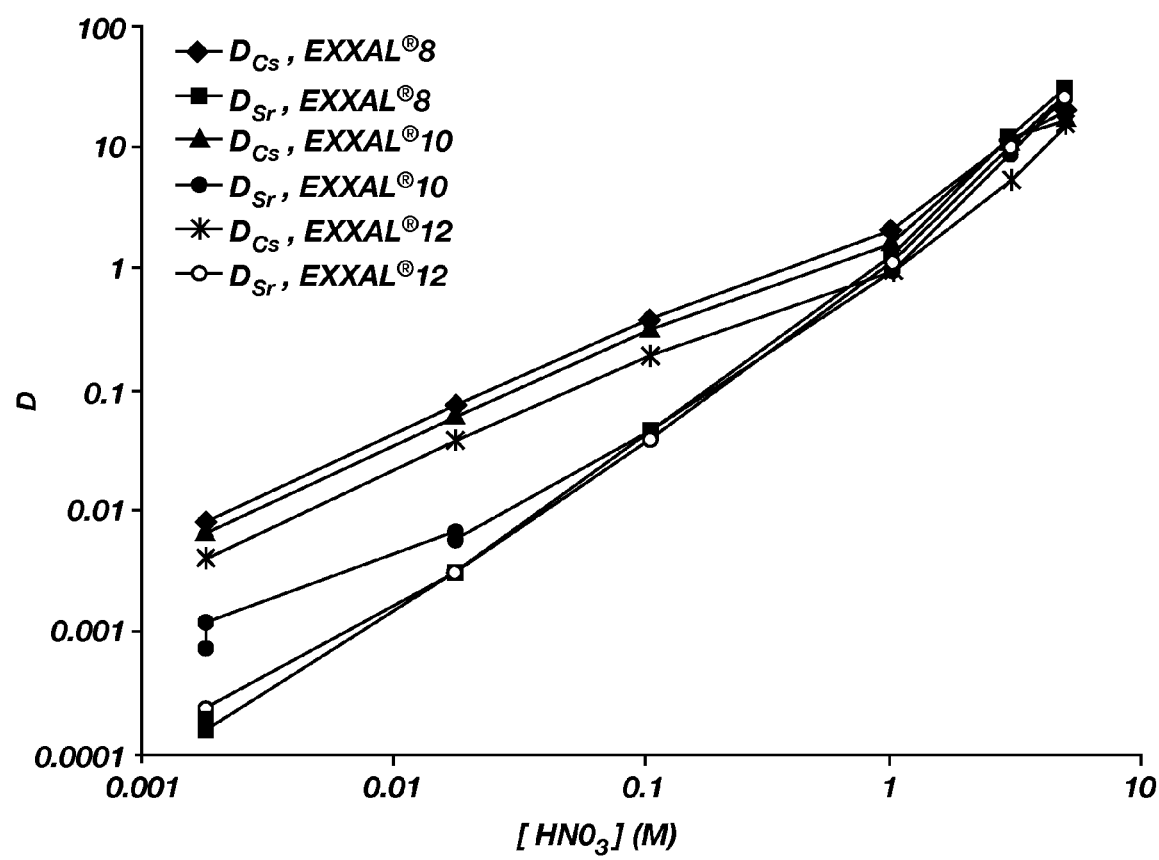
FIG. 16 shows cesium and strontium distribution ratios as a function of $HNO_3$ concentration for mixed extractant solvents including MC-10B and EXXAL® 8, EXXAL® 10, or EXXAL® 12 as the modifier.

The effect of chain length for branched chain C8, C10, and C12 primary alcohols on the extraction performance of MC-10B was evaluated by measuring cesium and strontium distribution ratios as a function of $HNO_3$ concentration. The mixed extractant solvents included 0.025 M MC-10B, 0.150 M DtBuCH18C6, 0.003 M TOA, and 1.25 M EXXAL® 8, EXXAL® 10, or EXXAL® 12 dissolved in ISOPAR® L. The aqueous feed included 0.004 M cesium nitrate, 0.002 M strontium nitrate, and varying concentrations of $HNO_3$ (0.003 M, 0.03 M, 0.1 M, 1 M, 5 M, or 8 M). As shown in FIG. 16, the cesium and strontium distribution ratios increased slightly as the chain length decreased.

Example 15

Cesium And Strontium Extractant Performance Of MC-10B And Cs-5SB

Figure 17:
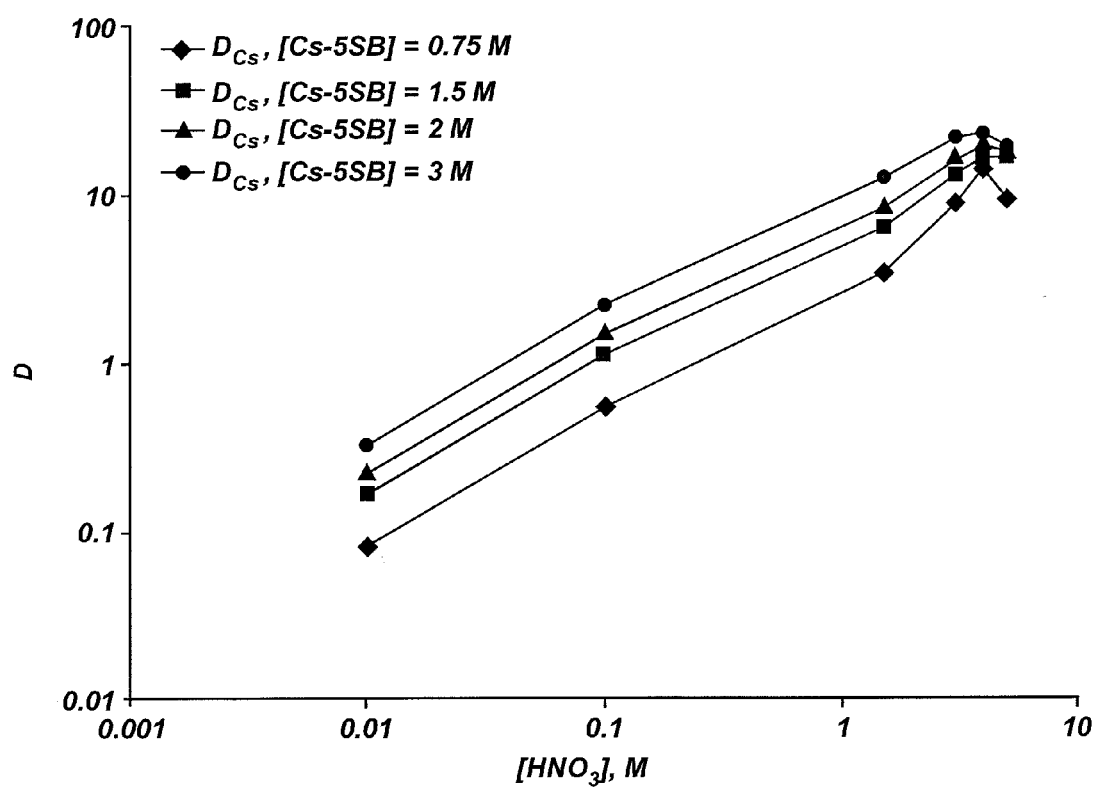
FIGS. 17 and 18 show cesium and strontium distribution ratios, respectively, as a function of $HNO_3$ concentration for mixed extractant solvents including MC-10B and Cs-5SB.
Figure 18:
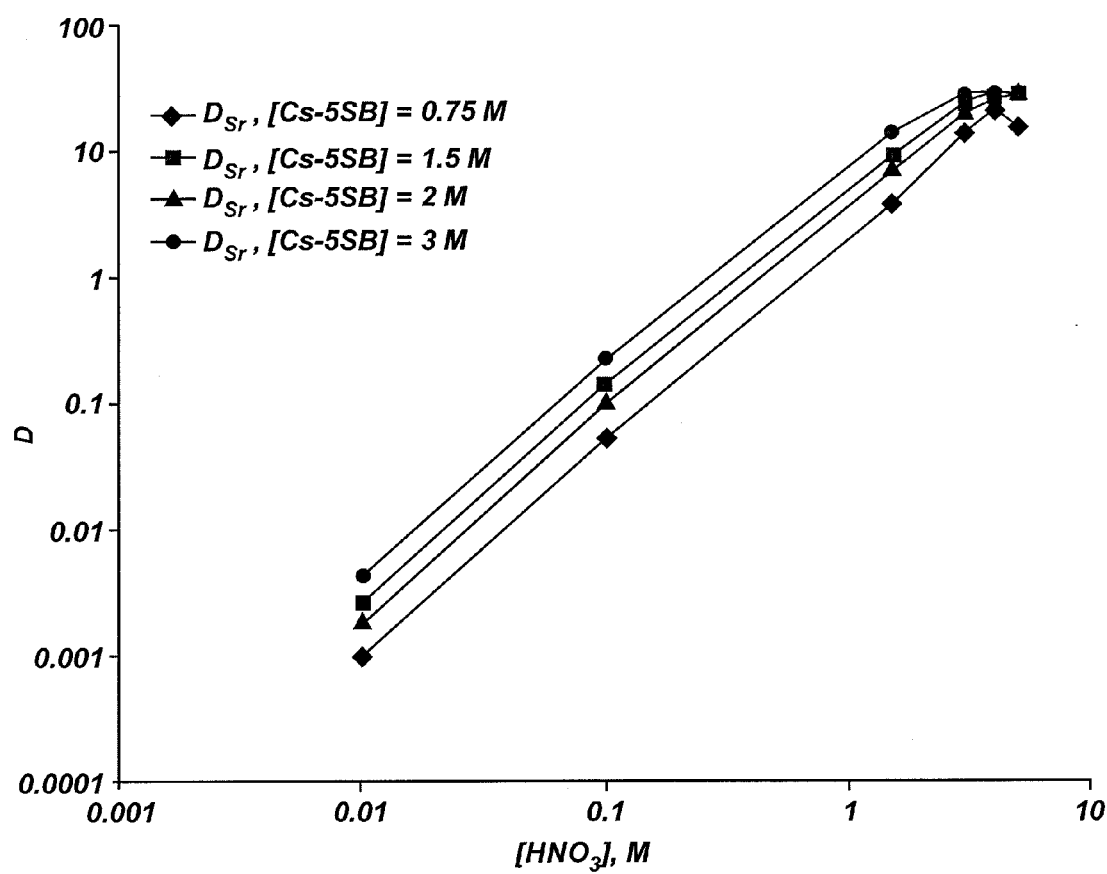

The extraction performance of MC-10B was evaluated by measuring cesium and strontium distribution ratios as a function of $HNO_3$ concentration using a mixed extractant solvent of 0.020 M MC-10B, 0.090 M DtBuCH18C6, and varying concentrations of Cs-5SB (0.75 M, 1.5 M, 2 M, or 3 M) dissolved in ISOPAR® L. The aqueous feed included 0.004 M cesium nitrate, 0.002 M strontium nitrate, and varying concentrations of $HNO_3$ (0.01 M, 0.1 M, 1.5 M, 3 M, 4 M, or 5 M). As shown in FIGS. 17 and 18, the cesium and strontium distribution ratios increased as the Cs-5SB concentration increased.

The extraction performance of MC-10B was evaluated by measuring cesium and strontium distribution ratios as a function of MC-10B and DtBuCH18C6 concentrations using mixed extractant solvents of varying MC-10B and DtBuCH18C6 concentrations and 1.5 M Cs-5SB dissolved in ISOPAR® L. The aqueous feed included 0.004 M cesium nitrate, 0.002 M strontium nitrate, and 1.5 $HNO_3$. A ratio of the DtBuCH18C6 concentration to MC-10B concentration and the cesium and strontium distribution ratios are shown in Table 11.

TABLE 11

Cesium And Strontium Distribution Ratios.

| [DtBuCH18C6]/[MC-10B] (mM) | $D_{Cs}$ | $D_{Sr}$ |
|---|---|---|
| 90/20 | 6.11 | 6.90 |
| 90/20 | 6.36 | 6.94 |
| 60/15 | 4.48 | 4.73 |
| 60/15 | 4.37 | 4.69 |
| 50/10 | 2.87 | 4.03 |
| 50/10 | 2.88 | 4.11 |
| 60/10 | 2.77 | 4.83 |
| 60/10 | 2.81 | 4.90 |

No third phase formation was observed at the tested MC-10B and DtBuCH18C6 concentrations.

Example 16

Cesium And Strontium Extractant Performance Of BOBCalixC6 And EXXAL® 8

Figure 19:
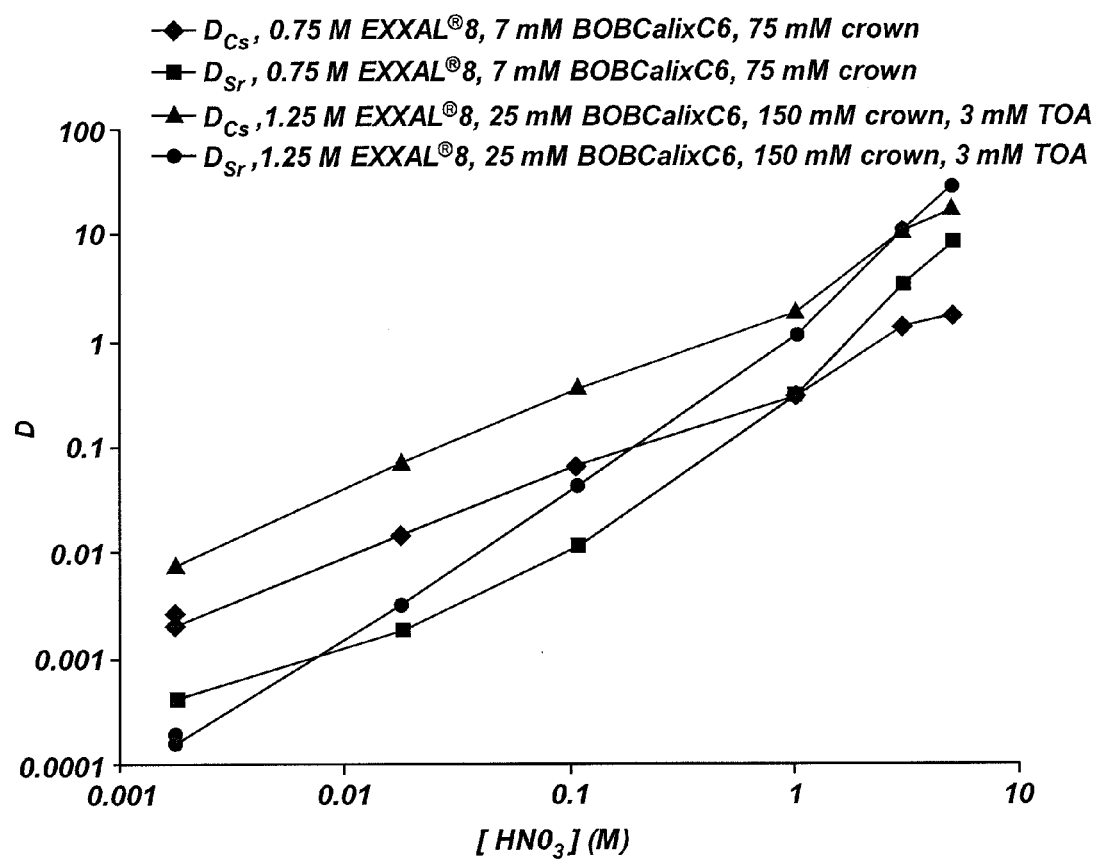
FIGS. 19 and 20 show cesium and strontium distribution ratios as a function of $HNO_3$ concentration for mixed extractant solvents including BOBCalixC6 and EXXAL® 8.

The extraction performance of BOBCalixC6 was evaluated by measuring cesium and strontium distribution ratios as a function of $HNO_3$ concentration using mixed extractant solvents including varying concentrations of BOBCalixC6 (0.007 M or 0.025 M), varying concentrations of DtBuCH18C6 (0.075 M or 0.150 M), and varying concentrations of EXXAL® 8 (0.75 M or 1.25 M) dissolved in ISOPAR® L. The mixed extractant solvents including 1.25 M EXXAL® 8 also included 0.003 M TOA. The aqueous feed included 0.004 M cesium nitrate, 0.002 M strontium nitrate, and varying concentrations of $HNO_3$ (0.003 M, 0.03 M, 0.1 M, 1 M, 5 M, or 8 M). As shown in FIG. 19, the cesium distribution ratios increased at a higher concentration of EXXAL® 8, while the strontium distribution ratios increased at a higher concentration of EXXAL® 8 above a $HNO_3$ concentration of 0.01 M.

Figure 20:
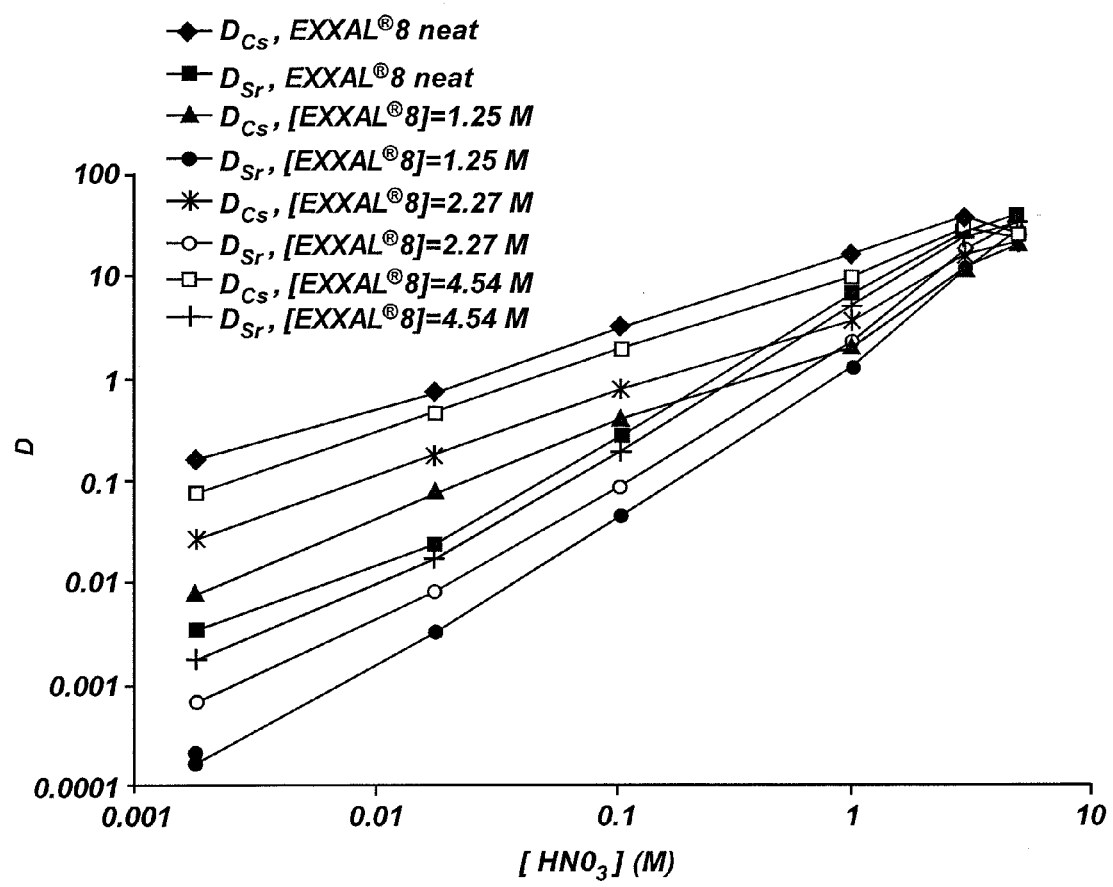

The extraction performance of BOBCalixC6 was evaluated by measuring cesium and strontium distribution ratios as a function of $HNO_3$ concentration using mixed extractant solvents including 0.025 M BOBCalixC6, 0.150 M DtBuCH18C6, and varying concentrations of EXXAL® 8 (1.25 M, 2.27 M, or 4.54 M) dissolved in ISOPAR® L. In addition, a mixed extractant solvent including 0.025 M BOBCalixC6, 0.150 M DtBuCH18C6, and neat EXXAL® 8 (no ISOPAR® L) was tested. The mixed extractant solvents including 1.25 M EXXAL® 8 also included 0.003 M TOA. The aqueous feed included 0.004 M cesium nitrate, 0.002 M strontium nitrate, and varying concentrations of $HNO_3$ (0.003 M, 0.03 M, 0.1 M, 1 M, 5 M, or 8 M). As shown in FIG. 20, the cesium and strontium distribution ratios increased as the concentration of EXXAL® 8 increased.

Example 17

Cesium And Strontium Extractant Performance Of BOBCalixC6 And EXXAL® 12

Figure 21:
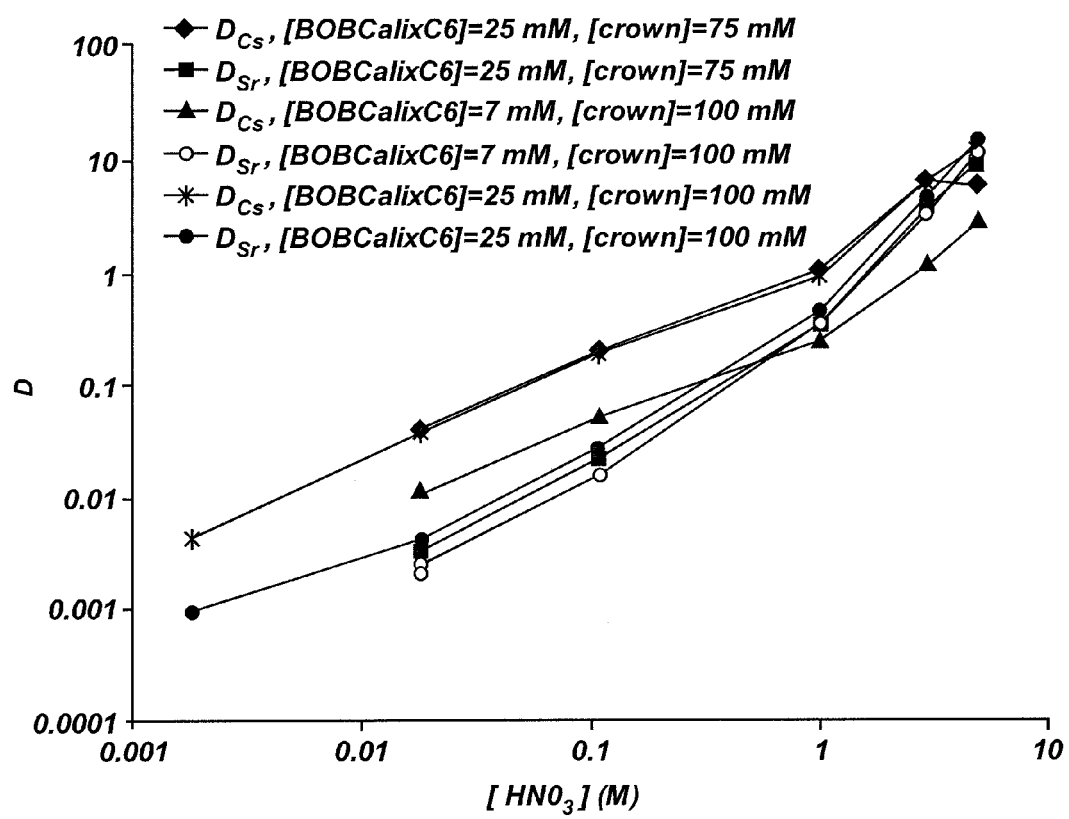
FIGS. 21 and 22 show cesium and strontium distribution ratios as a function of $HNO_3$ concentration for mixed extractant solvents including BOBCalixC6 and EXXAL® 12.

The extraction performance of BOBCalixC6 was evaluated by measuring cesium and strontium distribution ratios as a function of HNO₃ concentration using mixed extractant solvents including varying concentrations of BOBCalixC6 (0.007 M or 0.025 M), varying concentrations of DtBuCH18C6 (0.075 M or 0.10 M), 0.003 M TOA, and 0.75 M EXXAL® 12 dissolved in ISOPAR® L. The aqueous feed included 0.004 M cesium nitrate, 0.002 M strontium nitrate, and varying concentrations of HNO₃ (0.003 M, 0.03 M, 0.1 M, 1 M, 5 M, or 8 M). The cesium and strontium distribution ratios are shown in FIG. 21. Third phase formation was observed at 5 M HNO₃ when the mixed extractant solvent included 0.025 M BOBCalixC6 and 0.075 DtBuCH18C6.

Figure 22:
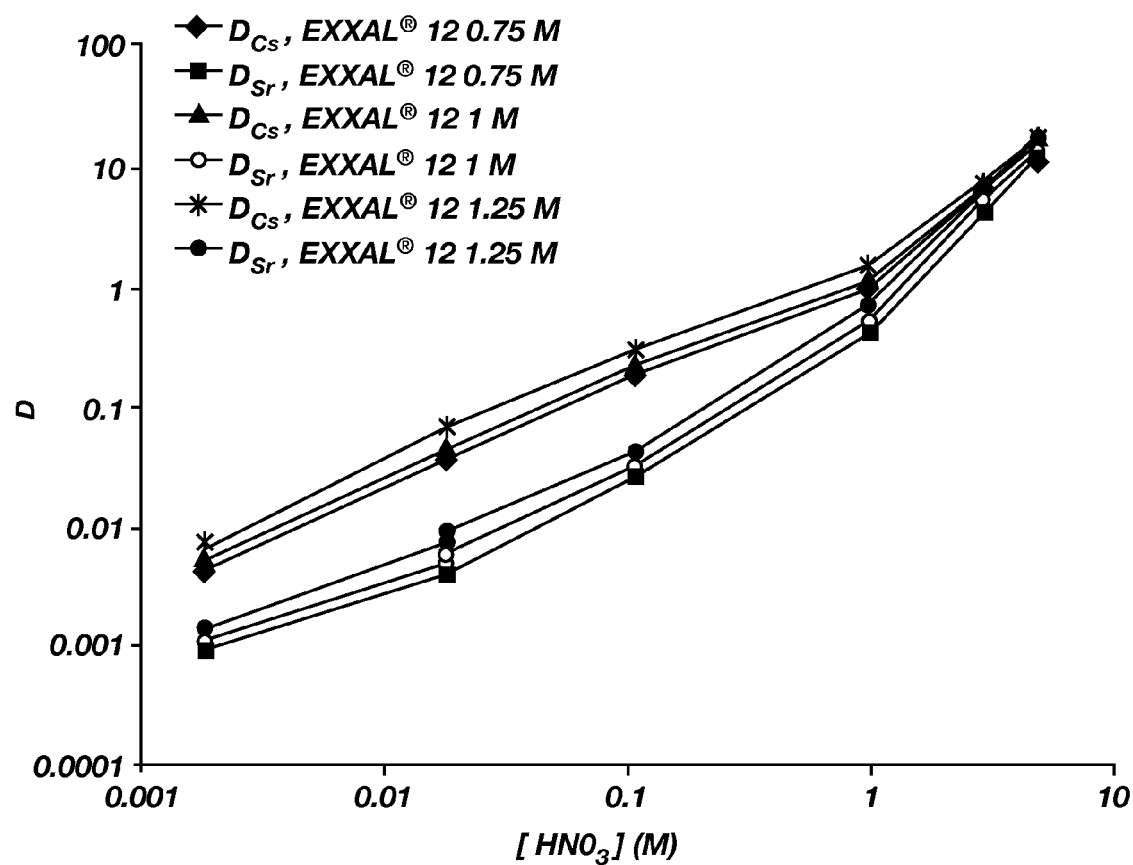

The extraction performance of BOBCalixC6 was evaluated by measuring cesium and strontium distribution ratios as a function of HNO₃ concentration using mixed extractant solvents including 0.025 M BOBCalixC6, 0.100 M DtBuCH18C6, 0.003 M TOA, and varying concentrations of EXXAL® 12 (0.75 M, 1 M, or 1.25 M) dissolved in ISOPAR® L. The aqueous feed included 0.004 M cesium nitrate, 0.002 M strontium nitrate, and varying concentrations of HNO₃ (0.003 M, 0.03 M, 0.1 M, 1 M, 5 M, and 8 M). As shown in FIG. 22, the cesium and strontium distribution ratios increased as the EXXAL® 12 concentration increased.

Figure 23:
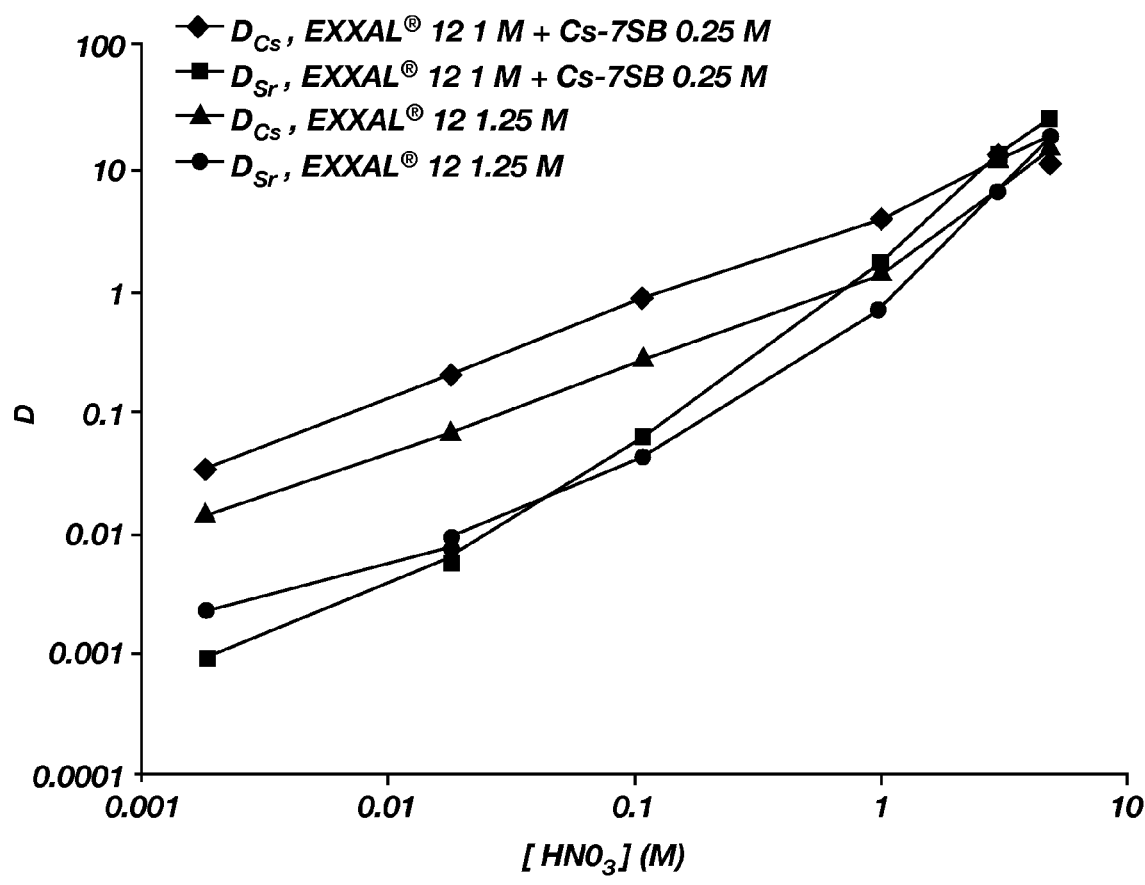
FIG. 23 shows cesium and strontium distribution ratios as a function of $HNO_3$ concentration for mixed extractant solvents including BOBCalixC6, Cs-7SB, and EXXAL® 12.

The effect of using Cs-7SB in addition to EXXAL® 12 was investigated. The extraction performance of BOBCalixC6 was evaluated by measuring cesium and strontium distribution ratios as a function of HNO₃ concentration using a mixed extractant solvent including 0.025 M BOBCalixC6, 0.100 M DtBuCH18C6, and 1.25 M EXXAL® 12 dissolved in ISOPAR® L, or 0.025 M BOBCalixC6, 0.100 M DtBuCH18C6, 1.0 M EXXAL® 12, and 0.25 M Cs-7SB dissolved in ISOPAR® L. The aqueous feed included 0.004 M cesium nitrate, 0.002 M strontium nitrate, and varying concentrations of HNO₃ (0.003 M, 0.03 M, 0.1 M, 1 M, 5 M, or 8 M). As shown in FIG. 23, the cesium distribution ratios increased with the addition of Cs-7SB and the strontium distribution ratios increased at a HNO₃ concentration above 0.1 M.

Figure 24:
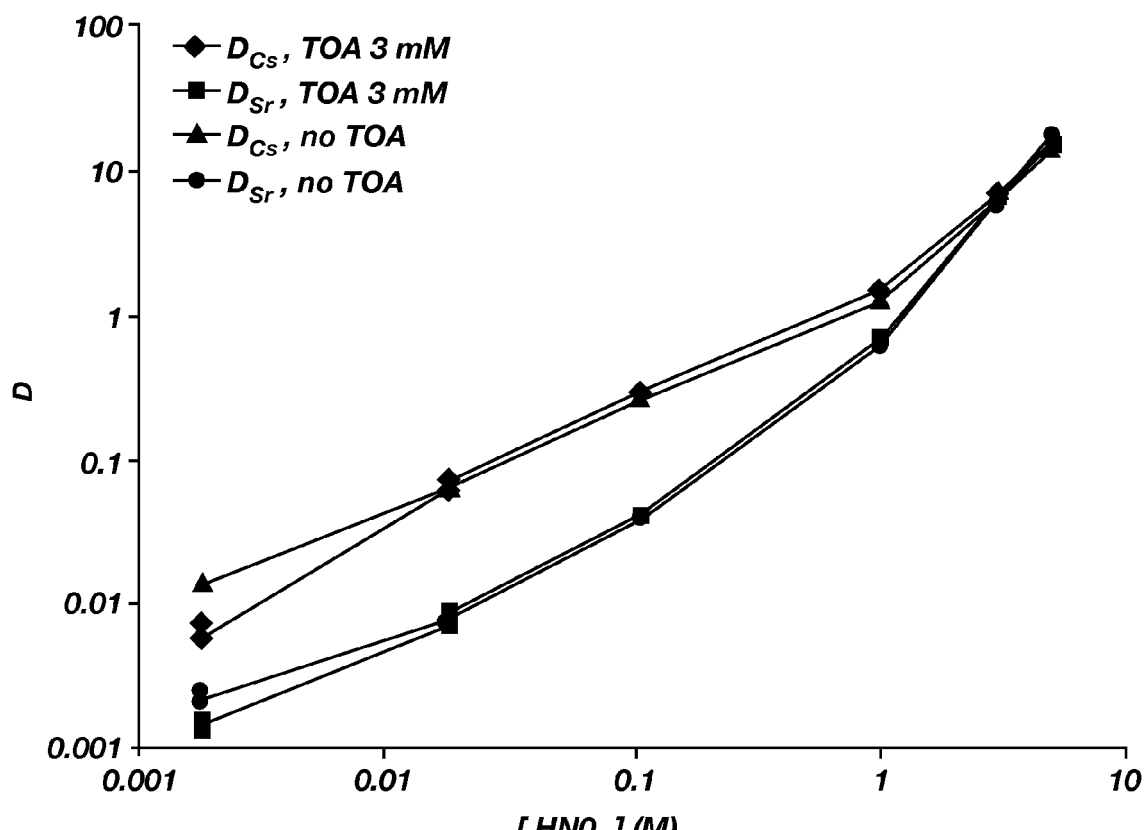
FIG. 24 shows cesium and strontium distribution ratios as a function of $HNO_3$ concentration for mixed extractant solvents including BOBCalixC6, EXXAL® 12, and TOA.

The effect of using TOA with EXXAL® 12 was investigated. The extraction performance of BOBCalixC6 was evaluated by measuring cesium and strontium distribution ratios as a function of HNO₃ concentration using a mixed extractant solvent including 0.025 M BOBCalixC6, 0.100 M DtBuCH18C6, and 1.25 M EXXAL® 12 dissolved in ISOPAR® L, or 0.025 M BOBCalixC6, 0.100 M DtBuCH18C6, 1.25 M EXXAL® 12, and 0.003 M TOA dissolved in ISOPAR® L. The aqueous feed included 0.004 M cesium nitrate, 0.002 M strontium nitrate, and varying concentrations of HNO₃ (0.003 M, 0.03 M, 0.1 M, 1 M, 5 M, or 8 M). As shown in FIG. 24, the presence of TOA in the mixed extractant solvent affects the cesium and strontium distributions at low concentrations of HNO₃, such as below 0.03 M HNO₃.

Example 18

Figure 25:
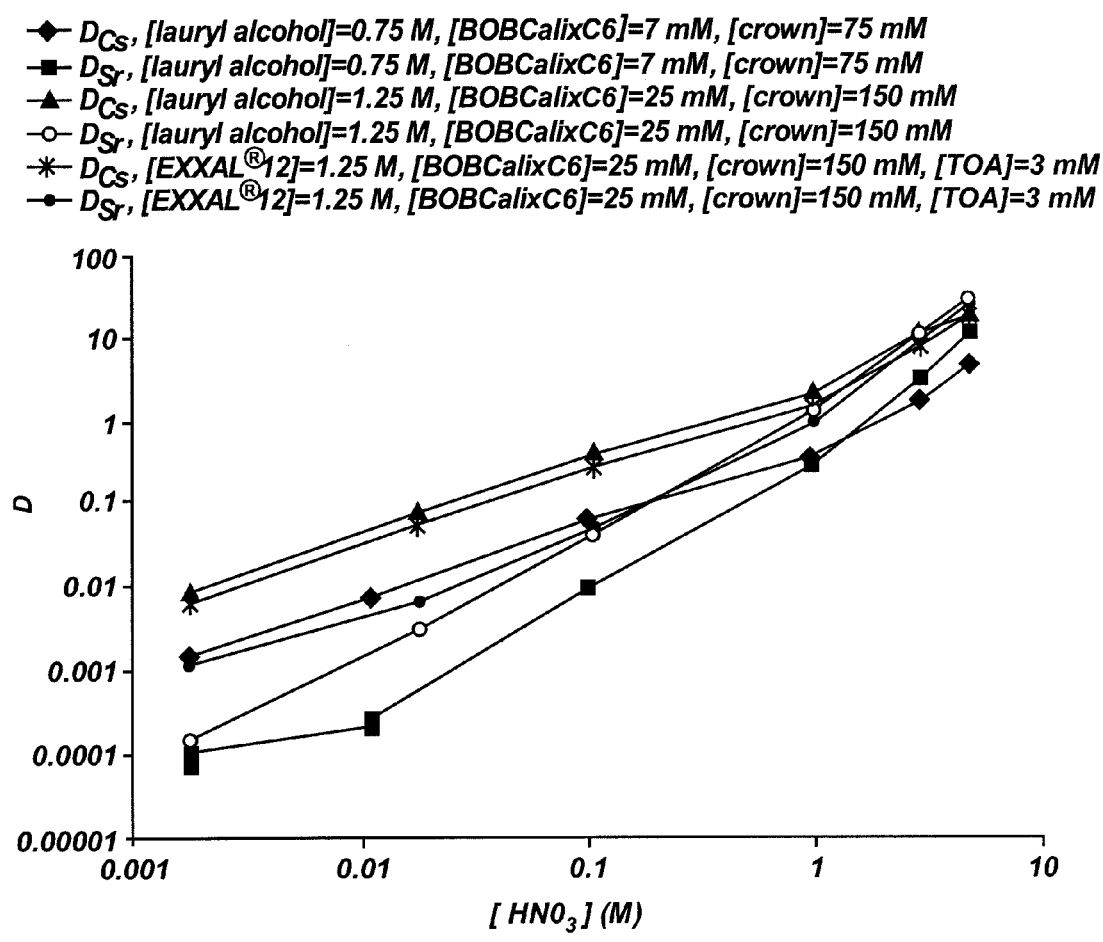
FIG. 25 shows cesium and strontium distribution ratios as a function of $HNO_3$ concentration for mixed extractant solvents including BOBCalixC6 and lauryl alcohol or EXXAL® 12 as the modifier.

Cesium And Strontium Extractant Performance Of BOBCalixC6 And EXXAL® 12 Versus Lauryl Alcohol The extraction performance of BOBCalixC6 was evaluated by measuring cesium and strontium distribution ratios as a function of HNO₃ concentration using mixed extractant solvents including varying concentrations of BOBCalixC6 (0.007 M or 0.025 M), varying concentrations of DtBuCH18C6 (0.075 M or 0.150 M), and varying concentrations of EXXAL® 12 or lauryl alcohol (also known as dodecanol) (0.75 M or 1.25 M) dissolved in ISOPAR® L. Mixed extractant solvents including EXXAL® 12 also included 0.003 M TOA. The aqueous feed included 0.004 M cesium nitrate, 0.002 M strontium nitrate, and varying concentrations of HNO₃ (0.003 M, 0.018 M, 0.1 M, 1 M, 5 M, or 7 M). The cesium and strontium distribution ratios are shown in FIG. 25 and indicate that the extractant performance for the mixed extractant solvents including the linear (lauryl alcohol) versus branched (EXXAL® 12) alcohol are similar.

Example 19

Figure 26:
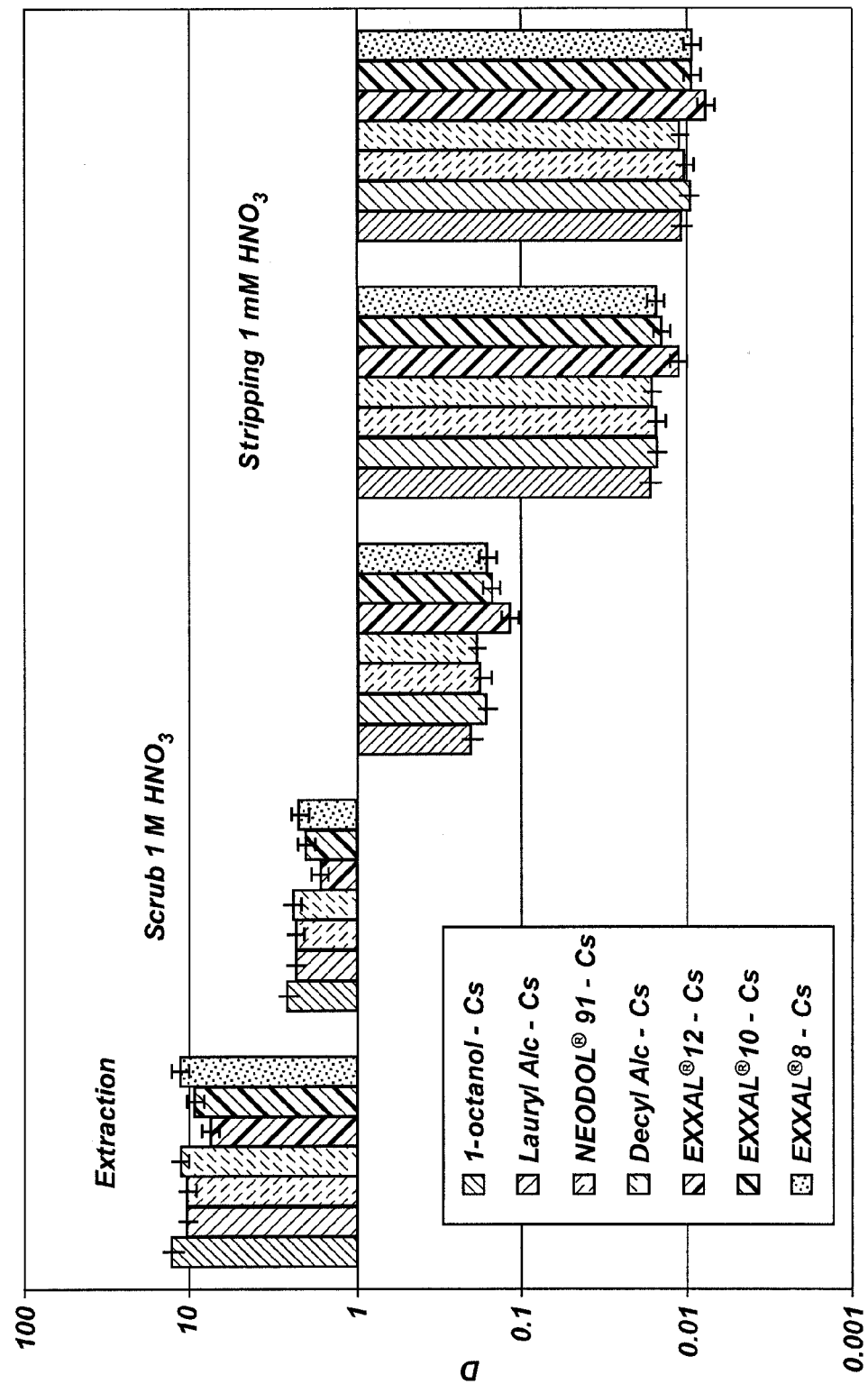
FIGS. 26 and 27 show cesium and strontium distribution ratios for the extraction, scrub, and backward extraction for mixed extractant solvents including BOBCalixC6 and 1-octanol, lauryl alcohol, NEODOL® 91, decyl alcohol, EXXAL® 8, EXXAL® 10, or EXXAL® 12 as the modifier.
Figure 27:
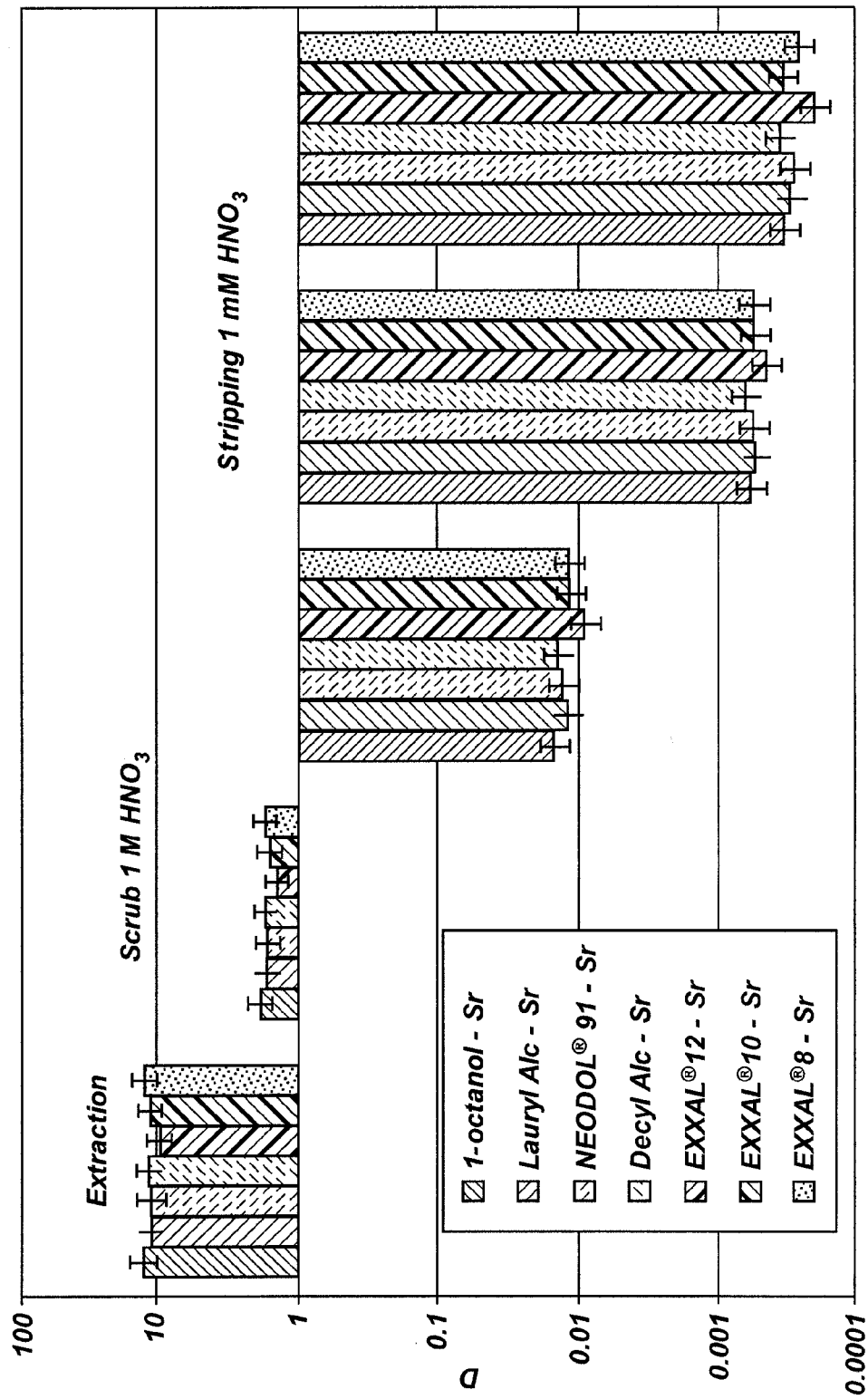

Cesium And Strontium Extractant, Scrub, And Strip Performance Of BOBCalixC6 And Various Alcohols The extraction and backward extraction performance of various mixed extractant solvents was evaluated to determine the effect of different alcohols (1-octanol, lauryl alcohol, NEODOL® 91, decyl alcohol, EXXAL® 8, EXXAL® 10, or EXXAL® 12) as modifiers. The mixed extractant solvents included 0.025 M BOBCalixC6, 0.150 M DtBuCH18C6, 0.003 M TOA, and 1.25 M of the modifier dissolved in ISOPAR® L. The aqueous feed included 0.004 M cesium nitrate, 0.002 M strontium nitrate, and 3 M HNO₃. The scrub solution included 1 M HNO₃. The stripping solution used for the backward extraction included 1 mM HNO₃. After the forward extraction and the scrub, three consecutive backward extractions were conducted on the organic phase, which included the radionuclides, using fresh volumes of the stripping solutions. The cesium and strontium distribution ratios for the forward extraction, scrub, and backward extractions are shown in FIGS. 26 and 27, respectively. The cesium and strontium distribution ratios for the backward extractions indicate that the 1 M HNO₃ solution provided effective recovery of the radionuclides.

Example 20

Cesium And Strontium Extractant Performance Of BOBCalixC6 And Cs-4SB

Figure 28:
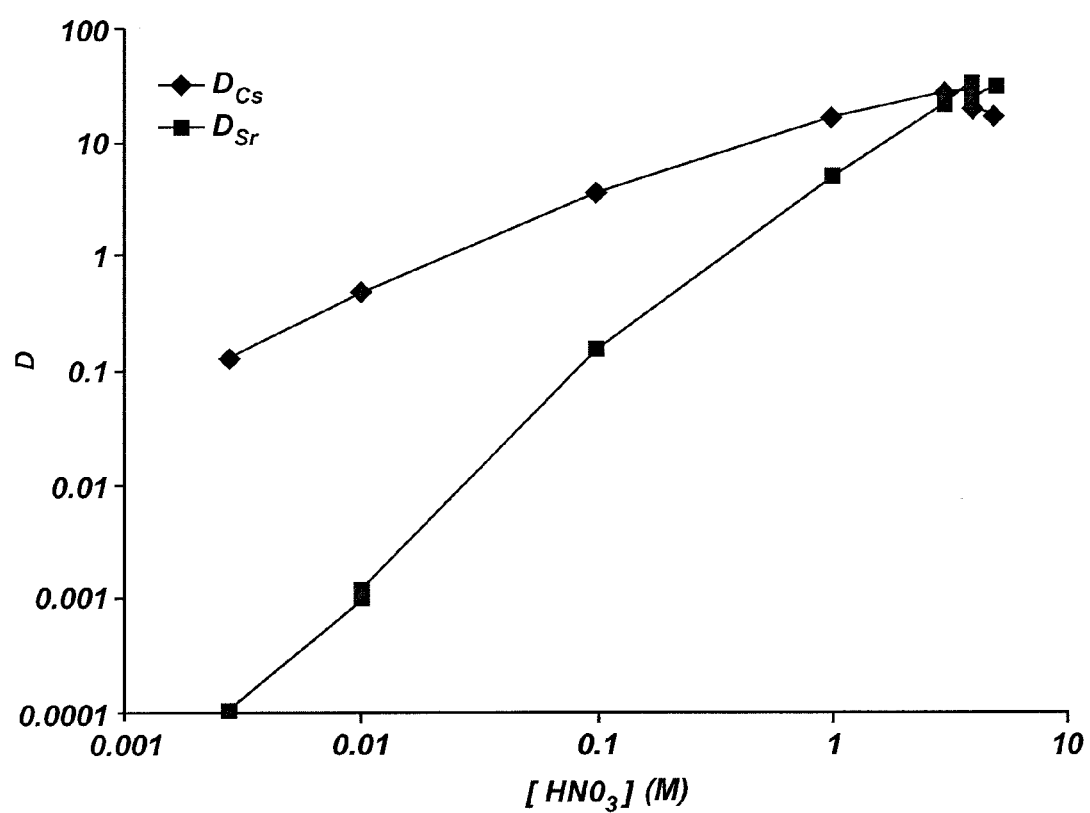
FIG. 28 shows cesium and strontium distribution ratios as a function of $HNO_3$ concentration for a mixed extractant solvent including BOBCalixC6 and Cs-4SB.

The extraction performance of BOBCalixC6 was evaluated by measuring cesium and strontium distribution ratios as a function of HNO₃ concentration using a mixed extractant solvent of 0.020 M BOBCalixC6, 0.090 M DtBuCH18C6, and 1.523 M Cs-4SB dissolved in ISOPAR® L. The aqueous feed included 0.004 M cesium nitrate, 0.002 M strontium nitrate, and varying concentrations of HNO₃ (0.004 M, 0.01 M, 0.1 M, 1 M, 5 M, 6 M, or 7 M). The cesium and strontium distribution ratios are shown in FIG. 28.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A mixed extractant solvent, comprising:
at least one dialkyloxycalix[4]arenebenzocrown-6 compound selected from the group consisting of:

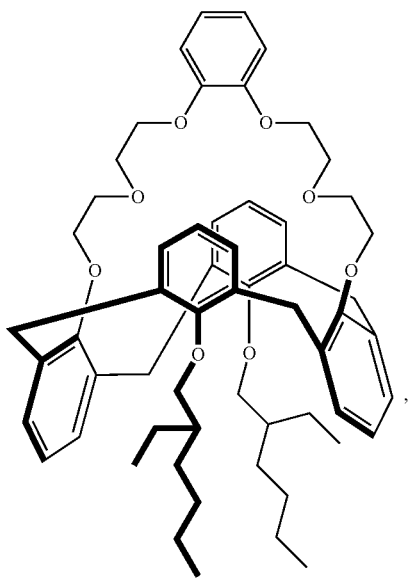

,

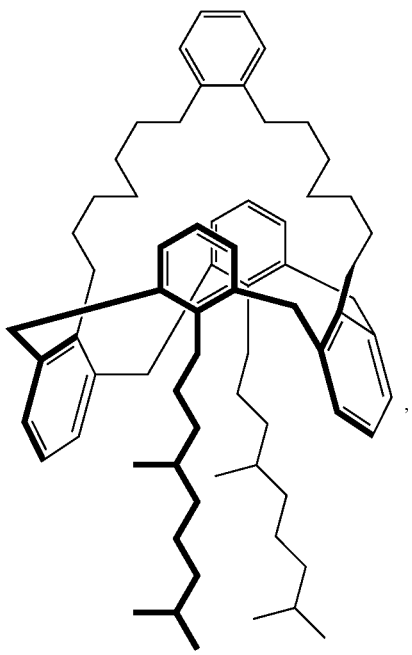

,

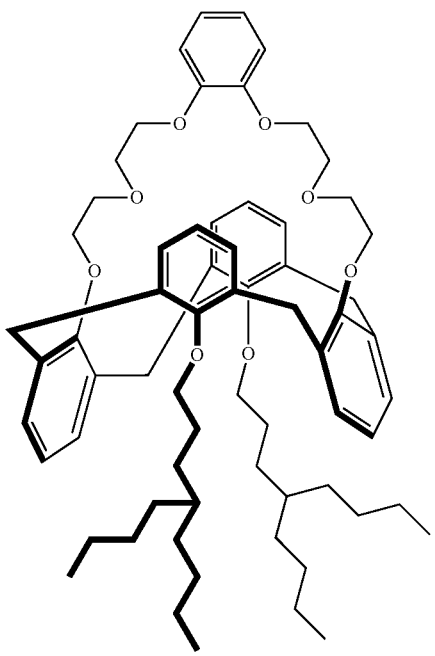

and combinations thereof;
4',4',(5')-di-(t-butyldicyclohexano)-18-crown-6; at least one modifier; and a diluent.

2. The mixed extractant solvent of claim 1, wherein the at least one modifier comprises at least one primary alcohol modifier.

3. The mixed extractant solvent of claim 2, wherein the at least one primary alcohol modifier comprises at least one alkylphenoxy ethyl alcohol lacking fluorine substituents, at least one alkylphenoxy propyl alcohol lacking fluorine substituents, or combinations thereof.

4. The mixed extractant solvent of claim 2, wherein the at least one primary alcohol modifier comprises 3-[4-(tert-octyl)phenoxy]-1-propanol, 3-[4-(sec-butyl)phenoxy]-1-propanol, 3-[4-(tert-octyl)phenoxy]-2-methyl-1-propanol, 3-[4-(sec-butyl)phenoxy]-2-methyl-1-propanol, or combinations thereof.

5. The mixed extractant solvent of claim 2, wherein the at least one primary alcohol modifier comprises a straight chain primary alcohol selected from the group consisting of 1-hexanol, 1-heptanol, 1-octanol, 1-nonanol, 1-decanol, 1-undecanol, 1-dodecanol, and combinations thereof.

6. The mixed extractant solvent of claim 5, wherein the at least one primary alcohol modifier comprises from 75% by weight to 85% by weight of $C_9$, $C_{10}$, and $C_{11}$ primary alcohols.

7. The mixed extractant solvent of claim 2, wherein the at least one primary alcohol modifier comprises a branched isomer of hexanol, heptanol, octanol, nonanol, decanol, undecanol, dodecanol, tridecanol, or combinations thereof.

8. The mixed extractant solvent of claim 7, wherein the at least one primary alcohol modifier comprises methylpentanol, ethylbutanol, methylhexanol, ethylpentanol, methylheptanol, ethylhexanol, methyloctanol, ethylheptanol, methylnonanol, ethyloctanol, methyldecanol, ethylnonanol, methylundecanol, ethyldecanol, methyldodecanol, ethylundecanol, or combinations thereof.

9. The mixed extractant solvent of claim 1, wherein the mixed extractant solvent consists essentially of:

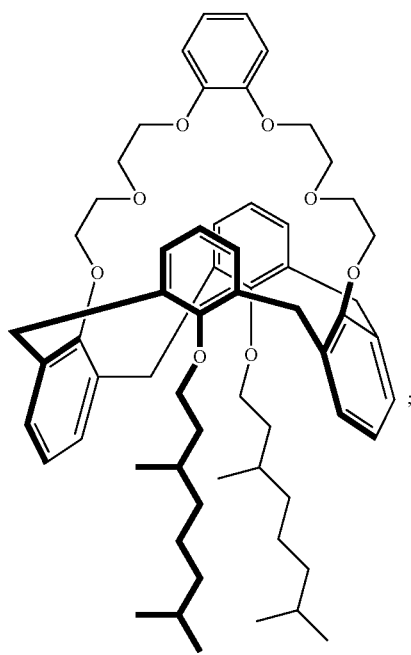

4',4',(5')-di-(t-butyldicyclo-hexano)-18-crown-6;
3-[4-(sec-butyl)phenoxy]-2-methyl-1-propanol; and the diluent.

10. The mixed extractant solvent of claim 1, further comprising an amine.

11. A mixed extractant solvent, comprising:
at least one dialkyloxycalix[4]arenebenzocrown-6 compound;
4',4',(5')-di-(t-butyldicyclo-hexano)-18-crown-6; and
at least one modifier comprising an alkylphenoxy alcohol compound lacking fluorine substituents, wherein the alkylphenoxy alcohol compound is not 2-(4-tert-octylphenoxy)-1 -ethanol ,1-ethoxy-3-(4-tert-octylphenoxy)-2-propanol or 1-isopropoxy-3-(4-tert-octylphenoxy)-2-propanol.

12. A method of separating cesium and strontium from an aqueous feed, comprising:
contacting an aqueous feed comprising cesium and strontium with a mixed extractant solvent,
the mixed extractant solvent comprising:
at least one dialkyloxycalix[4]arenebenzocrown-6 compound;
4',4',(5')-di-(t-butyldicyclo-hexano)-18-crown-6; and
at least one modifier comprising an alkylphenoxy alcohol compound lacking fluorine substituents, wherein the alkylphenoxy alcohol compound is not 2-(4-tert-octylphenoxy)-1-ethanol,1-ethoxy-3-(4-tert-octylphenoxy)-2-propanol or 1-isopropoxy-3-(4-tert-octylphenoxy)-2-propanol; and
removing the cesium and strontium from the aqueous feed.

13. The method of claim 12, wherein the at least one dialkyloxycalix[4]arenebenzocrown-6 compound comprises 1,3-alternate-25,27-di(octyloxy)calix[4]arenebenzocrown-6,1,3-alternate-25, 27-di(decyloxy)calix[4]arenebenzocrown-6,1,3-alternate-25,27-di(dodecyloxy) calix[4]arenebenzocrown-6, 1,3-alternate-25,27-di(2-ethylhexyl-1-oxy)calix[4]arene -benzocrown-6,1,3-alternate-25,27-di(3,7-dimethyloctyl-1-oxy)calix[4]arenebenzocrown-6, 1,3-alternate-25,27-di(4-butyloctyl-1-oxy)calix[4]arenebenzocrown-6, or combinations thereof.

14. The method of claim 12, wherein the at least one modifier comprises at least one alkylphenoxy ethyl alcohol lacking fluorine substituents, at least one alkylphenoxy propyl alcohol lacking fluorine substituents, or combinations thereof.

15. The method of claim 12, wherein the at least one modifier comprises 3-[4-(tert-octyl)phenoxy]-1-propanol, 3-[4-(sec-butyl)phenoxy]-1-propanol, 3-[4-(tert-octyl)phenoxy]-2-methyl-1-propanol, 3-[4-(sec-butyl)phenoxy]-2-methyl-1-propanol, or combinations thereof.

16. The method of claim 12, wherein the at least one modifier comprises 1-hexanol, 1-heptanol, 1-octanol, 1-nonanol, 1-decanol, 1-undecanol, 1-dodecanol, or combinations thereof.

17. The method of claim 12, wherein the at least one modifier comprises methylpentanol, ethylbutanol, methylhexanol, ethylpentanol, methylheptanol, ethylhexanol, methyloctanol, ethylheptanol, methylnonanol, ethyloctanol, methyldecanol, ethylnonanol, methylundecanol, ethyldecanol, methyldodecanol, ethylundecanol, or combinations thereof.

18. The method of claim 12, wherein contacting an aqueous feed comprising cesium and strontium with a mixed extractant solvent comprises contacting the aqueous feed with a mixed extractant solvent comprising from approximately 7mM to approximately 50 mM of the at least one dialkyloxycalix[4]arenebenzocrown-6compound, from approximately 10 mM to approximately 500 mM of 4',4',(5')-di-(t-butyldicyclo-hexano)-18-crown-6, and from approximately 0.5 M to approximately 3.0 M of the at least one modifier.

19. The method of claim 12, wherein contacting an aqueous feed comprising cesium and strontium with a mixed extractant solvent comprises contacting the aqueous feed comprising a nitric acid concentration of from approximately 1.5 M to approximately 5 M with the mixed extractant solvent.

20. The method of claim 12, wherein contacting an aqueous feed comprising cesium and strontium with a mixed extractant solvent comprises extracting the cesium and strontium into the mixed extractant solvent.

21. A calixarene compound comprising:

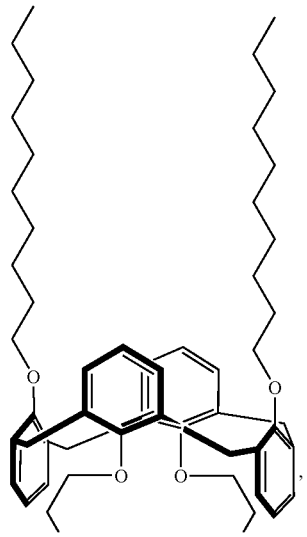

-continued
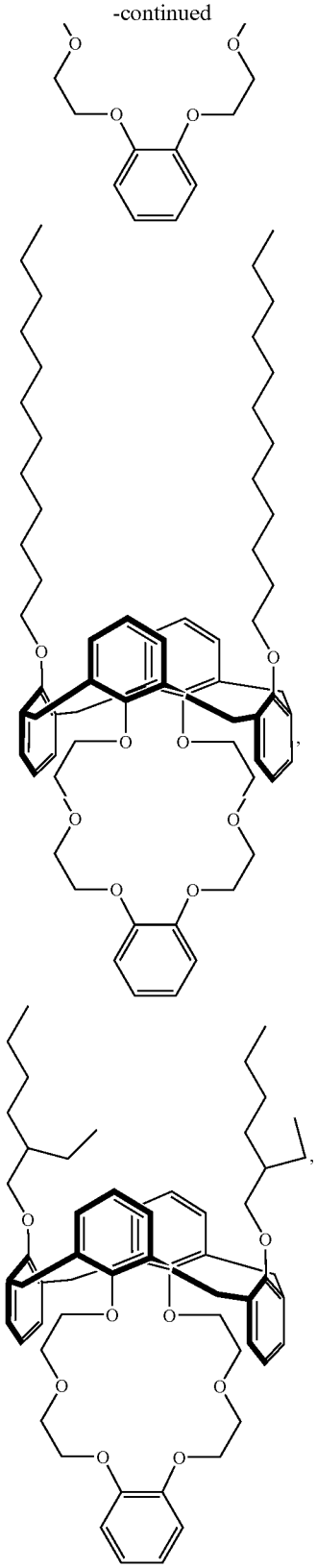
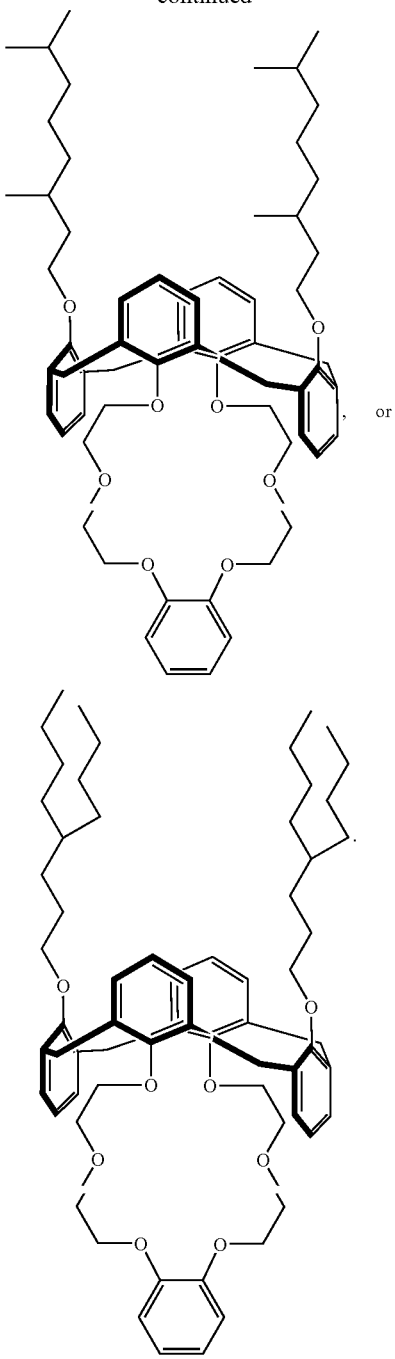
22. A mixed extractant solvent, comprising:
calix[4]arene-bis(tert-octylbenzo)-crown-6 ("BOB-CalixC6"),4',4',(5')-di-(t-butyldicyclo-hexano) -18-crown-6 ("DtBuCH18C6"),3-[4-(sec-butyl)phenoxy]-2-methyl-1-propanol, and a diluent.
* * * * *